United States Patent [19]

Crenshaw et al.

[11] 4,380,638

[45] Apr. 19, 1983

[54] CHEMICAL COMPOUNDS

[75] Inventors: Ronnie R. Crenshaw, Dewitt; Aldo A. Algieri, Fayetteville, both of N.Y.

[73] Assignee: Bristol-Myers Company, New York, N.Y.

[21] Appl. No.: 276,602

[22] Filed: Jun. 23, 1981

Related U.S. Application Data

[60] Division of Ser. No. 240,034, Mar. 3, 1981, which is a continuation-in-part of Ser. No. 163,831, Jul. 7, 1980, abandoned, which is a continuation-in-part of Ser. No. 117,182, Jan. 31, 1980, abandoned, which is a continuation-in-part of Ser. No. 72,517, Sep. 4, 1979, abandoned.

[51] Int. Cl.$^3$ .......................................... C07D 285/10
[52] U.S. Cl. .................. 548/135; 260/245.5; 424/246; 424/248.51; 424/250; 424/263; 424/267; 424/269; 544/60; 544/134; 544/367; 546/193; 546/209; 546/256; 546/277; 548/131
[58] Field of Search ............... 548/135, 131; 546/193, 546/209, 256, 277; 544/134, 367; 260/245.5

[56] References Cited

U.S. PATENT DOCUMENTS 3,247,193  4/1966  Menzl ............................... 548/135
3,642,811  2/1972  Vorreither et al. ................ 548/135

OTHER PUBLICATIONS

Wen et al.; J. Org. Chem. vol. 40, pp. 2743–2748, (1975).
Carmack et al.; Organic Preparations and Procedures, vol. 1, pp. 255–258, (1969).

*Primary Examiner*—Mary C. Lee
*Attorney, Agent, or Firm*—Richard R. Lloyd

[57] ABSTRACT

Histamine H$_2$-antagonists of the formula

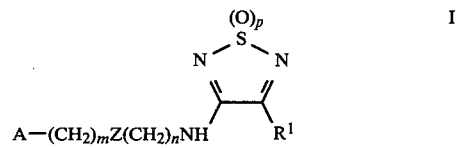

wherein p is 1 or 2; R$^1$ is hydroxy, amino, substituted amino or a 5- to 9-membered fully saturated nitrogen-containing heterocyclic ring attached via its nitrogen atom; m is an integer of from 0 to 2; n is an integer of from 2 to 4; Z is sulfur, oxygen or methylene; and A is an optionally substituted phenyl, imidazolyl, thiazolyl, isothiazolyl, oxazolyl, isoxazolyl, triazolyl, thiadiazolyl, oxadiazolyl, furyl, thienyl or pyridyl ring; and nontoxic pharmaceutically acceptable salts, hydrates, solvates or N-oxides thereof are novel anti-ulcer agents. Intermediates and processes for their preparation are disclosed.

23 Claims, No Drawings

CHEMICAL COMPOUNDS

CROSS-REFERENCE TO RELATED APPLICATIONS

This application is a divisional of our co-pending application Ser. No. 240,034, filed Mar. 3, 1981, which is a continuation-in-part of application Ser. No. 163,831, filed July 7, 1980 (and now abandoned), which is a continuation-in-part of application Ser. No. 117,182, filed Jan. 31, 1980 (and now abandoned), which is a continuation-in-part of application Ser. No. 72,517, filed Sept. 4, 1979 (and now abandoned).

SUMMARY OF THE INVENTION

Certain 3-(hydroxy or amino)-4-(substituted amino)- and 3,4-di(substituted amino)-1,2,5-thiadiazole 1-oxides and 1,1-dioxides are potent histamine $H_2$-antagonists, inhibit gastric acid secretion and are useful in the treatment of peptic ulcers.

BACKGROUND AND PRIOR ART

Burimamide (IIa) was the first clinically effective $H_2$-receptor antagonist. It inhibits gastric secretion in animals and man, but oral absorption is poor.

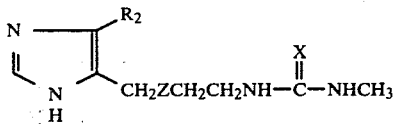

II

IIa; $R^2$ = H, Z = $CH_2$, X = S Burimamide
b; $R^2$ = $CH_3$, Z = S, X = S Metiamide
c; $R^2$ = $CH_3$, Z = S, X = NCN Cimetidine Metiamide (IIb), a subsequently evaluated $H_2$-antagonist, is more potent than burimamide and is orally active in man. Clinical utility was limited, however, owing to toxicity (agranulocytosis). Cimetidine (IIc) is as effective an $H_2$-antagonist as metiamide, without producing agranulocytosis, and has recently been marketed as an anti-ulcer drug.

Reviews on the development of $H_2$-antagonists, including those discussed in the preceding paragraph, may be found in C. R. Ganellin, et al., *Federation Proceedings*, 35, 1924 (1976), in *Drugs of the Future*, 1, 13 (1976), and in references cited therein. Relevant patents are as follows:

U.S. Pat. No. 4,098,898 is representative of a large number of patents disclosing broad classes of histamine $H_2$-antagonists which are N,N'-(disubstituted)thioureas, N,N'-(disubstituted)guanidines and/or N,N'-disubstituted-1,1-diaminoethylenes in which at least one of the N-substituents is a broadly defined heterocyclylalkylthioalkyl, heterocyclylalkoxyalkyl or heterocyclylalkyl moiety. The heterocyclyl ring is often broadly defined as being a 5- or 6-membered N-containing heterocyclic ring which optionally contains additional hetero atoms selected from N, S and O, and which is optionally substituted. U.S. Pat. No. 4,098,898 discloses compounds of the formula

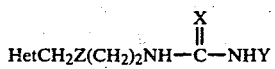

wherein X is sulfur, $CHNO_2$, NCN or NH; Y is amino, (lower)alkylamino, di(lower)alkylamino, (lower)alkoxy, phenylethyl, imidazolylethyl, allyl, 2,2,2-trifluoroethyl or $(CH_2)_nR$; Z is sulfur or methylene; Het is an imidazole, pyridine, thiazole, isothiazole, oxazole, isoxazole, triazole or thiadiazole ring which is optionally substituted by (lower)alkyl, hydroxy, halogen or amino; n is 1-12; and R is hydroxy, (lower)alkoxy, amino or (lower)alkylamino; provided that when X is NH, Y is 2,2,2-trifluoroethyl or $(CH_2)_nR$ and that when X is NCN, Y is not amino or (lower)alkylamino.

U.S. Pat. No. 4,062,863 discloses histamine $H_2$-antagonists of the formula

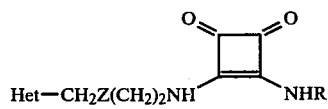

wherein R is hydrogen, (lower)alkyl or —$(CH_2)_2Z'CH_2Het'$; Z and Z' each are sulfur or methylene; and Het and Het' each are an imidazole ring optionally substituted by methyl or bromo, a pyridine ring optionally substituted by hydroxy, methoxy, chloro or bromo, a thiazole ring or an isothiazole ring; and pharmaceutically acceptable acid addition salts thereof. U.S. Pat. Nos. 4,120,968 and 4,120,973 are related cases having substantially identical disclosures.

U.S. Pat. No. 4,104,381 discloses histamine $H_2$-antagonists of the formula

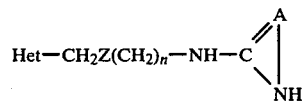

wherein Het is a nitrogen-containing heterocycle such as imidazole, pyridine, thiazole, isothiazole or thiadiazole which is optionally substituted by (lower)alkyl, amino, hydroxy or halogen; Z is sulfur or methylene; n is 2 or 3; and A, taken together with the nitrogen and carbon atoms to which it is attached, forms a pyrimidine, imidazoline, quinazoline, pyridine, benzothiadiazine, 1,2,4-thiadiazine, thiazoline, 1,2,4-triazine or quinoline ring, said ring having a keto, thione or sulfone group and being optionally substituted by one or two (lower)alkyl, phenyl or benzyl groups; and pharmaceutically acceptable acid addition salts thereof. This patent includes within its scope, and states to be one of four "particularly important" classes, substituted 1,2,4-thiadiazine compounds of the formula

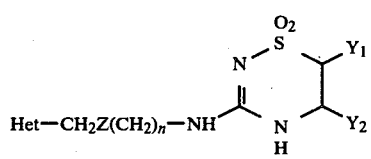

wherein Het is as defined above, Z is sulfur or methylene, and $Y^1$ and $Y^2$ are independently hydrogen, (lower)alkyl, phenyl or benzyl, or $Y^1$ and $Y^2$, taken together with the adjacent carbon atoms, may form a fused phenyl ring. U.S. Pat. Nos. 3,932,644, 4,005,205, 4,035,374 and 4,153,793 are related cases having substantially the same disclosure.

Belgian Pat. No. 864,992 discloses compounds which are simultaneously histamine $H_1$-antagonists and histamine $H_2$-antagonists having the formula

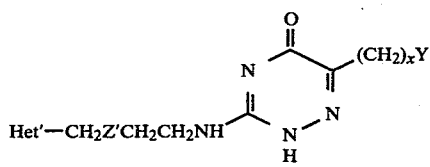

wherein Het' is a 2- or 4-benzimidazolyl ring which is optionally substituted by (lower)alkyl, halogen, $CF_3$ or $CH_2OH$, a 2-pyridyl ring which is optionally substituted by 1 or 2 (lower)alkyl, (lower)alkoxy, halogen, amino or OH groups, a 2-pyridyl ring condensed with a phenyl group or with a cyclic ether containing 2 oxygen atoms, a 2-thiazolyl ring, a 3-isothiazolyl ring which is optionally substituted by Cl or Br, a 1,2,5-thiadiazol-3-yl ring which is optionally substituted by Cl or Br, or a 5-amino-1,3,4-thiadiazol-2-yl ring; Z' is $CH_2$ or S; x is 1-5; Y is 1- or 2-naphthyl, 2,3-dihydro-1,4-benzodioxinyl, 1,3-benzodioxolyl, phenyl substituted by one or more alkyl, (lower)alkoxy, halogen, aralkoxy, OH, alkoxyalkoxy, $CF_3$, di(lower)alkylamino, phenoxy, halophenoxy, alkoxyphenoxy, phenyl, halophenyl or alkoxyphenyl groups, or Y is a 5- or 6-membered heterocyclyl ring which is optionally substituted by a (lower)alkyl or (lower)alkoxy group, and optionally has a fused benzene ring; and when x is 2-5, Y may also be phenyl.

U.S. Pat. No. 4,128,658 discloses histamine $H_2$-antagonists of the formula

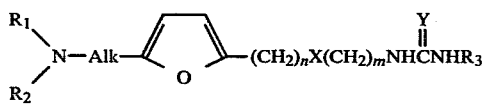

wherein $R_1$ and $R_2$ are hydrogen, (lower)alkyl, cycloalkyl, (lower)alkenyl, aralkyl or (lower)alkyl interrupted by an oxygen atom or the group $-N(R_4)-$ in which $R_4$ is hydrogen or (lower)alkyl, or $R_1$ and $R_2$ taken together with the N atom to which they are attached may form a heterocyclic ring optionally containing other heteroatoms selected from O and $-N(R_4)-$; $R_3$ is hydrogen, (lower)alkyl, (lower)alkenyl or alkoxyalkyl; X is $-CH_2-$, O or S; Y is S, O, $NR_5$ or $CHR_6$; Alk is a straight or branched alkylene chain of 1 to 6 carbon atoms; $R_5$ is H, $NO_2$, CN, (lower) alkyl, aryl, alkylsulfonyl or arylsulfonyl; $R_6$ is $NO_2$, arylsulfonyl or alkylsulfonyl; m is an integer of from 2 to 4; n is 1 or 2, or, when X is S or $CH_2$, n is 0, 1 or 2; and physiologically acceptable salts, hydrates and N-oxides thereof. The disclosure of U.K. Published Application No. 2,006,771 is substantially the same as U.S. Pat. No. 4,128,658 except that X may not be methylene, and the furan ring has a substituent adjacent the dialkylaminoalkyl group which is selected from (lower)alkyl, (lower)alkoxy(lower)alkyl, hydroxy(lower)alkyl, (lower)alkoxycarbonyl, (lower)alkylthio(lower)alkyl, halogen and aryl.

The disclosure of Belgian Pat. No. 867,106 is similar to that of U.S. Pat. No. 4,128,658, except that the disubstituted furyl ring is replaced by a similarly disubstituted phenyl ring.

The disclosure of Belgian Pat. No. 867,105 is similar to that of U.S. Pat. No. 4,128,658 except that the disubstituted furyl ring is replaced by a similarly disubstituted thienyl ring.

U.K. Published Patent Application No. 2,001,624 discloses histamine $H_2$-antagonists of the formula

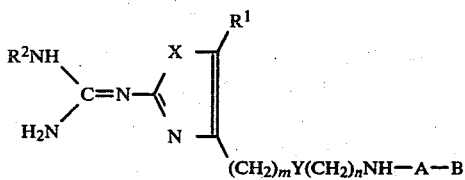

wherein X is S or NH; Y is O, S, SO, $CH_2$, a direct bond or a vinylene radical; m is 0 to 4; n is 1 to 4; $R^1$ is H, halogen or alkyl; $R^2$ is hydrogen, alkyl, alkanoyl or aroyl; A is a 3,4-dioxocyclobuten-1,2-diyl radical or $C=Z$ in which Z is O, S, NCN, $NNO_2$, $CHNO_2$, $NCONH_2$, $C(CN)_2$, $NCOR^3$, $NCO_2R^3$, $NSO_2R^3$ or $NR^4$ in which $R^3$ is alkyl or aryl and $R^4$ is hydrogen or alkyl; B is alkoxy, alkylthio or $NR^5R^6$ in which $R^5$ and $R^6$ are independently hydrogen, alkyl, alkenyl, cycloalkyl, hydroxyalkyl, alkoxyalkyl, alkylaminoalkyl or dialkylaminoalkyl; and salts thereof.

Belgian Pat. No. 866,155 discloses histamine $H_2$-antagonists of the formula

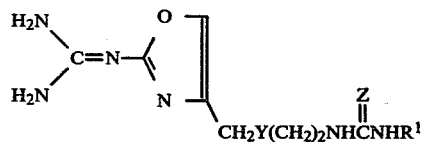

wherein $R^1$ is H or (lower)alkyl; Y is S or $CH_2$; and Z is S or NCN; and pharmaceutically acceptable acid addition salts thereof.

U.S. Pat. No. 4,112,234 discloses histamine $H_2$-antagonists of the formula

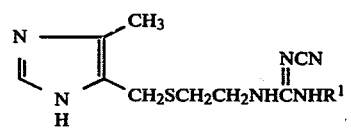

wherein $R^1$ is a straight or branched chain alkynyl group containing from 3 to 9 carbon atoms; and nontoxic pharmaceutically acceptable salts thereof.

U.S. Pat. No. 4,145,546 discloses compounds which are simultaneously histamine $H_1$-antagonists and histamine $H_2$-antagonists, having the formula

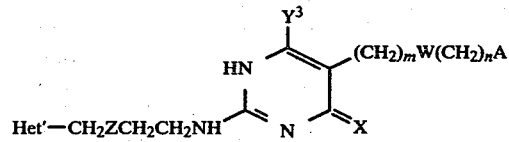

wherein Het' is a 2- or 4-imidazolyl ring optionally substituted by (lower)alkyl, halogen, trifluoromethyl or hydroxymethyl, a 2-pyridyl ring optionally substituted by (lower)alkyl, (lower)alkoxy, halogen, amino or hydroxy, a 2-pyridyl ring which is disubstituted by (lower)alkoxy groups or which has a phenyl, carbocyclic or cyclic ether ring containing two oxygen atoms fused to it, a 2-thiazolyl ring, a 3-thiazolyl ring optionally substituted by chlorine or bromine, a 3-(1,2,5-thiadiazolyl) ring optionally substituted by chlorine or bromine, or a 2-(5-amino-1,3,4-thiadiazolyl) ring; Z is sulfur or methylene; X is oxygen or sulfur; W is methylene, oxygen or sulfur; m and n are such that their sum is from 1 to 4 when W is oxygen or sulfur, or from 0 to 4 when W is methylene; A is a 1- or 2-naphthyl ring, a 2,3-dihydro-1,4-benzodioxinyl ring, a 1,3-benzodioxolyl ring or a phenyl ring substituted by one or more (lower)alkyl, (lower)alkoxy, halogen, arylalkoxy, hydroxy, (lower)alkoxy(lower)alkyl, trifluoromethyl, di(lower)alkylamino, phenoxy, halophenoxy, (lower)alkoxyphenoxy, phenyl, halophenyl or (lower)alkoxyphenyl groups; and when —$(CH_2)_mW(CH_2)_n$— is not a methylene group, A may also be phenyl; and $Y^3$ is hydrogen or (lower)alkyl; and acid addition salts thereof. The disclosure of U.S. Pat. No. 4,159,329 is substantially the same as that of U.S. Pat. No. 4,145,546. The disclosure of U.S. Pat. No. 4,154,834 is substantially the same as that of U.S. Pat. No. 4,145,546, except that A is a 5- or 6-membered heterocyclic ring selected from pyridine, pyridine-N-oxide, furan, thiophene, thiazole, oxazole, isothiazole, imidazole, pyrimidine, pyrazine, pyridazine and thiadiazole, which are optionally substituted by 1 or 2 (lower)alkyl, (lower)alkoxy, halogen, hydroxy or amino groups, or A is a pyridine ring with a carbocyclic or cyclic ether ring containing two oxygen atoms fused to it; or A is a pyridine, imidazole or thiazole ring having a benzene ring fused to it.

U.K. Published Patent Application Ser. No. 2,023,133 discloses histamine $H_2$-antagonists of the formula

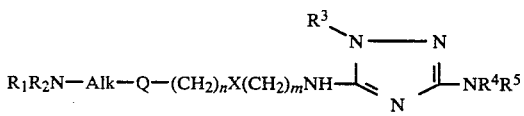

wherein $R_1$ and $R_2$ are independently hydrogen, alkyl, cycloalkyl, alkenyl, alkynyl, aralkyl, trifluoroalkyl or alkyl substituted by hydroxy, alkoxy, amino, alkylamino, dialkylamino or cycloalkyl, or $R_1$ and $R_2$, taken together with the nitrogen to which they are attached, may be a 5 to 10-membered alicyclic heterocyclic ring which may be saturated or may contain at least one double bond, which may be substituted by one or more alkyl groups or a hydroxy group and/or which may contain another heteroatom; Alk is a straight or branched alkylene chain of 1–6 carbon atoms; Q is a furan or thiophene ring incorporated into the molecule via the 2- and 5-positions, the furan ring optionally bearing a further substituent $R_7$ adjacent the $R_1R_2N$-Alk-group, or Q is a benzene ring incorporated into the molecule via its 1- and 3- or 1- and 4-positions; $R_7$ is halogen, alkyl (which may be substituted by hydroxy or alkoxy); X is methylene, oxygen, sulfur or >N-$R^6$ in which $R^6$ is hydrogen or methyl; n is 0, 1 or 2; m is 2, 3 or 4; $R_3$ is hydrogen, alkyl, alkenyl, aralkyl, hydroxyalkyl having at least two carbon atoms, alkoxyalkyl or aryl; and $R_4$ and $R_5$ are independently hydrogen, alkyl, alkyl substituted by hydroxy or $C_{1-3}$ alkoxy, alkenyl, aralkyl or heteroaralkyl, or $R_4$ and $R_5$ taken together with the nitrogen to which they are attached, may be a 5 to 7-membered saturated heterocyclic ring which may contain another heteroatom or the group >$NR^6$, or $R_4$ and $R_5$ taken together may be the group >$CR_8R_9$ wherein $R_8$ is aryl or heteroaryl and $R_9$ is hydrogen or alkyl; and physiologically acceptable salts and hydrates thereof.

Although the three other isomeric thiadiazoles (the 1,2,3-, 1,2,4- and 1,3,4-isomers) were known previously, 1,2,5-thiadiazole was first prepared in 1958. Since that time a large number of 3-substituted- and 3,4-disubstituted-1,2,5-thiadiazoles have been reported in the literature, including a small number of simple 3,4-di(substituted amino)-1,2,5-thiadiazoles, e.g. the 3,4-bis(dimethylamino) compound. See, for example the review in Advances in Heterocyclic Chemistry, A. R. Katritzky and A. J. Boulton, Eds., 9, 107–163, Academic Press, New York (1968) and the publications in J. Het. Chem., 13, 13 (1976) and J. Med. Chem., 15, 315 (1972). A moderate number of 3,4-disubstituted-1,2,5-thiadiazole 1,1-dioxides are known, including the 3,4-dichloro-, 3,4-dimethoxy- and 3,4-diethoxy useful as starting materials for the preparation of compounds of Formula I in which p is 2. 3,4-Diamino- and a small number of simple 3,4-di(-substituted amino)-1,2,5-thiadiazole 1,1-dioxides are known, e.g. the bis(methylamino)-, bis(dimethylamino)- and bis(o-carboxyphenylamino)- compounds. See, for example, the above-cited review article and J. Org. Chem., 40, 2743 (1975). Similar derivatives of 1,2,5-thiadiazole 1-oxide have not been reported. Certain 3-hydroxy-4-(substituted amino) derivatives of 1,2,5-thiadiazoles are known. For example, J. Org. Chem., 41, 3121 (1976) reports the synthesis of 3-hydroxy-4-(N-morpholino)-1,2,5-thiadiazole and J. Org. Chem., 40, 2743 (1975) reports the preparation of 3-hydroxy-4-(N-piperidino)-1,2,5-thiadiazole 1,1-dioxide. Correspondingly substituted 1,2,5-thiadiazole 1-oxides apparently are not known. To our knowledge, the only reported disubstituted 1,2,5-thiadiazole 1-oxide is the 3,4-dihydroxy compound. None of the 3,4disubstituted-1,2,5-thiadiazole derivatives of the present invention are known. None of the above-cited known 3,4-disubstituted-1,2,5-thiadiazole derivatives have been reported to have $H_2$-antagonist or anti-ulcer activity.

Complete Disclosure

This application relates to histamine $H_2$-antagonists which are effective inhibitors of gastric acid secretion in animals, including man, which are useful in the treatment of peptic ulcer disease, and which have the formula

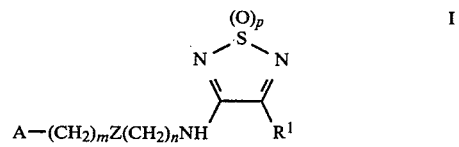

wherein
p is 1 or 2;
$R^1$ is hydroxy or $NR^2R^3$;
$R^2$ and $R^3$ each are independently hydrogen, (lower)alkyl, (lower)alkenyl, (lower)alkynyl, cyclo(lower)alkyl(lower)alkyl, hydroxy(lower)alkyl, (lower)alkoxy(lower)alkyl, (lower)alkylthio(lower)alkyl, 2-fluoroethyl, 2,2,2-trifluoroethyl or cyano(lower)alkyl, or, when $R^2$ is hydrogen, $R^3$ may also be cyclo(lower)alkyl, amino(lower)alkyl, (lower)alkylamino(lower)alkyl, di(lower)alkylamino(lower)alkyl, pyrrolidino(lower)alkyl, piperidino(lower)alkyl, morpholino(lower)alkyl, piperazino(lower)alkyl, pyridyl(lower)alkyl, substituted pyridyl(lower)alkyl wherein the pyridyl ring may contain one substituent selected from (lower)alkyl, (lower)alkoxy, hydroxy, amino and halogen, amino, (lower)alkylamino, di(lower)alkylamino, hydroxy, (lower)alkoxy, 2,3-dihydroxypropyl, cyano, amidino, (lower)alkylamidino, A'—(CH$_2$)$_{m'}$Z'(CH$_2$)$_{n'}$—, phenyl, phenyl(lower)alkyl, substituted phenyl or substituted phenyl(lower)alkyl, wherein the phenyl ring may contain one or two substituents independently selected from (lower)alkyl, hydroxy, (lower)alkoxy and halogen or one substituent selected from methylenedioxy, trifluoromethyl and di(lower)alkylamino; or R$^2$ and R$^3$, taken together, may be —CH$_2$CH$_2$X(CH$_2$)$_r$—;

r is an integer of from 1 to 3, inclusive;

X is methylene, sulfur, oxygen or N-R$^4$, provided that, when r is 1, X is methylene;

R$^4$ is hydrogen, (lower)alkyl, (lower)alkenyl, (lower)alkynyl, (lower)alkanoyl or benzoyl;

m and m' each are independently an integer of from zero to 2, inclusive;

n and n' each are independently an integer of from 2 to 4, inclusive;

Z and Z' each are independently sulfur, oxygen or methylene;

A and A' each are independently phenyl, imidazolyl, thiazolyl, isothiazolyl, oxazolyl, isoxazolyl, triazolyl, thiadiazolyl, oxadiazolyl, furyl, thienyl or pyridyl; provided that A and A' independently may contain one or two substituents, the first substituent being selected from (lower)alkyl, hydroxy, trifluoromethyl, halogen, amino, hydroxymethyl, (lower)alkoxy,

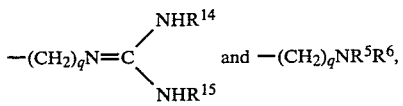

and the second substituent being selected from (lower)alkyl, hydroxy, trifluoromethyl, halogen, amino, hydroxymethyl and (lower)alkoxy;

q is an integer of from 0 to 6, inclusive; R$^{14}$ and R$^{15}$ independently are hydrogen or (lower)alkyl, or, if R$^{14}$ is hydrogen, R$^{15}$ also may be (lower)alkanoyl or benzoyl, or R$^{14}$ and R$^{15}$, taken together, may be ethylene; and R$^5$ and R$^6$ each are independently hydrogen, (lower)alkyl, (lower)alkenyl, (lower)alkynyl, (lower)alkoxy(lower)alkyl, cyclo(lower)alkyl, phenyl or phenyl(lower)alkyl, provided that R$^5$ and R$^6$ may not both be cyclo(lower)alkyl or phenyl; or R$^5$ and R$^6$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino;

or a nontoxic, pharmaceutically acceptable salt, hydrate, solvate or N-oxide thereof.

This application also relates to processes for the preparation of the compounds of Formula I and to intermediates in the preparation of compounds of Formula I.

The present invention includes within its scope all possible tautomeric forms, geometric isomers, optical isomers and zwitterionic forms of the compounds of Formula I as well as mixtures thereof. As used herein and in the claims, the terms "(lower)alkyl," "(lower)alkenyl," "(lower)alkynyl," "(lower)alkoxy" and "(lower)alkylthio" mean, in their broadest sense, straight or branched chain alkyl, alkenyl, alkynyl, alkoxy and alkylthio groups containing from 1 to 12 carbon atoms. Preferably, these groups contain from 1 to 8 carbon atoms and, most preferably, from 1 to 6 carbon atoms. The term "nontoxic pharmaceutically acceptable salts" includes not only acid addition salts, but also alkali metal and alkaline earth metal salts. Compounds of Formula I have been found to form metallic salts such as potassium, sodium and calcium salts. It is believed that these salts are formed by displacement of a proton from the hydroxy group (when R$^1$ is hydroxy) or from one of the nitrogen atoms adjacent the thiadiazole ring, but this is only theory and in no way limits the invention thereto.

In the compounds of Formula I, A and A', independently, are preferably optionally substituted phenyl, imidazolyl, thiazolyl, oxazolyl, thiadiazolyl, oxadiazolyl, furyl, thienyl or pyridyl rings. Most preferably, A and A', independently, are optionally substituted phenyl, imidazolyl, thiazolyl, furyl, thienyl or pyridyl rings. Particularly preferred A and A' groups are guanidino-substituted thiazolyl, di(lower)alkylamino(lower)alkyl-substituted (and especially dimethylaminomethyl-substituted) furyl, di(lower)alkylamino(lower)alkyl-substituted (and especially dimethylaminomethyl-substituted) thiazolyl, di(lower)alkylamino(lower)alkyl-substituted (and especially dimethylaminomethyl-substituted) phenyl, guanidino-substituted phenyl, cycloalkyleneimino(lower)alkyl-substituted (and especially cycloalkyleneiminomethyl-substituted) phenyl and di(lower)alkylamino(lower)alkyl-substituted (and especially dimethylaminomethyl-substituted) thienyl moieties.

It is preferred that m is zero or 1 and n is 2 or 3. Preferably, X is sulfur, oxygen or methylene (and most preferably sulfur or oxygen). R$^1$ preferably is NR$^2$R$^3$ in which R$^2$ and R$^3$ preferably are each independently selected from hydrogen, (lower)alkyl, (lower)alkenyl, (lower)alkynyl, pyridyl(lower)alkyl or A'—(CH$_2$)$_{m'}$Z'(CH$_2$)$_{n'}$—. In particularly preferred embodiments, R$^2$ is hydrogen and R$^3$ is hydrogen, (lower)alkyl (especially methyl, ethyl or propyl), (lower)alkenyl (especially 2-propenyl), (lower)alkynyl (especially 2-propynyl), pyridyl(lower)alkyl or A'—(CH$_2$)$_{m'}$Z'(CH$_2$)$_{n'}$— in which m' is preferably zero or 1, n' is preferably 2 or 3, Z' is preferably sulfur or oxygen, and A' is preferably a substituted thiazolyl, phenyl or furyl ring (and especially guanidino-substituted thiazolyl, dimethylaminomethyl-substituted phenyl, dimethylaminomethyl-substituted furyl or guanidino-substituted phenyl).

The compounds of Formula I may be prepared by various procedures, preferably starting from a compound of the formula

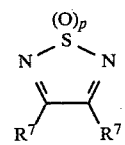

in which R$^7$ is a good leaving group such as halogen, phenoxy, substituted phenoxy, phenylthio, substituted phenylthio, alkoxy, alkylthio, and the like. Suitable leaving groups are well known to those skilled in the art. Preferably, R$^7$ is (lower)alkoxy (especially methoxy).

Preparation of Starting Materials

Starting materials of Formula II in which p is 2 and each $R^7$ is chloro, methoxy or ethoxy are known, their preparation being described in *J. Org. Chem.* 40, 2743 (1975). Starting materials of Formula II in which p is 2 and each $R^7$ is alkoxy, alkylthio, phenoxy, phenylthio, substituted phenoxy or substituted phenylthio (compounds of Formula IV and V) may be prepared by reacting the dichloro compound of Formula III with the appropriate alkanol, alkylthiol, phenol, thiophenol, substituted phenol or substituted thiophenol to produce the corresponding compound of Formula IV or V in which $R^8$ is alkyl, phenyl or substituted phenyl, as follows:

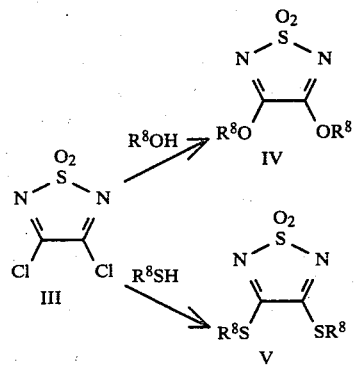

The reaction is conducted in an inert organic solvent such as ether, dimethylformamide, or the like. When reactant $R^8OH$ or $R^8SH$ is a liquid, e.g. methanol, ethanol, ethylmercaptan or thiophenol, the reaction may be conducted in an excess of that reactant as a solvent. Corresponding starting materials of Formula II in which p is 1 (compounds of Formula VII and VIII) may be prepared in the same manner from a compound of Formula II in which each $R^7$ is chloro (compound VI).

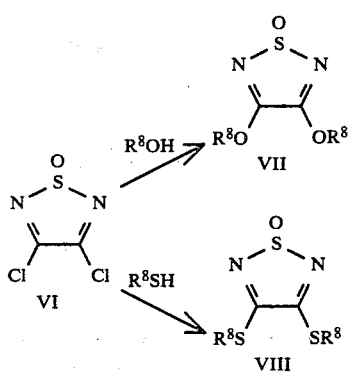

Compound VI is a novel compound but it may be prepared from the known compound 3,4-dihydroxy-1,2,5-thiadiazole 1-oxide [itself prepared according to the procedure of *Org. Prep. Proced.*, 1, 255 (1969)] by the same procedure utilized for preparing the compound of Formula III from 3,4-dihydroxy-1,2,5-thiadiazole 1,1-dioxide [see *J. Org. Chem.*, 40, 2743 (1975)]. The starting materials of Formulae VII and VIII are novel compounds not previously described in the literature.

Alternatively, the starting materials of Formulae IV and VII may be prepared by reaction of an appropriately substituted oxaldiimidate ester of Formula IX with $SCl_2$ or $S_2Cl_2$ in an inert solvent such as dimethylformamide to form the correspondingly 3,4-disubstituted 1,2,5-thiadiazole of Formula X which is then oxidized to the corresponding 1-oxide of Formula VII or 1,1-dioxide of Formula IV.

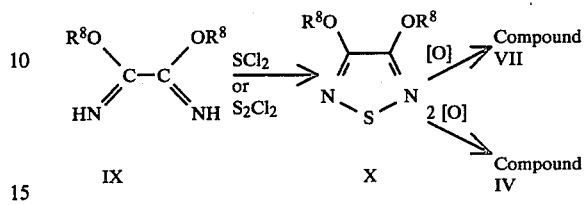

Oxaldiimidate esters of Formula IX in which $R^8$ is methyl, ethyl, n-propyl, isopropyl, n-butyl and n-pentyl are known and their preparation is described in *Chem. Ber.*, 107, 3121 (1974). Corresponding compounds in which $R^8$ is phenyl, optionally substituted by (lower)alkyl, (lower)alkoxy, halogen or nitro may be prepared by a similar procedure. Compounds of Formula X in which $R^8$ is methyl or ethyl are described in *J. Org. Chem.*, 40, 2749 (1975).

The literature reports that the 1,2,5-thiadiazole nucleus is sensitive to oxidation, that oxidation of thiadiazoles with peracids is usually accompanied by ring destruction and formation of sulfate ion, and that attempts to prepare 1,2,5-thiadiazole 1,1-dioxide by peracetic acid oxidation of the parent ring resulted in ring cleavage. Surprisingly, we have found that the 3,4-disubstituted-1,2,5-thiadiazole 1-oxides of Formula VII and 1,1-dioxides of Formula IV may readily be prepared in good yield by oxidation of the correspondingly 3,4-disubstituted-1,2,5-thiadiazole of Formula X with a peracid such as m-chloroperbenzoic acid, in an inert solvent such as chloroform. The preparation of 3,4-dimethoxy-1,2,5-thiadiazole 1-oxide is shown in Example 4, Step A; the preparation of the corresponding 1,1-dioxide is shown below.

Illustrative Procedure No. 1

3,4-Dimethoxy-1,2,5-thiadiazole 1,1-dioxide

A solution of 3,4-dimethoxy-1,2,5-thiadiazole (1.48 g; 10.1 mmoles) [prepared according to the procedure described in *J. Org. Chem.*, 40, 2749 (1975)] in 20 ml of chloroform was added over a period of 1 minute to a stirred solution of m-chloroperbenzoic acid (4.11 g; 20.3 mmoles; 85% assay) in 60 ml of chloroform. After stirring at ambient temperature for 1 hour, the mixture was heated at reflux temperature for 8 hours and then stirred at ambient temperature for 1 hour. The reaction mixture was extracted with aqueous sodium bicarbonate and water, and the organic phase was dried over sodium sulfate, filtered and evaporated under reduced pressure. The residue was treated with methanol and filtered to give 1.03 g of product. Recrystallization from methanol yielded the title compound, mp 200°–202°.

Anal. Calcd. for $C_4H_6N_2O_4S$: C, 26.97; H, 3.39; N, 15.72; S, 18.00. Found: C, 26.82; H, 3.18; N, 16.09; S, 18.00.

We have now found a particularly elegant procedure by which a compound of Formula VII may be prepared in a one-step reaction directly from a compound of Formula IX, by reaction of the latter with thionyl chloride. This

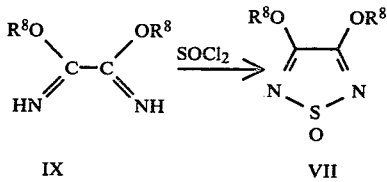

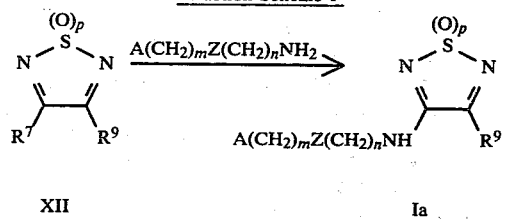

reaction is conducted in an inert organic solvent such as methylene chloride, chloroform, or the like. Although the reaction may be conducted without the addition of a base as an acid scavenger, we prefer to add about two equivalents of a base to remove the HCl which is formed is the reaction. Higher yields of Compound VII are thereby obtained. Suitable bases include inorganic bases such as sodium carbonate, potassium carbonate, sodium bicarbonate and potassium bicarbonate, and organic bases such as triethylamine, pyridine and the like. This process not only eliminates one step, but is much more economical in that it avoids the use of expensive oxidizing agents such as m-chloroperbenzoic acid. The reaction may be conducted at a temperature of from about $-20°$ to about $25°$, and preferably at about $0°$ to about $10°$. Illustrative Procedure No. 2 shows the preparation, by this process, of the compound of Formula VII in which $R^8$ is methyl.

Illustrative Procedure No. 2

3,4-Dimethoxy-1,2,5-thiadiazole 1-oxide

A solution of dimethyl oxaldiimidate (4.0 gm; 34.5 mmole) and pyridine (5.71 ml, 5.58 gm; 70.6 mmole) in 8 ml of $CH_2Cl_2$ was added dropwise to a cold solution of thionyl chloride (2.61 ml, 4.25 gm; 34.7 mmole) in 18 ml of $CH_2Cl_2$ under a stream of nitrogen, at such a rate that the reaction temperature remained between $0°$ and $15°$. After stirring at ambient temperature for 20 minutes, the reaction mixture was washed with two 11 ml portions of aqueous 0.055 N HCl. The aqueous phase was extracted with two 20 ml portions of $CH_2Cl_2$ and the combined organic phase was dried and evaporated to dryness under reduced pressure. The solid residue was recrystallized from isopropyl alcohol to give 3.0 gm of the title compound, mp $137°-139°$.

The compounds of Formula I may be prepared from a compound of Formula II by various alternative reaction schemes via several classes of novel intermediates.

Reaction Scheme 1

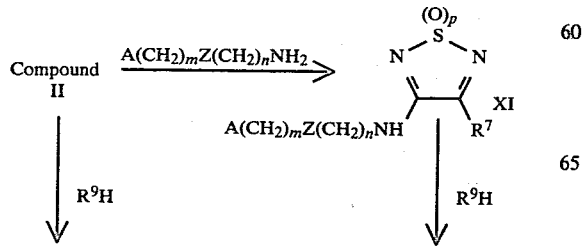

Reaction Scheme 1
-continued

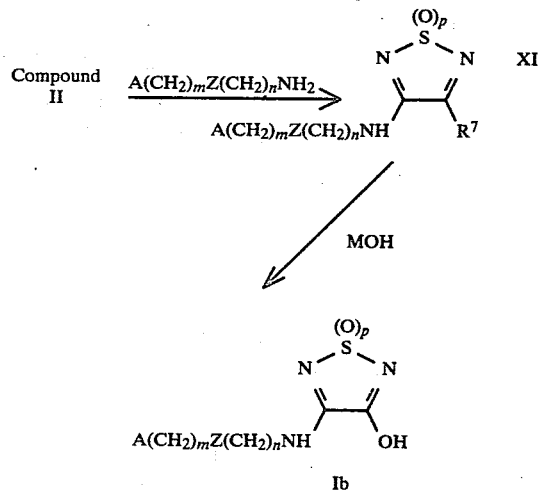

In reaction Scheme 1, $R^9$ may be $-NR^2R^3$ or $-NH(CH_2)_{n'}Z'(CH_2)_{m'}A'$. When $A'$, $Z'$, $m'$ and $n'$ are the same as A, Z, m and n, the reaction may, of course, be carried out in one step by reacting the compound of Formula II with two equivalents of $A(CH_2)_mZ(CH_2)_nNH_2$. The intermediates of Formula XI are all novel. The intermediates of Formula XII are novel except for the compound in which p is 2, $R^7$ is methoxy and $R^9$ is morpholino, that compound having been described in *J. Org. Chem.*, 40, 2743 (1975). The reactions are conducted in an inert organic solvent; we find methanol to be a convenient and readily available solvent. The reaction temperature is not critical. Most starting materials are quite reactive and we prefer to conduct the reaction at a temperature below room temperature, e.g. $0°-10°$. With some less reactive compounds it is convenient to conduct the reaction at room temperature. Sometimes it is desirable to subsequently raise the temperature of the reaction mixture (e.g. to $50°-60°$ C.) to complete the reaction.

Reaction Scheme 2

In Reaction Scheme 2, M is a metal cation which is preferably $K^+$, $Li^+$ or $Na^+$. The reaction conditions and solvents are as described for Reaction Scheme 1. All intermediates of Formula XI are novel compounds.

Reaction Scheme 3

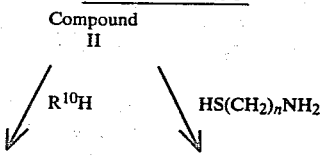

-continued
Reaction Scheme 3

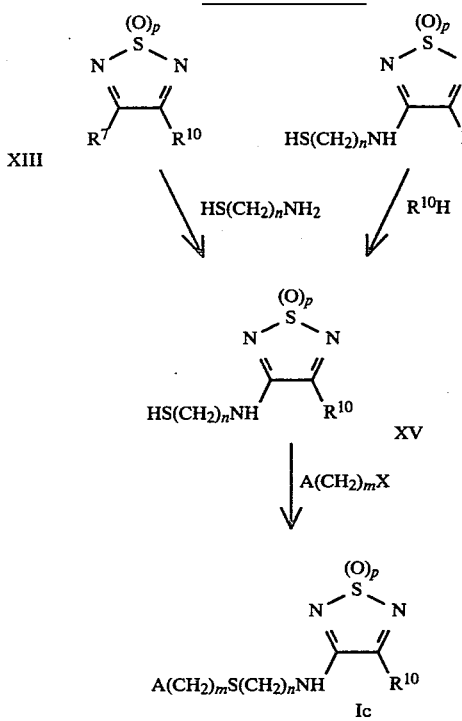

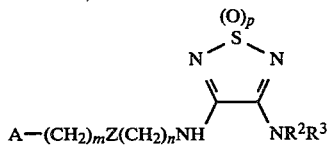

In Reaction Scheme 3, $R^{10}$ is $-NR^2R^3$ or $-NH(CH_2)_{n'}Z'(CH_2)_{m'}A'$, and X is a conventional leaving group. Suitable leaving groups include, for example, fluoro, chloro, bromo, iodo, $-O_3SR^{11}$ in which $R^{11}$ is (lower)alkyl [e.g. methanesulfonate], aryl or substituted aryl [e.g. benzenesulfonate, p-bromobenzenesulfonate or p-toluenesulfonate], $O_3SF$, acetoxy and 2,4-dinitrophenoxy. For convenience and economy we prefer to utilize a compound in which X is chloro. The reaction conditions for the preparation of the compounds of Formulae XIII, XIV and XV are as described for Reaction Scheme 1. The reaction of the compound of Formula XV with $A(CH_2)_mX$ may be conducted in any inert organic solvent such as an alkanol, acetonitrile, dimethylformamide, dimethylsulfoxide, acetone, or the like. We prefer to conduct the reaction in an alkanol such as methanol, ethanol or isopropanol. The reaction temperature is not critical; the reaction may be conducted at temperatures of from about 0° to about 200° C. At low temperatures the reaction is slow, while high temperatures normally lead to less pure products due to decomposition and the formation of side-products. We normally prefer to conduct the reaction at room temperature. The reaction of the compound of Formula XV with $A(CH_2)_mX$ to produce the compound of Formula Ic preferably is conducted in the presence of a base, which facilitates the reaction by acting as an acid acceptor. Suitable bases include, for example, NaOH, KOH, LiOH, triethylamine, dimethylaniline, sodium ethoxide and the like. Where X is hydroxyl, the reaction may be conducted in concentrated mineral acid, e.g. HCl (see Example 25). All intermediates of Formula XIII, XIV and XV are novel compounds.

In a preferred embodiment of the invention the compounds of Formula I have the structure

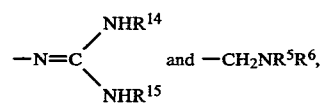

wherein p is 1 or 2;

$R^2$ and $R^3$ each are independently hydrogen, (lower)alkyl, (lower)alkenyl, (lower)alkynyl or cyclo(lower)alkyl(lower)alkyl, or, when $R^2$ is hydrogen, $R^3$ also may be pyridyl(lower)alkyl, substituted pyridyl(lower)alkyl wherein the pyridyl ring may contain one substituent selected from (lower)alkyl, (lower)alkoxy, hydroxy, amino and halogen, $A'-(CH_2)_{m'}Z'(CH_2)_{n'}-$, phenyl(lower)alkyl or 3,4-methylenedioxybenzyl;

m and m' each are independently zero or 1;

n and n' each are independently 2 or 3;

Z and Z' each are independently sulfur, oxygen or methylene;

A and A' each are independently phenyl, imidazolyl, thiazolyl, furyl, thienyl or pyridyl; provided that A and A' independently may contain one or two substituents, the first substituent being selected from (lower)alkyl, $$-N=C\begin{matrix}NHR^{14}\\ \\NHR^{15}\end{matrix} \quad \text{and} \quad -CH_2NR^5R^6,$$

and the second substituent being selected from (lower)alkyl;

$R^{14}$ and $R^{15}$ independently are hydrogen or (lower)alkyl, or $R^{14}$ and $R^{15}$, taken together, may be ethylene; and $R^5$ and $R^6$ each are independently hydrogen or (lower)alkyl; or $R^5$ and $R^6$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino;

or a nontoxic, pharmaceutically acceptable salt, hydrate, solvate or N-oxide thereof.

In another preferred embodiment of the invention the compounds of Formula I have the structure

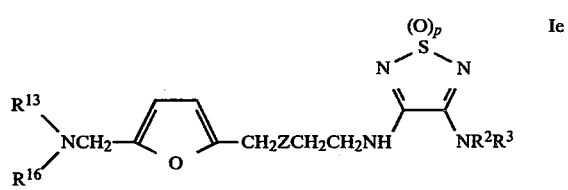

wherein p is 1 or 2; Z is sulfur or methylene; $R^2$ and $R^3$ each are independently hydrogen or (lower)alkyl, or, when $R^2$ is hydrogen, $R^3$ also may be (lower)alkenyl, (lower)alkynyl, phenyl(lower)alkyl, cyclo(lower)alkyl(lower)alkyl, pyridylmethyl or

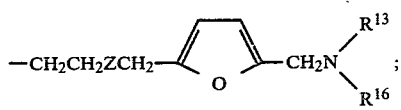

$R^{16}$ is methyl and $R^{13}$ is hydrogen or methyl, or $R^{16}$ and $R^{13}$, taken together with the nitrogen atom to which they are attached, may be piperidino; or a nontoxic pharmaceutically acceptable salt, hydrate, solvate or N-oxide thereof.

In another preferred embodiment of the invention the compounds of Formula I have the structure

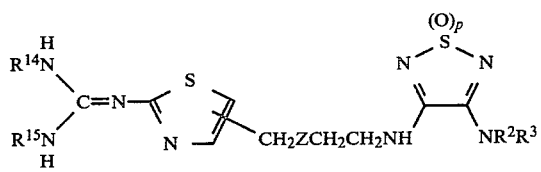

If wherein p is 1 or 2; Z is sulfur or methylene; $R^{14}$ and $R^{15}$ independently are hydrogen or methyl, or, $R^{14}$ and $R^{15}$, taken together, may be ethylene; and $R^2$ and $R^3$ each are independently hydrogen or (lower)alkyl, or, when $R^2$ is hydrogen, $R^3$ also may be (lower)alkenyl, (lower)alkynyl, pyridylmethyl,

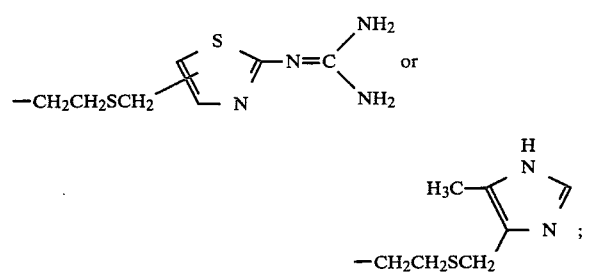

or a nontoxic pharmaceutically acceptable salt, hydrate, solvate or N-oxide thereof.

In another preferred embodiment of the invention the compounds of Formula I have the structure

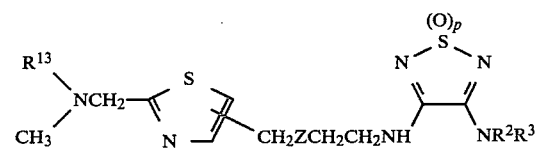

Ig wherein p is 1 or 2; Z is sulfur or methylene; $R^2$ and $R^3$ each are independently hydrogen or (lower)alkyl, or when $R^2$ is hydrogen, $R^3$ also may be (lower)alkenyl, (lower)alkynyl or

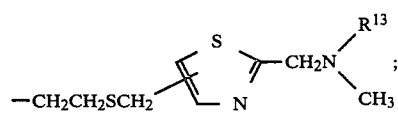

and $R^{13}$ is hydrogen or methyl; or a nontoxic pharmaceutically acceptable salt, hydrate, solvate or N-oxide thereof.

In another preferred embodiment of the invention the compounds of Formula I have the structure

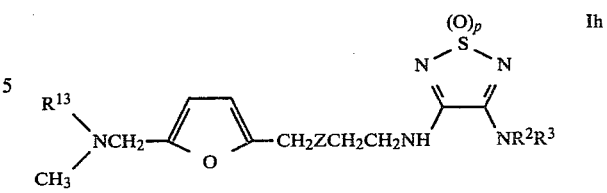

Ih wherein p is 1 or 2; Z is sulfur or methylene; $R^2$ and $R^3$ each are independently hydrogen or (lower)alkyl, or, when $R^2$ is hydrogen, $R^3$ also may be (lower)alkenyl, (lower)alkynyl, phenyl(lower)alkyl, pyridylmethyl, 3,4-methylenedioxybenzyl or

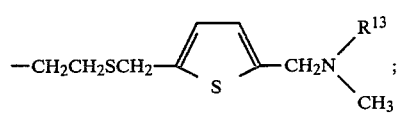

and $R^{13}$ is hydrogen or methyl; or a nontoxic pharmaceutically acceptable salt, hydrate, solvate or N-oxide thereof.

In another preferred embodiment of the invention the compounds of Formula I have the structure

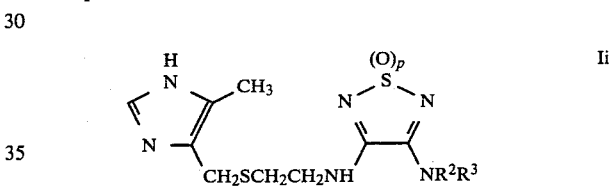

Ii wherein p is 1 or 2; and $R^2$ and $R^3$ each are independently hydrogen or (lower)alkyl, or, when $R^2$ is hydrogen, $R^3$ also may be (lower)alkenyl, (lower)alkynyl or

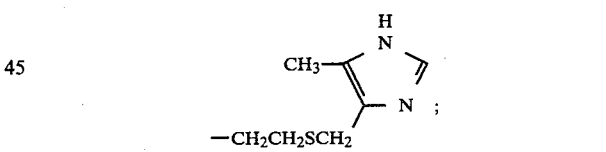

or a nontoxic pharmaceutically acceptable salt, hydrate, solvate or N-oxide thereof.

In another preferred embodiment of the invention the compounds of Formula I have the structure

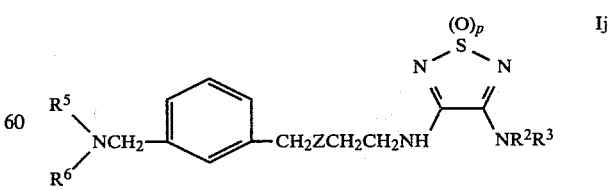

Ij wherein p is 1 or 2; Z is sulfur or methylene; $R^2$ and $R^3$ each are independently hydrogen or (lower)alkyl, or, when $R^2$ is hydrogen, $R^3$ also may be (lower)alkenyl, (lower)alkynyl or

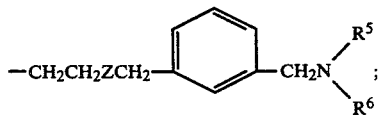

and $R^5$ and $R^6$ each are independently hydrogen or (lower)alkyl, or, $R^5$ and $R^6$, taken together with the nitrogen atom to which they are attached, may be piperidino; or a nontoxic, pharmaceutically acceptable salt, hydrate, solvate or N-oxide thereof.

In another preferred embodiment of the invention the compounds of Formula I have the structure

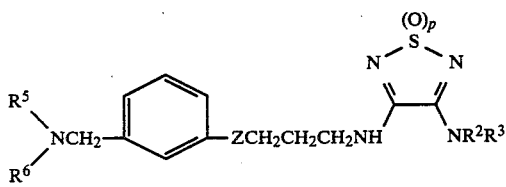

wherein p is 1 or 2; Z is oxygen or sulfur; $R^2$ and $R^3$ each are independently hydrogen or (lower)alkyl, or, when $R^2$ is hydrogen, $R^3$ may also be (lower)alkenyl, (lower)alkynyl, pyridylmethyl or

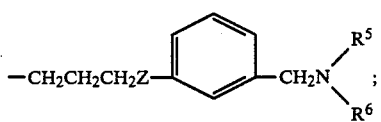

and $R^5$ and $R^6$ each are independently hydrogen or (lower)alkyl, or, when $R^5$ is hydrogen, $R^6$ also may be (lower)alkenyl or (lower)alkynyl; or $R^5$ and $R^6$, taken together with the nitrogen to which they are attached, may be pyrrolidino, methylpyrrolidino, morpholino, thiomorpholino, piperidino, methylpiperidino, dimethylpiperidino, homopiperidino or heptamethyleneimino; or a nontoxic pharmaceutically acceptable salt, hydrate, solvate or N-oxide thereof.

In another preferred embodiment of the invention the compounds of Formula I have the structure

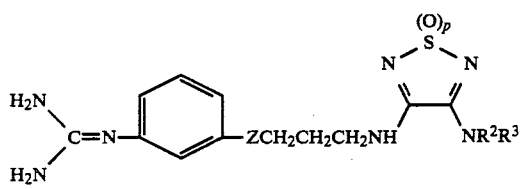

wherein p is 1 or 2; Z is oxygen or sulfur; $R^2$ and $R^3$ each are independently hydrogen or (lower)alkyl, or, when $R^2$ is hydrogen, $R^3$ may be (lower)alkenyl, (lower)alkynyl, pyridylmethyl or

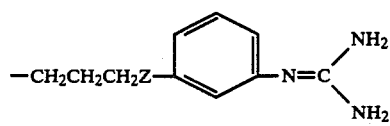

or a nontoxic pharmaceutically acceptable salt, hydrate, solvate or N-oxide thereof.

As presently envisaged, the particularly preferred compounds of this invention are (a) 3-{2-[(5-Dimethylaminomethyl-2-furyl)methylthio]ethylamino}-4-methylamino-1,2,5-thiadiazole 1,1-dioxide, (b) 3-{2-[(5-Dimethylaminomethyl-2-furyl)methylthio]ethylamino}-4-methylamino-1,2,5-thiadiazole 1-oxide, (c) 3-{2-[(5-Dimethylaminomethyl-2-furyl)methylthio]ethylamino}-4-ethylamino-1,2,5-thiadiazole 1-1-dioxide, (d) 3-{2-[(5-Dimethylaminomethyl-2-furyl)methylthio]ethylamino}-4-(n-propyl)amino-1,2,5-thiadiazole 1,1-dioxide, (e) 3-Allylamino-4-{2-[(5-dimethylaminomethyl-2-furyl)methylthio]ethylamino}-1,2,5-thiadiazole 1,1-dioxide, (f) 3-{2-[(5-Dimethylaminomethyl-2-furyl)methylthio]ethylamino}-4-(2-propynyl)amino-1,2,5-thiadiazole 1,1-dioxide;

(g) 3-{2-[(5-Dimethylaminomethyl-2-furyl)methylthio]ethylamino}-4-amino-1,2,5-thiadiazole 1,1-dioxide, (h) 3-{2-[(5-Dimethylaminomethyl-2-furyl)methylthio]ethylamino}-4-amino-1,2,5-thiadiazole 1-oxide, (i) 3-Amino-4-[3-(3-pyrrolidinomethylphenoxy)propylamino]-1,2,5-thiadiazole 1,1-dioxide, (j) 3-{4-(5-Dimethylamino-2-furyl)butylamino}-4-methylamino-1,2,5-thiadiazole 1,1-dioxide, (k) 3-Methylamino-4-[3-(3-pyrrolidinomethylphenoxy)propylamino]-1,2,5-thiadiazole 1,1-dioxide, (l) 3-{2-[(2-Guanidinothiazol-4-yl)methylthio]ethylamino}-4-methylamino-1,2,5-thiadiazole 1,1-dioxide, (m) 3-{2-[(2-Guanidinothiazol-4-yl)methylthio]ethylamino}-4-(2-propynyl)amino-1,2,5-thiadiazole 1,1-dioxide, (n) 3-Amino-4-[3-(3-pyrrolidinomethylphenoxy)propylamino]-1,2,5-thiadiazole 1-oxide, (o) 3-{2-[(2-Guanidinothiazol-4-yl)methylthio]ethylamino}-4-amino-1,2,5-thiadiazole 1,1-dioxide, (p) 3-{2-[(2-Dimethylaminomethyl-4-thiazolyl)methylthio]ethylamino}-4-methylamino-1,2,5-thiadiazole 1,1-dioxide, (q) 3-{2-[(5-Dimethylaminomethyl-2-thienyl)methylthio]ethylamino}-4-methylamino-1,2,5-thiadiazole 1,1-dioxide, (r) 3-{2-[(5-Dimethylaminomethyl-2-furyl)methylthio]ethylamino}-4-ethylamino-1,2,5-thiadiazole 1-oxide, (s) 3-Amino-4-{3-[3-(4-methylpiperidinomethyl)phenoxy]propylamino}-1,2,5-thiadiazole 1,1-dioxide, (t) 3-Amino-4-{2-[(2-guanidinothiazol-4-yl)methylthio]ethylamino}-1,2,5-thiadiazole 1-oxide, (u) 3-Benzylamino-4-{2-[(5-dimethylaminomethyl-2-furyl)methylthio]ethylamino}-1,2,5-thiadiazole 1,1-dioxide, (v) 3-{2-[(3-{Dimethylaminomethyl}phenyl)methylthio]ethylamino}-4-methylamino-1,2,5-thiadiazole 1,1-dioxide, (w) 3-Amino-4-{2-[(3-{dimethylaminomethyl}phenyl)methylthio]ethylamino}-1,2,5-thiadiazole 1-oxide, (x) 3-{2-[(5-Dimethylaminomethyl-2-thienyl)methylthio]ethylamino}-4-methylamino-1,2,5-thiadiazole 1-oxide, (y) 3-Amino-4-{4-(5-dimethylaminomethyl-2-furyl)butylamino}-1,2,5-thiadiazole 1,1-dioxide, (z) 3-Amino-4-{2-[(2-dimethylaminomethyl-4-thiazolyl)methylthio]ethylamino}-1,2,5-thiadiazole 1,1-dioxide, (aa) 3-Butylamino-4-{2-[(5-dimethylaminomethyl-2-furyl)methylthio]ethylamino}-1,2,5-thiadiazole 1,1-dioxide, (bb) 3-Cyclopropylmethylamino-4-{2-[(5-dimethylaminomethyl-2-furyl)methylthio]ethylamino}-1,2,5-thiadiazole 1,1-dioxide, (cc) 3-{2-[(5-Dimethylaminomethyl-2-furyl)methylthio]ethylamino}-4-[(2-pyridyl)methylamino]-1,2,5-thiadiazole 1,1-dioxide, (dd) 3-Amino-4-{3-[3-(4-methylpiperidinomethyl)phenoxy]propylamino}-1,2,5-thiadiazole 1-oxide, (ee) 4-{2-[(5-Dimethylaminomethyl-2-thienyl)methylthio]ethylamino}-3-(1-propylamino)-1,2,5-thiadiazole 1,1-dioxide, (ff) 3-{2-[(2-Guanidinothiazol-4-yl)methylthio]ethylamino}-4-methylamino-1,2,5-thiadiazole 1-oxide, (gg) 3-{3-[3-(hexamethyleneiminomethyl)phenoxy]propylamino}-4-methylamino-1,2,5-thiadiazole 1,1-dioxide, (hh) 3-[3-(3-dimethylaminomethylphenoxy)propylamino]-4-methylamino-1,2,5-thiadiazole 1,1-dioxide, (ii) 3-Amino-4-{3-[3-(hexamethyleneiminomethyl)phenoxy]propylamino}-1,2,5-thiadiazole 1-oxide, (jj) 4-{2-[(5-Dimethylaminomethyl-2-thienyl)methylthio]ethylamino}-3-(3-pyridyl)methylamino-1,2,5-thiadiazole 1,1-dioxide, (kk) 3-Amino-4-[3-(3-morpholinomethylphenoxy)propylamino]-1,2,5-thiadiazole 1,1-dioxide, (ll) 3-Methylamino-4-[3-(3-morpholinomethylphenoxy)propylamino]-1,2,5-thiadiazole 1,1-dioxide, (mm) 3-Amino-4-[3-(3-dimethylaminomethylphenoxy)propylamino]-1,2,5-thiadiazole 1-oxide, (nn) 3-Amino-4-{3-[3-(heptamethyleneiminomethyl)phenoxy]propylamino}-1,2,5-thiadiazole 1-oxide, (oo) 3-[(3-Pyridyl)methylamino]-4-[3-(3-piperidinomethylphenoxy)propylamino]-1,2,5-thiadiazole 1-oxide, (pp) 3-Amino-4-{2-[(2-{2-methylguanidino}thiazol-4-yl)methylthio]ethylamino}-1,2,5-thiadiazole 1-oxide, (qq) 3-Methylamino-4-[3-(3-piperidinomethylphenoxy)propylamino]-1,2,5-thiadiazole 1,1-dioxide, (rr) 3-Amino-4-[3-(3-piperidinomethylphenoxy)propylamino]-1,2,5-thiadiazole 1-oxide, (ss) 3-{2-[(5-Dimethylaminomethyl-2-thienyl)methylthio]ethylamino}-4-ethylamino-1,2,5-thiadiazole 1,1-dioxide, (tt) 3-Amino-4-[3-(3-piperidinomethylphenoxy)propylamino]-1,2,5-thiadiazole 1,1-dioxide, (uu) 3-Amino-4-[3-(3-guanidinophenoxy)propylamino]-1,2,5-thiadiazole 1-oxide.

In another aspect, this invention relates to novel starting materials having the formula

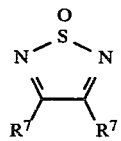

IIa in which each $R^7$ is a leaving group selected from halogen, (lower)alkyl, (lower)alkylthio and phenoxy or phenylthio which optionally contain 1 or 2 substituents selected from halogen, (lower)alkyl, (lower)alkoxy and nitro. In a preferred embodiment of the compounds of Formula IIa, each $R^7$ is (lower)alkoxy, phenoxy or substituted phenoxy; most preferably, each $R^7$ is methoxy.

In still another aspect, this invention relates to novel intermediates of the formula

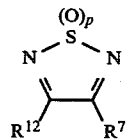

XVI wherein p is 1 or 2;

$R^7$ is a leaving group selected from halogen, (lower)alkoxy, (lower)alkylthio, phenoxy, phenylthio, substituted phenoxy and substituted phenylthio wherein the phenyl ring may contain 1 or 2 substituents selected from halogen, (lower)alkyl, (lower)alkoxy and nitro; and $R^{12}$ is $A(CH_2)_mZ(CH_2)_nNH-$, $R^2R^3N-$ or $HS(CH_2)_nNH-$; in which $R^2$ and $R^3$ each are independently hydrogen, (lower)alkyl, (lower)alkenyl, (lower)alkynyl, cyclo(lower)alkyl(lower)alkyl, hydroxy(lower)alkyl, (lower)alkoxy(lower)alkyl, (lower)alkylthio(lower)alkyl, 2-fluoroethyl, 2,2,2-trifluoroethyl or cyano(lower)alkyl, or, when $R^2$ is hydrogen, $R^3$ may also be cyclo(lower)alkyl, amino(lower)alkyl, (lower)alkylamino(lower)alkyl, di(lower)alkylamino(lower)alkyl, pyrrolidino(lower)alkyl, piperidino(lower)alkyl, morpholino(lower)alkyl, piperazino(lower)alkyl, pyridyl(lower)alkyl, substituted pyridyl(lower)alkyl wherein the pyridyl ring may contain one substituent selected from (lower)alkyl, (lower)alkoxy, hydroxy, amino and halogen, amino, (lower)alkylamino, di(lower)alkylamino, hydroxy, (lower)alkoxy, 2,3-dihydroxypropyl, cyano, amidino, (lower)alkylamidino, $A'-(CH_2)_{m'}Z'(CH_2)_{n'}-$, phenyl, phenyl(lower)alkyl, substituted phenyl or substituted phenyl(lower)alkyl, wherein the phenyl ring may contain one or two substituents independently selected from (lower)alkyl, hydroxy, (lower)alkoxy and halogen or one substituent selected from methylenedioxy, trifluoromethyl and di(lower)alkylamino; or $R^2$ and $R^3$, taken together, may be $-CH_2CH_2X(CH_2)_r-$;

r is an integer of from 1 to 3, inclusive;

X is methylene, sulfur, oxygen or $N-R^4$, provided that, when p is 2 and $R^7$ is methoxy, $R^2$ and $R^3$ taken together with the nitrogen to which they are attached, may not be morpholino, and that, when r is 1, X is methylene;

$R^4$ is hydrogen, (lower)alkyl, (lower)alkenyl, (lower)alkynyl, (lower)alkanoyl or benzoyl;

m and m' each are independently an integer of from zero to 2, inclusive;

n and n' each are independently an integer of from 2 to 4, inclusive;

Z and Z' each are independently sulfur, oxygen or methylene;

A and A' each are independently phenyl, imidazolyl, thiazolyl, isothiazolyl, oxazolyl, isoxazolyl, triazolyl, thiadiazolyl, oxadiazolyl, furyl, thienyl or pyridyl; provided that A and A' independently may contain one or two substituents, the first substituent being selected from (lower)alkyl, hydroxy, trifluoromethyl, halogen, amino, hydroxymethyl, (lower-)alkoxy,

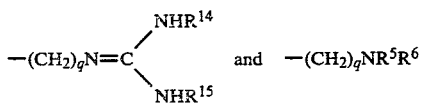

and the second substituent being selected from (lower)alkyl, hydroxy, trifluoromethyl, halogen, amino, hydroxymethyl and (lower)alkoxy;

q is an integer of from 0 to 6, inclusive;

$R^{14}$ and $R^{15}$ independently are hydrogen or (lower)alkyl, or if $R^{14}$ is hydrogen, $R^{15}$ also may be (lower)alkanoyl or benzoyl, or $R^{14}$ and $R^{15}$, taken together, may be ethylene; and $R^5$ and $R^6$ each are independently hydrogen, (lower)alkyl, (lower)alkenyl, (lower)alkynyl, (lower)alkoxy(lower)alkyl, cyclo(lower)alkyl, phenyl or phenyl(lower)alkyl, provided that $R^5$ and $R^6$ may not both be cyclo(lower)alkyl or phenyl; or $R^5$ and $R^6$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino;

or a salt, hydrate, solvate or N-oxide thereof.

In a more preferred embodiment of the compounds of Formula XVI, $R^{12}$ is $A(CH_2)_mZ(CH_2)_nNH$—in which A is phenyl, imidazolyl, thiazolyl, furyl, thienyl or pyridyl, each of which may contain one or two substituents, the first substituent being selected from (lower)alkyl,

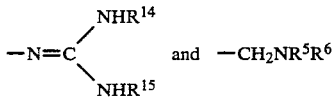

and the second substituent being selected from (lower)alkyl; Z is sulfur, oxygen or methylene; m is zero or one; n is two or three; $R^{14}$ and $R^{15}$ independently are hydrogen or (lower)alkyl, or $R^{14}$ and $R^{15}$, taken together, may be ethylene; $R^5$ and $R^6$ each are independently hydrogen or (lower)alkyl; or $R^5$ and $R^6$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino; and $R^7$ is (lower)alkoxy.

In another more preferred embodiment of the compounds of Formula XVI, $R^{12}$ is $R^2R^3N$— in which $R^2$ and $R^3$ each are independently hydrogen, (lower)alkyl, (lower)alkenyl, (lower)alkynyl or cyclo(lower)alkyl(lower)alkyl, or, when $R^2$ is hydrogen, $R^3$ also may be pyridyl(lower)alkyl, substituted pyridyl(lower)alkyl wherein the pyridyl ring may contain one substituent selected from (lower)alkyl, (lower)alkoxy, hydroxy, amino and halogen, $A'(CH_2)_{m'}Z'(CH_2)_{n'}$—, phenyl(lower)alkyl or 3,4-methylenedioxybenzyl; m' is zero or one, n' is two or three, Z' is sulfur, oxygen or methylene; A' is phenyl, imidazolyl, thiazolyl, furyl, thienyl or pyridyl, each of which may contain one or two substituents, the first substituent being selected from (lower)alkyl,

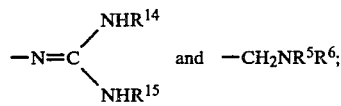

and the second substituent being selected from (lower)alkyl; $R^{14}$ and $R^{15}$ independently are hydrogen or (lower)alkyl, or $R^{14}$ and $R^{15}$, taken together, may be ethylene; $R^5$ and $R^6$ each are independently hydrogen or (lower)alkyl; or $R^5$ and $R^6$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino; and $R^7$ is (lower)alkoxy. In a particularly preferred embodiment, the compound is 3-amino-4-methoxy-1,2,5-thiadiazole 1-oxide.

In another more preferred embodiment of the compounds of Formula XVI, $R^{12}$ is $HS(CH_2)_nNH$—; in which n is an integer of from two to four and $R^7$ is (lower)alkoxy.

In a particularly preferred embodiment of the compounds of Formula XVI, $R^{12}$ is

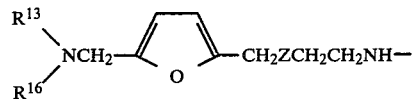

in which Z is sulfur or methylene, $R^{16}$ is methyl and $R^{13}$ is hydrogen or methyl, or $R^{16}$ and $R^{13}$, taken together with the nitrogen atom to which they are attached, may be piperidino; and $R^7$ is (lower)alkoxy.

In another particularly preferred embodiment of the compounds of Formula XVI, $R^{12}$ is

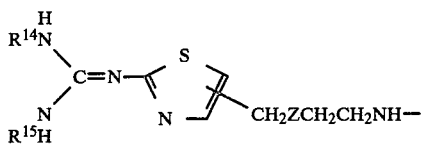

in which Z is sulfur or methylene; $R^{14}$ and $R^{15}$ independently are hydrogen or methyl, or $R^{14}$ and $R^{15}$, taken together, may be ethylene; and $R^7$ is (lower)alkoxy.

In another particularly preferred embodiment of the compounds of Formula XVI, $R^{12}$ is

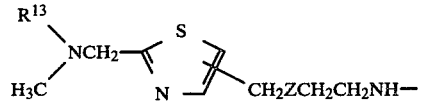

in which $R^{13}$ is hydrogen or methyl; Z is sulfur or methylene; and $R^7$ is (lower)alkoxy.

In another particularly preferred embodiment of the compounds of Formula XVI, $R^{12}$ is

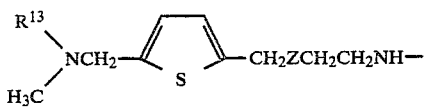

in which R[13] is hydrogen or methyl; Z is sulfur or methylene; and R[7] is (lower)alkoxy.

In another particularly preferred embodiment of the compounds of Formula XVI, R[12] is

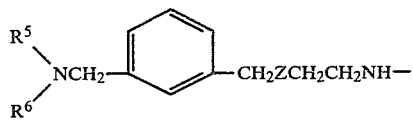

in which R[5] and R[6] each are independently hydrogen or (lower)alkyl, or, R[5] and R[6], taken together with the nitrogen atom to which they are attached, may be piperidino; Z is sulfur or methylene; and R[7] is (lower)alkoxy.

In another particularly preferred embodiment of the compounds of Formula XVI, R[12] is

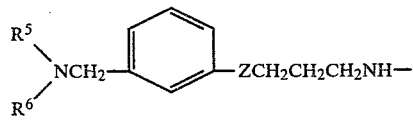

in which Z is oxygen or sulfur; R[5] and R[6] each are independently hydrogen or (lower)alkyl, or, when R[5] is hydrogen, R[6] also may be (lower)alkenyl or (lower)alkynyl; or R[5] and R[6], taken together with the nitrogen to which they are attached, may be pyrrolidino, methylpyrrolidino, morpholino, thiomorpholino, piperidino, methylpiperidino, dimethylpiperidino, homopiperidino or heptamethyleneimino; and R[7] is (lower)alkoxy.

In another particularly preferred embodiment of the compounds of Formula XVI, R[12] is

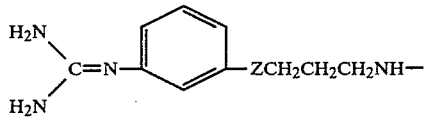

in which Z is oxygen or sulfur; and R[7] is (lower)alkoxy.

In still another aspect, this invention relates to novel intermediates of the formula

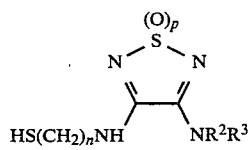

XVII wherein
p is 1 or 2;
n is an integer of from 2 to 4, inclusive;
R[2] and R[3] each are independently hydrogen, (lower)alkyl, (lower)alkenyl, (lower)alkynyl, cyclo(lower)alkyl(lower)alkyl, hydroxy(lower)alkyl, (lower)alkoxy(lower)alkyl, (lower)alkylthio(lower)alkyl, 2-fluoroethyl, 2,2,2-trifluoroethyl or cyano(lower)alkyl, or, when R[2] is hydrogen, R[3] may also be cyclo(lower)alkyl, amino(lower)alkyl, (lower)alkylamino(lower)alkyl, di(lower)alkylamino(lower)alkyl, pyrrolidino(lower)alkyl, piperidino(lower)alkyl, morpholino(lower)alkyl, piperazino(lower)alkyl, pyridyl(lower)alkyl, substituted pyridyl(lower)alkyl wherein the pyridyl ring may contain one substituent selected from (lower)alkyl, (lower)alkoxy, hydroxy, amino and halogen, amino, (lower)alkylamino, di(lower)alkylamino, hydroxy, (lower)alkoxy, 2,3-dihydroxypropyl, cyano, amidino, (lower)alkylamidino, A'—(CH$_2$)$_{m'}$Z'(CH$_2$)$_{n'}$—, phenyl, phenyl(lower)alkyl, substituted phenyl or substituted phenyl(lower)alkyl, wherein the phenyl ring may contain one or two substituents independently selected from (lower)alkyl, hydroxy, (lower)alkoxy and halogen or one substituent selected from methylenedioxy, trifluoromethyl and di(lower)alkylamino; or R[2] and R[3], taken together, may be —CH$_2$CH$_2$X(CH$_2$)$_r$—;

r is an integer of from 1 to 3, inclusive;
X is methylene, sulfur, oxygen or N-R[4], provided that, when r is 1, X is methylene;
R[4] is hydrogen, (lower)alkyl, (lower)alkenyl, (lower)alkynyl, (lower)alkanoyl or benzoyl;
m' is an integer of from zero to 2, inclusive;
n' is an integer of from 2 to 4, inclusive;
Z' is sulfur, oxygen or methylene;
A' is phenyl, imidazolyl, thiazolyl, isothiazolyl, oxazolyl, isoxazolyl, triazolyl, thiadiazolyl, oxadiazolyl, furyl, thienyl or pyridyl; provided that A' may contain one or two substituents, the first substituent being selected from (lower)alkyl, hydroxy, trifluoromethyl, halogen, amino, hydroxymethyl, (lower)alkoxy,

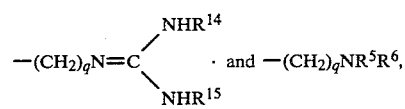

and the second substituent being selected from (lower)alkyl, hydroxy, trifluoromethyl, halogen, amino, hydroxymethyl and (lower)alkoxy;
q is an integer of from 0 to 6, inclusive;
R[14] and R[15] independently are hydrogen or (lower)alkyl, or, if R[14] is hydrogen, R[15] also may be (lower)alkanoyl or benzoyl, or R[14] and R[15], taken together, may be ethylene; and
R[5] and R[6] each are independently hydrogen, (lower)alkyl, (lower)alkenyl, (lower)alkynyl, (lower)alkoxy(Lower)alkyl, cyclo(lower)alkyl, phenyl or phenyl(lower)alkyl, provided that R[5] and R[6] may not both be cyclo(lower)alkyl or phenyl; or R[5] and R[6], taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino; or a salt, hydrate, solvate or N-oxide thereof.

In a more preferred embodiment of the compounds of Formula XVII, R[2] and R[3] each are independently hydrogen, (lower)alkyl, (lower(alkenyl, (lower)alkynyl or cyclo(lower)alkyl(lower)alkyl, or, when R[2] is hydrogen, R[3] also may be pyridyl(lower)alkyl, substituted pyridyl(lower)alkyl wherein the pyridyl ring may contain one substituent selected from (lower)alkyl, (lower)alkoxy, hydroxy, amino and halogen, A'—(CH$_2$)$_{m'}$Z'(CH$_2$)$_{n'}$—, phenyl(lower)alkyl or 3,4-methylenedioxybenzyl; m' is an integer of from zero to two inclusive; n and n' each are independently an integer of from 2 to 4, inclusive; Z' is sulfur, oxygen or methylene; A' is phenyl, imidazolyl, thiazolyl, furyl, thienyl or pyridyl, each of which may contain one or two substituents, the first substituent being selected from (lower)alkyl,

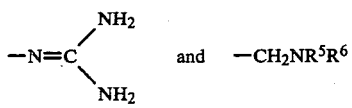

and the second substituent being selected from (lower)alkyl; and R$^5$ and R$^6$ each are independently hydrogen or (lower)alkyl.

In another more preferred embodiment of the compounds of Formula XVII, n is 2; R$^2$ and R$^3$ each are independently selected from hydrogen, (lower)alkyl, (lower)alkenyl, (lower)alkynyl and phenyl(lower)alkyl, or, when R$^2$ is hydrogen, R$^3$ may be

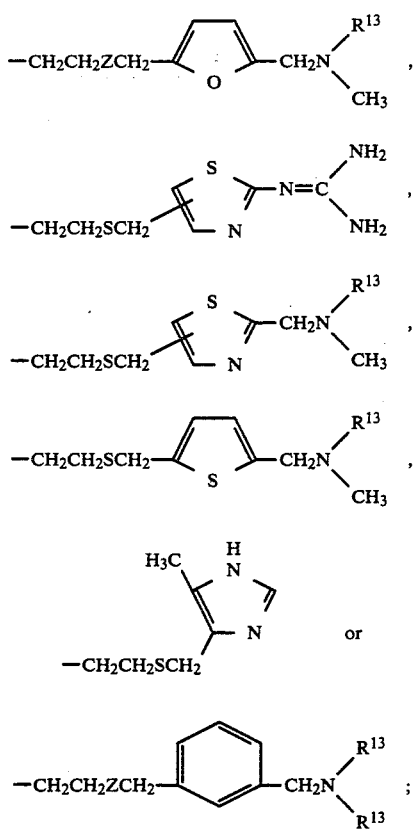

in which Z is sulfur or methylene and R$^{13}$ is hydrogen or methyl.

In another more preferred embodiment of the compounds of Formula XVII, n is 2; R$^2$ is hydrogen; and R$^3$ is

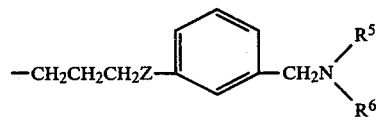

in which Z is oxygen or sulfur; R$^5$ and R$^6$ each are independently hydrogen or (lower)alkyl, or, when R$^5$ is hydrogen, R$^6$ also may be (lower)alkenyl or (lower)alkynyl; or R$^5$ and R$^6$, taken together with the nitrogen to which they are attached, may be pyrrolidino, morpholino, piperidino or homopiperidino.

In another more preferred embodiment of the compounds of Formula XVII, n is 2; R$^2$ is hydrogen and R$^3$ is

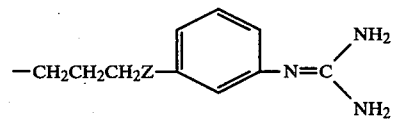

in which Z is oxygen or sulfur.

As used herein, the term nontoxic pharmaceutically acceptable salt means the salt of a compound of Formula I with a nontoxic pharmaceutically acceptable organic or inorganic acid. Such acids are well known and include hydrochloric, hydrobromic, sulfuric, sulfamic, phosphoric, nitric, maleic, fumaric, succinic, oxalic, benzoic, methanesulfonic, ethanedisulfonic, benzenesulfonic, acetic, propionic, tartaric, citric, camphorsulfonic, and the like. The salts are made by methods known in the art. It will be appreciated by those skilled in the art that some of the compounds of Formula I and intermediates disclosed herein will form di-salts, tri-salts, etc. It is also to be understood that salts of the intermediates are not limited to salts with nontoxic pharmaceutically acceptable acids when such intermediates are not themselves used as medicaments.

We have found that many of the compounds of Formula I produced herein tenaciously hold solvents from which they are crystallized. In some cases it appears that the products are true solvates, while in other cases the products may merely retain adventitious solvent or be a mixture of solvate plus some adventitious solvent. Although the solvent can be removed by drying at elevated temperature, this often changed a nicely crystalline product into a gummy solid. Because the solvated products usually had quite sharp melting points, our usual practice was to dry the products at room temperature. Where solvent was retained even after lengthy drying, the amount of solvent was determined, such as by NMR. The Examples below give the amount of solvent (where appropriate) and the analyses and melting points are those of the solvated product unless otherwise specified.

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of this invention will depend not only on such factors as the weight of the patient, but also on the degree of gastric acid inhibition desired and the potency of the particular compound being utilized. The decision as to the particular dosage to be employed is within the discretion of the physician. In the Two Hour Pylorus Ligated Rat test described below, cimetidine has an $ED_{50}$ of approximately 9 μmoles/kg. The usual human adult dosage of cimetidine is 300 mg, given four times a day. The usual human adult starting dosages of the compounds of this invention are readily determined from their $ED_{50}$ in this same test. Thus, if the $ED_{50}$ is 0.9 μmoles, the usual starting dosage would be approximately 30 mg, given four times a day. With an $ED_{50}$ of 0.09 μmoles/kg, the usual starting dosage would be approximately 3 mg, given four times a day, etc. These starting dosages (and the number of times administered per day) may, of course, be varied by titration of the dosage to the particular circumstances of the specific patient. With the preferred compounds of this invention, each dosage unit will contain the active ingredient in an amount of from about 0.5 mg to about 150 mg, and most preferably from about 2 mg to about 50 mg. The active ingredient will preferably be administered in equal doses from two to four times a day. The daily dosage regimen will preferably be from 1 mg to about 600 mg, and most preferably from about 4 mg to about 200 mg.

Histamine $H_2$-receptor antagonists have been shown to be effective inhibitors of gastric secretion in animals and man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al., *Lancet*, 1, 8001 (1977). One of the standard animal models for determining gastric antisecretory activity of histamine $H_2$-antagonists is the pylorus ligated rat. Table 1, below, gives the gastric antisecretory $ED_{50}$ (in μmoles/kg.) in the pylorus ligated rat for many of the compounds of this invention.

Determination of Gastric Antisecretory Activity in the Two Hour Pylorus Ligated (Shay) Rat The pyloric ligation procedure in the rat was designed by Shay et al., *Gastroenterology*, 5, 53 (1945) for the study of perforating gastric ulcers; however, as the method became known, it was also employed as a means of studying rat gastric secretion, Shay et al., *Gastroenterology*, 26, 906 (1954), Brodie, D, A. *Am. J. Dig. Dis.*, 11, 231 (1966). A modification of this procedure is presently used to evaluate compounds for gastric antisecretory activity.

Male Long Evans rats, 280–300 gm., are used. The animals are placed in individual cages and fasted for 24 hours with free access to water. Under ether anesthesia, the stomach is reached through a midline incision, and a cotton-thread ligature is placed around the pylorus. After wound closure, ether administration is stopped and the test compound or control vehicle is administered either intraperitoneally or subcutaneously in a volume of 1 ml./kg. All compounds are solubilized with one equivalent of HCl and brought to the proper volume with water. The animals are returned to their cages from which the water bottles have been removed and two hours later are sacrificed with ether. The stomach is removed and the two hour gastric collection is drained into a graduated test tube for volume determination. Titratable acidity is measured by titrating a one ml. sample to pH 7.0 with 0.02 NaOH, using an Autoburet and electrometric pH meter (Radiometer). Titratable acid output is calculated in microequivalents by multiplying the volume in milliliters by the acid concentration in milliequivalents per liter. The percent inhibition of acid output is calculated as follows $$\% \text{ Inhibition of Acid Output} = \frac{\text{Acid Output (Control)} - \text{Acid Output (Drug)}}{\text{Acid Output (Control)}} \times 100$$

At least five rats are used at each dosage level, and a minimum of three dosage levels are utilized for determination of a dose response curve. Initially this test was conducted utilizing intraperitoneal injection of the test compound or control vehicle. However, it was subsequently found that the test was somewhat more sensitive when subcutaneous injections were utilized, and all subsequent tests were conducted via the subcutaneous route. The route of administration of each compound is noted in Table 1.

TABLE 1

Effect of Compounds of this Invention on Gastric Acid Output in the Two Hour Pylorus Ligated Rat

| Compound of Example No. | Route or Administration | $ED_{50}$* μmoles/kg. | |
|---|---|---|---|
| 1 | i.p. | 12.5 | (4.90–33.0) |
| 2 | s.c. | ~100 | |
| 3 | i.p. | 0.46 | (0.26–0.74) |
| 7 | i.p. | 31.1 | (11.1–82.8) |
| 11 B | i.p. | 0.69 | (0.31–1.33) |
| 11 C | s.c. | 0.20 | (0.03–2.9) |
| 12 | i.p. | 0.28 | (0.11–0.69) |
| 13 | s.c. | 0.46 | (0.02–3.1) |
| 14 | s.c. | ~25 | |
| 17 | s.c. | 33 | (8.7–141) |
| 18 | s.c. | 0.38 | (0.02–5.33) |
| 19 | s.c. | 0.34 | (0.15–0.81) |
| 20 A | s.c. | 1.15 | (0.32–3.7) |
| 21 | s.c. | 0.30 | (0.09–1.0) |
| 28 | s.c. | 1.39 | (0.39–4.91) |
| 31 | i.p. | 0.41 | (0.19–0.81) |
| 32 | i.p. | 0.08 | (0.03–0.15) |
| 33 | s.c. | 0.57 | (0.16–1.84) |
| 35 | s.c. | 0.08 | (0.02–0.22) |
| 36 | s.c. | 1.59 | (0.48–6.46) |
| 51 | s.c. | 55 | (8.8–930) |
| 52 | s.c. | ~350 | |
| 65 | s.c. | 0.07 | (0.02–0.32) |
| 84 | s.c. | 0.15 | (0.02–0.53) |
| 85 | s.c. | 0.14 | (0.05–0.41) |
| 86 | s.c. | 0.04 | (0.015–0.12) |
| 87 | s.c. | 0.02 | (0.006–0.04) |
| 88 | s.c. | 0.08 | (0.04–0.22) |
| 89 | s.c. | 0.25 | (0.07–0.84) |
| 90 | s.c. | 0.86 | (0.24–2.69) |
| 91 | s.c. | 1.3 | (0.36–3.9) |
| 92 | s.c. | 0.24 | (0.09–0.71) |
| 93 | s.c. | 0.14 | (0.07–0.32) |
| 94 | s.c. | 0.44 | (0.08–1.9) |
| 95 | s.c. | ~15 | |
| 96 | s.c. | ~15 | |
| 97 | s.c. | ~3 | |
| 98 | s.c. | 0.52 | (0.08–2.33) |
| 99 | s.c. | 32 | 5.7–200) |

TABLE 1-continued
Effect of Compounds of this Invention on Gastric Acid Output in the Two Hour Pylorus Ligated Rat

| Compound of Example No. | Route or Administration | $ED_{50}$* $\mu$moles/kg. | |
|---|---|---|---|
| 100 | s.c. | 1.6 | (0.38–5.5) |
| 101 | s.c. | 68 | (10–750) |
| 102 | s.c. | ~15 | |
| 103 | s.c. | 0.54 | (0.21–1.4) |
| 104 | s.c. | 0.61 | (0.15–1.88) |
| 105 | s.c. | 1.65 | (0.45–4.45) |
| 106 | s.c. | ~80 | |
| 107 | s.c. | 23 | (5.1–110) |
| 108 | s.c. | 2.2 | (0.54–8.9) |
| 109 | s.c. | 1.4 | (0.51–3.9) |
| 110 | s.c. | 0.05 | (0.03–0.14) |
| 111 | s.c. | 0.64 | (0.17–2.5) |
| 112 | s.c. | 1.2 | (0.47–2.9) |
| 113 | s.c. | 0.07 | (0.03–0.14) |
| 114 | s.c. | ~15 | |
| 115 | s.c. | 0.57 | (0.20–1.6) |
| 116 | s.c. | >10 | |
| 117 | s.c. | ~0.5 | |
| 118 | s.c. | 0.066 | (0.018–0.19) |
| 119 | s.c. | >10 | |
| 120 | s.c. | ~5 | |
| 121 | s.c. | 0.19 | (0.055–0.56) |
| 122 | s.c. | ~10.0 | |
| 123 | s.c. | >10 | |
| 124 | s.c. | >10 | |
| 125 | s.c. | ~10 | |
| 127 | s.c. | >10 | |
| 128 | s.c. | ~10 | |
| 129 | s.c. | ~1 | |
| 130 | s.c. | 2.3 | (0.79–14) |
| 131 | s.c. | ~0.5 | |
| 132 | s.c. | 0.025 | (0.007–0.069) |
| 133 | s.c. | 0.061 | (0.019–0.24) |
| 134 | s.c. | 0.024 | (0.011–0.050) |
| 135 | s.c. | 0.57 | (0.29–1.12) |
| 144 a | s.c. | 0.095 | (0.033–0.30) |
| 144 b | s.c. | 0.025 | (0.0087–0.065) |
| 144 c | s.c. | 0.14 | (0.034–0.44) |
| 144 d | s.c. | 0.91 | (0.36–3.2) |
| 145 a | s.c. | 0.056 | (0.021–0.18) |
| 145 b | s.c. | ~0.06 | |
| 145 c | s.c. | 0.025 | (0.0098–0.057) |
| 145 d | s.c. | 0.05 | (0.005–0.2) |
| 146 a | s.c. | 0.023 | (0.0091–0.046) |
| 146 d | s.c. | 0.28 | (0.66–1.21) |
| 149 | s.c. | ~0.08 | |
| 151 | s.c. | 0.9 | (0.15–3.5) |

*Numbers in parentheses are the 95% confidence limits

Some of the compounds of this invention were also tested, and showed activity, in the Isolated Guinea Pig Right Atria Test, in the Gastric Fistula Dog Test (intravenous) and the Heidenhain Pouch Dog Test (oral). The first two tests were conducted according to the procedures described in our colleagues U.S. Pat. No. 4,112,234. The Heidenhain Pouch Dog Test followed the general procedure of Grossman and Konturek, *Gastroenterology*, 66, 517 (1974).

Celite is a registered trademark of the Johns-Manville Products Corporation for diatomaceous earth. Skellysolve B is a registered trademark of the Skelly Oil Company for a petroleum ether fraction boiling at 60°–68°, consisting essentially of n-hexane.

The term "flash chromatography" used in some of the Examples refers to a relatively new chromatographic technique described by W. C. Still et al. in *J. Org. Chem.*, 43, 2923–2925 (1978). It utilizes more finely divided chromatographic media and pressures somewhat above atmospheric pressure, to give faster chromatographic separations.

In the following examples, all temperatures are given in degrees Centigrade.

EXAMPLE 1

3-{2-[(5-Methyl-1H-imidazol-4-yl)methylthio]ethylamino}-4-(2-propynyl)amino-1,2,5-thiadiazole 1,1-dioxide A. 3-{2-[(5-Methyl-1H-imidazol-4-yl)methylthio]ethylamino}-4-methoxy-1,2,5-thiadiazole 1,1-dioxide To a well stirred suspension of 3,4-dimethoxy-1,2,5-thiadiazole 1,1-dioxide (2.0 g; 11.2 mmoles) [prepared according to the procedure described in *J. Org. Chem.*, 40, 2743 (1975)] in 200 ml of methanol at ambient temperature was added a solution of 2-[(5-methyl-1H-imidazol-4-yl)methylthio]ethylamine (from the dihydrochloride, 2.73 g; 11.2 mmoles) [prepared according to Belgian Patent 779,775] in 25 ml of methanol. After stirring for 30 minutes, a methanolic solution of the title compound was produced. The TLC [Silica/$CH_2Cl_2$:$CH_3OH$ (90:10)] gave Rf=0.44.

B. 3-{2-[(5-Methyl-1H-imidazol-4-yl)methylthio]ethylamino}-4-(2-propynyl)amino-1,2,5-thiadiazole 1,1-dioxide To the methanolic solution of the product of Step A was added 7 ml of 2-propynylamine. After stirring at ambient temperature for 20 minutes, the reaction mixture was evaporated under reduced pressure, and the residual oil was placed on silica gel and chromatographed by gradient elution using methylene chloride-methanol. The appropriate fractions were combined to yield 2.74 g of the title compound as an oil.

An additional purification was achieved by combining the above material with that obtained in an identical second experiment and the mixture placed on silica gel and chromatographed by gradient elution using methylene chloride-methanol. The appropriate fractions were combined with methanol and evaporated under reduced pressure to yield the title compound (2.93 g) as a friable solid, mp 82°–103°; the NMR spectrum (100 MHz) in $d_6$ dimethyl sulfoxide showed the presence of ⅓ mole of methanol.

Anal. Calcd for $C_{12}H_{16}N_6O_2S_2 \cdot \frac{1}{3}CH_3OH$: C, 42.19; H, 4.97; N, 23.95; S, 18.27. Found: C, 42.05; H, 5.05; N, 24.01; S, 18.45.

EXAMPLE

3-{2-[(5-Methyl-1H-imidazol-4-yl)methylthio]ethylamino}-4-methylamino-1,2,5-thiadiazole 1,1-dioxide To a well stirred suspension of 3,4-dimethoxy-1,2,5-thiadiazole 1,1-dioxide (2.5 g; 14.0 mmoles) in 250 ml of dry methanol that had been cooled to 2° in an ice-water bath was added dropwise over a period of 25 minutes a solution of 2-[(5-methyl-1-H-imidazol-4-yl)methylthio]ethylamine (from the dihydrochloride, 3.42 g; 14.0 mmoles) in 25 ml of methanol. After stirring at 2° for 20 minutes, anhydrous methylamine was bubbled into the solution for 6 minutes and stirring was continued at ambient temperature for 30 minutes. The reaction mixture was evaporated under reduced pressure and the residue was placed on 50 g of silica gel and chromatographed by gradient elution using methylene chloride-methanol. The appropriate fractions were combined to give 3.2 g of the title compound. Additional purification of the product using column chromatography gave an analytical sample of the title compound as an amorphous solid, mp 98°–110°. The NMR spectrum (100

MHz) in $d_6$ dimethyl sulfoxide gave the following resonances δ: 7.46 (s, 1H); 3.70 (s, 2H); 2.53 (t, 2H); 2.86 (s, 3H); 2.72 (t, 2H); 2.15 (s, 3H).

Anal. Calcd. for $C_{10}H_{16}N_6O_2S_2$: C, 37.96; H, 5.09; N, 26.56; S, 20.27. Found (corr. for 1.60% $H_2O$): C, 37.79; H, 5.16; N, 26.52; S, 20.24.

EXAMPLE 3

3-{2-[(2-Guanidinothiazol-4-yl)methylthio]ethylamino}-4-{2-[(5-methyl-1H-imidazol-4-yl)methylthio]ethylamino}-1,2,5-thiadiazole 1,1-dioxide To a well stirred solution at −10° of 3-{2-[(5-methyl-1H-imidazol-4-yl)methylthio]ethylamino}-4-methoxy-1,2,5-thiadiazole 1,1-dioxide [prepared from the dihydrochloride of 2-{(5-methyl-1H-imidazol-4-yl)methylthio}ethylamine (2.73 g; 11.2 mmole) by the procedure of Step A of Example 1] was rapidly added a solution of 2-[(2-quanidinothiazol-4-yl)methylthio]ethylamine (from the dihydrochloride, 3.41 g; 11.2 mmoles) [prepared according to the procedure described in South African Patent 78/2129] in 35 ml of methanol. After stirring at −10° for 30 minutes, the solution was allowed to warm to ambient temperature. The reaction mixture was evaporated under reduced pressure and the residue was placed on 45 g of silica gel and chromatographed using 1 liter of methylene chloride-methanol (4:1). The appropriate fractions were combined and evaporated, and the residue (5.82 g) was placed on 80 g of aluminum oxide and chromatographed using a gradient elution of ethyl acetate-methanol. The appropriate fractions were combined, filtered through Celite and evaporated under high vacuum to yield the title compound (2.5 g) as an amorphous solid containing approximately ⅔ mole of ethyl acetate, as ascertained by the NMR spectrum (100 MHz) in $d_6$ dimethyl sulfoxide.

Anal. Calcd for $C_{16}H_{24}N_{10}O_2S_4 \cdot \frac{2}{3}C_4H_8O_2$: C, 38.96; H, 5.14; N, 24.34; S, 22.29. Found: C, 39.08; H, 4.96; N, 24.48; S, 22.26.

EXAMPLE 4

3-{2-[(5-Methyl-1H-imidazol-4-yl)methylthio]ethylamino}-4-methylamino-1,2,5-thiadiazole 1-oxide A. 3,4-Dimethoxy-1,2,5-thiadiazole 1-oxide A solution of 3,4-dimethoxy-1,2,5-thiadiazole (35.2 g; 24.1 mmoles) [prepared according to the procedure described in *J. Org. Chem.*, 40, 2749 (1975)] in 100 ml of chloroform was added over a period of 3 minutes to a stirred solution of m-chloroperbenzoic acid (50.7 g; 25.0 mmoles; 85% assay) in 900 ml of chloroform at 20°, using a cooling bath to keep the exothermic reaction from rising above 32°. After stirring for 3 hours at ambient temperature, the excess peracid was reacted with an additional 2.0 g of 3,4-dimethoxy-1,2,5-thiadiazole and stirred for 1 hours.

The organic solution was extracted with two-300 ml portions of a 1% solution of $NaHCO_3$, washed with 250 ml of water, dried and evaporated under reduced pressure to give 47.0 g of product. Recrystallization from isopropyl alcohol gave the title compound (34.0 g). An additional recrystallization from isopropyl alcohol gave an analytical sample, mp 135°–137°.

Anal. Calcd for $C_4H_6N_2O_3S$: C, 29.63; H, 3.72; N, 17.27; S, 19.77. Found: C, 29.53; H, 3.75; N, 17.26; S, 19.83.

B. 3-{2-[(5-Methyl-1H-imidazol-4-yl)methylthio]ethylamino}-4-methylamino-1,2,5-thiadiazole 1-oxide A solution of 3,4-dimethoxy-1,2,5-thiadiazole 1-oxide obtained from the above Step A is reacted with an equimolar amount of 2-[(5-methyl-1H-imidazol-4-yl)methylthio]ethylamine and the resulting 3-{2-[(5-methyl-1H-imidazol-4-yl)methylthio]ethylamino}-4-methoxy-1,2,5-thiadiazole 1-oxide is treated with an excess of methylamine, and the title compound is thereby produced.

EXAMPLE 5

3-{2-[(5-Hydroxymethyl-1H-imidazol-4-yl)methylthio]ethylamino}-4-methylamino-1,2,5-thiadiazole 1,1-dioxide 2-[(5-Hydroxymethyl-1H-imidazol-4-yl)methylthio]ethylamine [prepared according to the procedure described in Belgian Pat. No. 843,840] is reacted with 3,4-dimethoxy-1,2,5-thiadiazole 1,1-dioxide and the resultant 3-{2-[(5-hydroxymethyl-1H-imidazol-4-yl)methylthio]ethylamino}-4-methoxy-1,2,5-thiadiazole 1,1-dioxide is treated with excess methylamine according to the general procedure described in Example 2, and the title compound is thereby produced.

EXAMPLE 6

The general procedure of Example 5 is repeated except that the 2-[(5-hydroxymethyl-1H-imidazol-4-yl)methylthio]ethylamine utilized therein is replaced by an equimolar amount of 2-[(5-bromo-1H-imidazol-4-yl)methylthio]ethylamine,
2-[imidazol-4-ylmethylthio]ethylamine,
2-[imidazol-2-ylmethylthio]ethylamine,
2-[(1-methyl-imidazol-2-yl)methylthio]ethylamine,
2-[(2-methyl-1H-imidazol-4-yl)methylthio]ethylamine,
2-[(1-methyl-imidazol-4-yl)methylthio]ethylamine,
2-[(1,5-dimethyl-imidazol-4-yl)methylthio]ethylamine,
2-[(5-chloro-1-methyl-imidazol-4-yl)methylthio]ethylamine,
2-[(5-trifluoromethyl-1H-imidazol-4-yl)methylthio]ethylamine,
2-[(5-ethyl-1H-imidazol-4-yl)methylthio]ethylamine and
2-[(2-amino-1H-imidazol-4-yl)methylthio]ethylamine, respectively, [each prepared by the general procedures described in Belgian Pat. No. 779,775] and there is thereby produced 3-{2-[(5-bromo-1H-imidazol-4-yl)methylthio]ethylamino}-4-methylamino-1,2,5-thiadiazole 1,1-dioxide,
3-{2-[imidazol-4-ylmethylthio]ethylamino}-4-methylamino-1,2,5-thiadiazole 1,1-dioxide,
3-{2-[imidazol-2-ylmethylthio]ethylamino}-4-methylamino-1,2,5-thiadiazole 1,1-dioxide,
3-{2-[(1-methyl-imidazol-2-yl)methylthio]ethylamino}-4-methylamino-1,2,5-thiadiazole 1,1-dioxide,
3-{2-[(2-methyl-1H-imidazol-4-yl)methylthio]ethylamino}-4-methylamino-1,2,5-thiadiazole 1,1-dioxide,
3-{2-[(1-methyl-imidazol-4-yl)methylthio]ethylamino}-4-methylamino-1,2,5-thiadiazole 1,1-dioxide,
3-{2-[(1,5-dimethyl-imidazol-4-yl)methylthio]ethylamino}-4-methylamino-1,2,5-thiadiazole 1,1-dioxide,
3-{2-[(5-chloro-1-methyl-imidazol-4-yl)methylthio]ethylamino}-4-methylamino-1,2,5-thiadiazole 1,1-dioxide,
3-{2-[(5-trifluoromethyl-1H-imidazol-4-yl)methylthio]ethylamino}-4-methylamino-1,2,5-thiadiazole 1,1-dioxide, 3-{2-[(5-ethyl-1H-imidazol-4-yl)methylthio]ethylamino}-4-methylamino-1,2,5-thiadiazole 1,1-dioxide and 3-{2-[(2-amino-1H-imidazol-4-yl)methylthio]ethylamino}-4-methylamino-1,2,5-thiadiazole 1,1-dioxide, respectively.

EXAMPLE 7

3-Hydroxy-4-{2-[(5-methyl-1H-imidazol-4-yl)methylthio]ethylamino}-1,2,5-thiadiazole 1,1-dioxide When a methanolic solution of 3-{2-[(5-methyl-1H-imidazol-4-yl)methylthio]ethylamino}-4-methoxy-1,2,5-thiadiazole 1,1-dioxide [prepared by the procedure of Step A of Example 1] is treated with a solution of sodium hydroxide in methanol by the general procedure of Example 17, Step B, the title compound is produced, mp 263°–265° (dec).

Anal. Calcd $C_9H_{13}N_5S_2O_3$: C, 35.64; H, 4.32; N, 23.09; S, 21.13. Found: C, 35.56; H, 4.38; N, 23.01; S, 21.13.

EXAMPLE 8

3-{4-[(2-Guanidino-1H-imidazol-4-yl]butylamino}-4-methylamino-1,2,5-thiadiazole 1,1-dioxide A methanolic suspension of 3,4-dimethoxy-1,2,5-thiadiazole 1,1-dioxide is successively reacted with an equimolar amount of 4-[2-guanidino-1H-imidazol-4-yl]butylamine [prepared according to Belgian Pat. No. 866,156] and excess methylamine according to the general procedure of Example 2, and the title compound is thereby produced.

EXAMPLE 9

3-{2-[(5-Methyl-1H-imidazol-4-yl)methylthio]ethylamino}-4-(2-propynyl)amino-1,2,5-thiadiazole 1,1-dioxide Reaction of a methanolic suspension of 3,4-dimethoxy-1,2,5-thiadiazole 1,1-dioxide wth one equivalent of 2-propynylamine and treating the resultant 3-methoxy-4-propynylamino-1,2,5-thiadiazole 1,1-dioxide with one equivalent of 2-[(5-methyl-1H-imidazol-4-yl)methylthio]ethylamine yields the title compound; identical to the product of Example 1.

EXAMPLE 10

3-{2-[(5-Methyl-1H-imidazol-4-yl)methylthio]ethylamino}-4-methylamino-1,2,5-thiadiazole 1,1-dioxide When a solution of 3-methylamino-4-(2-mercaptoethyl)-1,2,5-thiadiazole 1,1-dioxide (prepared in Example 25, Step A) is reacted with 4-chloromethyl-5-methylimidazole hydrochloride and a strong base, the title compound is thereby produced; identical to the product of Example 2.

EXAMPLE 11

3-{2-[(5-Dimethylaminomethyl-2-furyl)methylthio]ethylamino}-4-methylamino-1,2,5-thiadiazole 1,1-dioxide and
3,4-bis-{2-[(5-dimethylaminomethyl-2-furyl)methylthio]ethylamino}-1,2,5-thiadiazole 1,1-dioxide A. 3-{2-[(5-Dimethylaminomethyl-2-furyl)methylthio]ethylamino}-4-methoxy-1,2,5-thiadiazole 1,1-dioxide A solution of 2-[(5-dimethylaminomethyl-2-furyl)methylthio]ethylamine (2.41 g; 11.2 mmoles) [prepared according to the procedure described in Belgian Pat. No. 857,388] in 20 ml of dry methanol was added all at once to a well stirred, cold (8°) suspension of 3,4-dimethoxy-1,2,5-thiadiazole 1,1-dioxide (2.0 g; 11.2 mmoles) in 200 ml of methanol. After stirring at 8°–10° for 15 minutes, a methanolic solution of the title compound is produced.

B. 3-{2-[(5-Dimethylaminomethyl-2-furyl)methylthio]ethylamino}-4-methylamino-1,2,5-thiadiazole 1,1-dioxide Anhydrous methylamine was bubbled into the cooled (1°) methanolic solution of the product of Step A for 6 minutes. Stirring was continued for 10 minutes and the mixture was evaporated under reduced pressure. The residue was placed on 45 g of silica gel and chromatographed using a gradient elution of methylene chloride-methanol. The appropriate fractions, using methylene chloride-methanol (95:5) were combined in methanol, filtered through Celite, and then concentrated under reduced pressure to give product. Recrystallization from methanol yielded the title compound (1.76 g), mp 82°–90°; the NMR spectrum (100 MHz) in $d_6$ dimethyl sulfoxide showed the presence of $\frac{2}{3}$ mole of methanol.

Anal. Calcd for $C_{13}H_{21}N_5O_3S_2 \cdot \frac{2}{3}CH_3OH$: C, 43.10; H, 6.26; N, 18.38; S, 16.83. Found (corr. for 1.72% $H_2O$): C, 43.30; H, 6.12; N, 18.57; S, 16.96.

C. 3,4-Bis-{2-[(5-dimethylaminomethyl-2-furyl)methylthio]ethylamino}-1,2,5-thiadiazole 1,1-dioxide The slower eluting component using methylene chloride-methanol (9:1) from the chromatography in Step B was placed on 45 g of aluminum oxide and chromatographed using a gradient elution of ethyl acetate-methanol. The appropriate fraction was evaporated and the residue triturated under ether-acetonitrile to give a colorless solid which was collected by filtration to yield the title compound (428 mg) as a monohydrate, mp 92.5°–96°.

Anal. Calcd for $C_{22}H_{34}N_6S_3O_4 \cdot H_2O$: C, 47.12; H, 6.47; N, 14.99; S, 17.15. Found: C, 47.28; H, 6.48; N, 15.09; S, 17.39. Calcd for $H_2O = 3.21\%$; Found $H_2O = 3.32\%$.

EXAMPLE 12

3-{2-[(5-Dimethylaminomethyl-2-furyl)methylthio]ethylamino}-4-ethylamino-1,2,5-thiadiazole 1,1-dioxide A solution of 2-[(5-dimethylaminomethyl-2-furyl)methylthio]ethylamine (2.41 g; 11.2 mmoles) in 20 ml of dry methanol was added all at once to a well stirred cold (1°) suspension of 3,4-dimethoxy-1,2,5-thiadiazole 1,1-dioxide (2.0 g; 11.2 mmoles) in 200 ml of methanol. After stirring for 15 minutes at 1°–5°, ethylamine (4.0 ml) was added and stirring was continued at approximately 5° for 20 minutes. The reaction mixture was evaporated under reduced pressure and the residue was placed on 46 g of silica gel and chromatographed using a gradient elution of methylene chloride-methanol. The appropriate fractions were combined, evaporated and the gelatinous residue triturated under ether and filtered to give the product as a colorless solid (2.81 g). Two recrystallizations from methanol and drying over $P_2O_5$ at ambient temperature for 17 hours yielded the title compound, mp 155°–160° with variable sintering at 94°–96°; the NMR spectrum (100 MHz) in $d_6$ dimethyl sulfoxide showed the presence of approximately 0.8 moles of methanol.

Anal. Calcd for $C_{14}H_{23}N_5O_3S_2 \cdot 0.8CH_3OH$: C, 44.54; H, 6.62; N, 17.55; S, 16.07. Found: C, 44.35; H, 6.58; N, 17.44; S, 16.18.

EXAMPLE 13

3-{2-[(5-Dimethylaminomethyl-2-furyl)methylthio]ethylamino}-4-(2-propynyl)amino-1,2,5-thiadiazole 1,1-dioxide A solution of 2-[(5-dimethylaminomethyl-2-furyl)methylthio]ethylamine (2.41 g; 11.2 mmoles) in 20 ml of dry methanol was added dropwise over a period of 25 minutes to a well stirred cold (1°) suspension of 3,4-dimethoxy-1,2,5-thiadiazole 1,1-dioxide (2.0 g; 11.2 mmoles) in 200 ml of methanol. After stirring at 1°–2° for 15 minutes, a solution of 2-propynylamine (4.0 ml) in 10 ml of dry methanol was added all at once, and stirring was then continued at ambient temperature for 1 hour. The reaction mixture was evaporated under reduced pressure and the residue was placed on 50 g of silica gel and chromatographed using a gradient elution of methylene chloride-methanol. The appropriate fractions were combined, evaporated and crystallized from methanol to give 4.0 g of product. Recrystallization from methanol and then from isopropyl alcohol yielded the title compound (2.90 g), mp 92°–100°; the NMR spectrum (100 MHz) in $d_6$ dimethyl sulfoxide showed the product to be solvated with 1 mole of methanol.

Anal. Calcd for $C_{15}H_{21}N_5O_3S_2 \cdot CH_3OH$: C, 46.25; H, 6.06; N, 16.85; S, 15.43. Found: C, 46.36; H, 6.22; N, 16.95; S, 15.73.

EXAMPLE 14

3-Methylamino-4-{2-[(5-{[N-methyl-N-(2-propynyl)amino]methyl}-2-furyl)methylthio]ethylamino}-1,2,5-thiadiazole 1,1-dioxide A. 5-{[N-methyl-N-(2-propynyl)amino]methyl}-2-furanmethanol To furfuryl alcohol (2.49 g; 25.4 mmoles) which was cooled in an ice-water bath to 5° was added N-methylpropargylamine hydrochloride (4.0 g; 37.9 mmoles) and 40% formalin (3.13 ml; 41.7 mmoles), and the mixture stirred while allowed to reach ambient temperature. After 1 hour of stirring the solution was allowed to stand at ambient temperature for 4½ days. The reaction mixture was poured into ice water, made strongly basic with 40% aqueous NaOH and extracted with five portions of methylene chloride. The combined organic phase was dried, filtered and evaporated under reduced pressure to give the product as an oil (quantitative yield). Vacuum distillation yielded the title compound, bp 102°–106°/0.3 mm Hg.

Anal. Calcd for $C_{10}H_{13}NO_2$: C, 67.02; H, 7.31; N, 7.82. Found: C, 66.80; H, 7.44; N, 7.93.

B. 2-[(5-{[N-Methyl-N-(2-propynyl)amino]methyl}-2-furyl)methylthio]ethylamine

A solution of 5-{[N-methyl-N-(2-propynyl)amino]methyl}-2-furanmethanol (40.0 g; 223 mmoles) [prepared in Step A] in 100 ml of ice-cold concentrated HCl was added to a cold (5°) stirred solution of cysteamine hydrochloride (27.9 g; 24.6 mmoles) in 125 ml of concentrated hydrochloric acid. The solution was allowed to stand at 0° for 2½ days, and then at ambient temperature for 7 hours to complete the reaction. The reaction mixture was cooled in an ice-water bath, diluted with 200 ml of water, made strongly alkaline with 40% aqueous NaOH, and then extracted with three portions of methylene chloride. The combined organic phase was dried, filtered, and evaporated under reduced pressure to give the product as a thick oil (46.4 g). A rapid vacuum distillation of the oil yielded the title compound, bp 136°–140°/0.2 mm Hg.

Anal. Calcd for $C_{12}H_{18}N_2OS$: C, 60.47; H, 7.61; N, 11.76; S, 13.46. Found: C, 59.82; H, 7.68; N, 11.61; S, 13.27.

C. 3-Methylamino-4-{2-[(5-{[N-methyl-N-(2-propynyl)amino]methyl-2-furyl)methylthio]ethylamino}-1,2,5-thiadiazole 1,1-dioxide To a stirred cold (3°) suspension of 3,4-dimethoxy-1,2,5-thiadiazole 1,1-dioxide (2.0 g; 11.2 mmoles) in 200 ml of dry methanol was added a solution of 2-[(5-{[N-methyl-N-(2-propynyl)amino]methyl}-2-furyl)methylthio]ethylamine (2.68 g; 11.2 mmoles) [prepared in Step B]. After stirring at 3°–7° for 15 minutes, methylamine was bubbled into the solution for 16 minutes. The reaction mixture was evaporated under reduced pressure and the oily residue was placed on 100 g of silica gel and chromatographed using a gradient of acetonitrile-methanol. The appropriate fractions were combined and rechromatographed on 100 g of silica gel using a gradient of methylene chloride-methanol. The appropriate fractions was dissolved in methylene chloride and extracted with 1% aqueous NaOH. The aqueous phase was brought to pH 9 with 5% aqueous HCl and the separated oil was extracted with three portions of methylene chloride. The combined extracts were dried, filtered and evaporated under reduced pressure to give product as a foam. Recrystallization from isopropyl alcohol yielded the title compound, mp. 50°–51°, clear melt 54°–56°; the NMR spectrum (100 MHz) in $D_6$ dimethyl sulfoxide showed the presence of approximately ¼ mole of isopropyl alcohol.

Anal. Calcd for $C_{15}H_{21}N_5O_3S_2 \cdot \frac{1}{4}C_3H_8O$: C, 47.47; H, 5.82; N, 17.57; S, 16.09. Found: C, 47.51; H, 6.21; N, 16.40; S, 15.97.

EXAMPLE 15

3-{2-[(5-Dimethylaminomethyl-3-methyl-2-furyl)methylthio]ethylamino}-4-methylamino-1,2,5-thiadiazole 1,1-dioxide A. 5-Dimethylaminomethyl-3-methyl-2-furanmethanol A mixture containing 3-methyl-2-furfuryl alcohol (11.2 g; 0.1 mole [prepared according to the procedure described in J. Am. Chem. Soc., 72, 2195 (1950)], dimethylamine hydrochloride (12.23 g; 0.15 mole) and 37% aqueous formaldehyde (12 ml, 0.15 mole) was stirred for 2.5 hours at approximately 5°, and then at ambient temperature overnight. The solution was heated for 10 minutes on a steam bath, diluted with 12 ml of water and basified with sodium carbonate. The mixture was extracted with ethyl acetate, and the organic phase dried, filtered and evaporated under reduced pressure to yield the title compound, bp 88–96/0.05–0.08 mm Hg.

B. 2-[(5-Dimethylaminomethyl-3-methyl-2-furyl)methylthio]ethylamine

To a solution of 2-aminoethanethiol hydrochloride (2.27 g; 20.0 mmoles) in 20 ml of concentrated HCl that was cooled in an ice-salt bath to −10° was added dropwise 5-dimethylaminomethyl-3-methyl-2-furanmethanol (3.38 g; 20.0 mmoles) [prepared in Step A], and the mixture stirred for 15 minutes then allowed to stand in the cold (0°) overnight. After 17 hours the cold solution was made strongly basic with aqueous KOH solution and then extracted with five portions of methylene chloride. The combined organic phase was dried, filtered and evaporated under reduced pressure to yield the title compound (4.16 g), bp 110°-120°/0.1 mm Hg.

C. 3-{2-[(5-Dimethylaminomethyl-3-methyl-2-furyl)methylthio]ethylamino}-4-methylamino-1,2,5-thiadiazole 1,1-dioxide When a methanol suspension of 3,4-dimethoxy1,2,5-thiadiazole 1,1-dioxide is reacted with an equimolar amount of 2-[(5-dimethylaminomethyl-3-methyl-2-furyl)methylthio]ethylamine [prepared in Step B] and the resultant 3-{2-[(5-dimethylaminomethyl-3-methyl-2-furyl)methylthio]ethylamino}-4-methoxy-1,2,5-thiadiazole 1,1-dioxide is treated with an excess of methylamine, the title compound is thereby produced.

EXAMPLE 16

3-{2-[(5-Dimethylaminomethyl-4-methyl-2-furyl)methylthio]ethylamino}-4-methylamino-1,2,5-thiadiazole 1,1-dioxide A. 2-Dimethylaminomethyl-3-methylfuran A stirred solution of 3-methyl-2-furfuryl alcohol 25.2 g; 22.5 mmoles) and triethylamine (27.3 g; 27.0 mmoles) in 200 ml of methylene chloride was cooled to −15° in an ice-salt bath and a solution of thionyl chloride (18.0 ml, 24.8 mmoles) in 30 ml of methylene chloride was added dropwise, keeping the temperature between −10° to −15°. After 15 minutes, the mixture was poured into ice-water and the organic layer was separated. The methylene chloride phase containing 3-methyl-2-chloromethylfuran was added to a stirred solution, at 0°, of dimethylamine (137.0 g; 3.04 moles) in 400 ml of absolute ethanol and the resulting solution was stirred at ambient temperature for 17 hours. The reaction mixture was evaporated under reduced pressure and the residue was mixed with 400 ml of water, made strongly basic with 40% aqueous NaOH and extracted with five portions of methylene chloride. The combined extracts were dried, filtered and evaporated under reduced pressure to yield 26.0 g of the title compound, bp 64°-70°/20 mm Hg. A TLC [Silica/CHCl$_3$:CH$_3$OH (85:15)] gave Rf=0.50.

B. 2-Chloromethyl-5-dimethylaminomethyl-3-methylfuran

To a solution of 2-dimethylaminomethyl-3-methylfuran (6.5 g; 37.0 mmoles) [prepared in Step A] in 250 ml of chloroform was added paraformaldehyde (1.67 g; 55.7 mmoles) and zinc chloride (312 mg), and a slow stream of HCl gas was bubbled through while stirring at ambient temperature for 15 minutes. Stirring was continued for 2 hours, then HCl gas was bubbled through for 15 minutes and the mixture stirred for 1 hour. At this time additional paraformaldehyde (1.67 g; 55.7 mmoles) was added to the reaction mixture and a slow stream of HCl gas was passed through for 15 minutes. After stirring at ambient temperature for 18 hours, the reaction mixture was filtered through Celite and the filtrate evaporated under reduced pressure to yield the title compound (4.97 g) which crystallized upon standing and was used without further purification in Step C.

The NMR spectrum (60 MHz) in CDCl$_3$ gave the following resonances δ: 6.33 (s, 1H), 4.55 (s, 2H); 4.30 (d, 2H); 2.83 (d, 6H); 2.13 (s, 3H)

C. 2-[(5-Dimethylaminomethyl-4-methyl-2-furyl)methylthio]ethylamine

To a solution of 2-chloromethyl-5-dimethylaminomethyl-3-methylfuran (773 mg, 3.45 mmoles) [prepared in Step B] in 20 ml of concentrated hydrochloric acid that was cooled in an ice-water bath was added 2-aminoethanethiol hydrochloride (392 mg; 3.45 mmoles), and the mixture was stirred for 30 minutes. The solution was allowed to stand at 0° for 3 days, then made strongly basic with 50% aqueous KOH, diluted with water and extracted with five portions of methylene chloride. The combined extract was dried, filtered and evaporated under reduced pressure to yield the title compound as an oil.

The product was dissolved in absolute ethanol, treated with anhydrous hydrogen chloride and evaporated under reduced pressure. The residue was dissolved in hot isopropyl alcohol, treated with charcoal, filtered and concentrated to crystallize the hydrochloride salt. Recrystallization from isopropyl alcohol yielded the title compound as the dihydrochloride salt, mp 185°-190° (dec).

D. 3-{2-[(5-Dimethylaminomethyl-4-methyl-2-furyl)methylthio]ethylamino}-4-methylamino-1,2,5-thiadiazole 1,1-dioxide When a methanol suspension of 3,4-dimethoxy-1,2,5-thiadiazole 1,1-dioxide is reacted with an equimolar amount of 2-[(5-dimethylaminomethyl-4-methyl-2-furyl)methylthio]ethylamine [prepared in Step C] and the resultant 3-{2-[(5-dimethylaminomethyl-4-methyl-2-furyl)methylthio]ethylamino}-4-methoxy-1,2,5-thiadiazole 1,1-dioxide is treated with an excess of methylamine, the title compound is produced.

EXAMPLE 17

3-{2-[(5-Dimethylaminomethyl-2-furyl)methylthio]ethylamino}-4-hydroxy-1,2,5-thiadiazole 1,1-dioxide A. 3-{2-[(5-Dimethylaminomethyl-2-furyl)methylthio]ethylamino}-4-methoxy-1,2,5-thiadiazole 1,1-dioxide A solution of 2-[(5-dimethylaminomethyl-2-furylmethylthio]ethylamine (2.14 g; 10.0 mmoles) in 25 ml of dry methanol was added dropwise over 35 minutes to a well stirred suspension of 3,4-dimethoxy-1,2,5-thiadiazole 1,1-dioxide (1.78 g; 10.0 mmoles) in 180 ml of dry methanol that had been cooled to 1° in an ice-water bath. After 15 minutes at 0°, a methanol solution of the title compound is produced. A TLC [silica/CH$_2$Cl$_2$:CH$_3$OH (9:1)] gave Rf=0.48.

A 2.0 ml aliquot of the solution was made acidic with 6.0 N HCl and evaporated under reduced pressure without heating to yield the title compound as the hydrochloride salt. The NMR spectrum (100 MHz) in D$_2$O gave the following resonances δ: 6.45 (d, 1H); 6.19 (d, 1H); 4.14 (s, 2H); 4.0 (s, 3H); 3.64 (s, 2H); 3.37 (t, 2H); 2.65 (s, 6H); 2.61 (t, 2H).

B. 3-{2-[(5-Dimethylaminomethyl-2-furyl)methylthio]ethylamino}-4-hydroxy-1,2,5-thiadiazole 1,1-dioxide To the methanolic solution of the product of Step A, cooled to 0° in an ice-water bath, was added a solution of sodium hydroxide pellets (2.10 g; 52.5 mmoles) in 25 ml of dry methanol. After stirring at 0° for 2 hours and at ambient temperature for 68 hours, the reaction mixture was neutralized with 8.75 ml (52.5 mmoles) of aqueous 6.0 N HCl and after 10 minutes for stirring was evaporated under reduced pressure. The residue was crystallized under 95% EtOH to give crude product which was dissolved in methanol, filtered to remove sodium chloride, placed on 60 g of silica gel and chromatographed using a gradient elution of methylene chloride-methanol. The appropriate fractions were combined and evaporated under reduced pressure to give 3.19 g of product. Recrystallization from aqueous methanol yielded the title compound, mp 109°-122°.

Anal. Calcd for $C_{12}H_{18}N_4O_4S_2$: C, 41.61; H, 5.24; N, 16.17; S, 18.51. Found (corr. for 1.15% $H_2O$): C, 41.59; H, 5.32; N, 16.33; S, 18.81.

EXAMPLE 18

3-{2-[(5-Dimethylaminomethyl-2-furyl)methylthio]ethylamino}-4-methylamino-1,2,5-thiadiazole 1-oxide A. 3-{2-[(5-Dimethylaminomethyl-2-furyl)methylthio]ethylamino}-4-methoxy-1,2,5-thiadiazole 1-oxide A solution of 2-[(5-dimethylaminomethyl-2-furyl)methylthio]ethylamine (3.30 g; 15.4 mmoles) in 25 ml of methanol was added dropwise over a period of 14 minutes to a well stirred suspension of 3,4-dimethoxy-1,2,5-thiadiazole 1-oxide (2.50 g; 15.4 mmoles) [prepared according to the procedure in Example 4, Step A] that was cooled to 12°–15° in an ice-water bath. The solution was stirred at ambient temperature for 1.5 hours to yield a methanolic solution of the title compound.

B. 3-{2-[(5-Dimethylaminomethyl-2-furyl)methylthio]ethylamino}-4-methylamino-1,2,5-thiadiazole 1-oxide To the methanolic solution of the product of Step A that was cooled to 5° in an ice-water bath was added anhydrous methylamine for 8 minutes. The reaction mixture was stirred at ambient temperature for 17 hours, then evaporated under reduced pressure to give the product as a yellow oil that was placed on 55 g of silica gel and chromatographed using a gradient elution of methylene chloride-methanol. The appropriate fraction was evaporated, dissolved in methanol and diluted with diethyl ether to yield the title compound (2.32 g) as a solid that was dried in vacuo at ambient temperature over $P_2O_5$ for 3 hours, mp 86°–92°.

Anal. Calcd for $C_{13}H_{21}N_5O_2S_2$: C, 45.46; H, 6.16; N, 20.39; S, 18.67. Found: C, 45.24; H, 6.24; N, 20.41; S, 18.90.

EXAMPLE 19

3-Allylamino-4-{2-[(5-dimethylaminomethyl-2-furyl)methylthio]ethylamino}-1,2,5-thiadiazole 1,1-dioxide To a partial suspension of 3,4-dimethoxy-1,2,5-thiadiazole 1,1-dioxide (2.08 g; 11.7 mmoles) in 200 ml of methanol that had been cooled to 0° in an ice-water bath was added dropwise over a period of 45 minutes a solution of 2-[(5-dimethylaminomethyl-2-furyl)methylthio]ethylamine in 30 ml of methanol. When the addition was completed, 10.5 ml of allylamine was added and the solution was allowed to stir at ambient temperature for 18 hours. The reaction mixture was evaporated under reduced pressure and the residue was placed on 120 g of silica gel and chromatographed using a gradient elution of methylene chloride-methanol. The appropriate fractions were combined, evaporated under reduced pressure and the residue crystallized with isopropyl alcohol to give the title compound, mp 83°–86°; the NMR spectrum (100 MHz) in $d_6$ dimethyl sulfoxide showed the presence of approximately 0.9 moles of isopropyl alcohol.

Anal. Calcd for $C_{15}H_{23}N_5O_3S_2\cdot 0.9C_3H_8O$: C, 48.36; H, 6.92; N, 15.93; S, 14.59. Found: C, 48.46; H, 6.96; N, 16.13; S, 14.58.

EXAMPLE 20

3-Methylamino-4-{2-[(5-methylaminomethyl-2-furyl)methylthio]ethylamino}-1,2,5-thiadiazole 1,1-dioxide
and
3,4-bis-{2-[(5-methylaminomethyl-2-furyl)methylthio]ethylamino}-1,2,5-thiadiazole 1,1-dioxide A. 3-Methylamino-4-{2-[(5-methylaminomethyl-2-furyl)methylthio]ethylamino}-1,2,5-thiadiazole 1,1-dioxide To a partial suspension of 3,4-dimethoxy-1,2,5-thiadiazole (1.89 g; 10.5 mmoles) in 210 ml of methanol that was cooled to 8° was added all at once a solution of 2-[(5-methylaminomethyl-2-furyl)methylthio]ethylamine (0.7 g; 3.51 mmoles) [prepared according to the procedure described in Belgian Pat. No. 857,388] in 21 ml of methanol. The mixture was stirred for 15 minutes and cooled to 1° in an ice-water bath, and anhydrous methylamine then was bubbled into the solution for 6 minutes. After stirring for 15 minutes the reaction mixture was evaporated under reduced pressure and the residue placed on 110 g of silica gel using a gradient elution from acetonitrile to acetonitrile-methanol-glacial acetic acid (50:50:0.5). The appropriate fractions containing the first eluting component with Rf=0.50 [TLC-silica/$CH_3CN:CH_3OH:CH_3COOH$ (50:50:1)] were combined and evaporated under reduced pressure to yield the title compound as a foam, mp. 50°–56°.

The NMR spectrum (100 MHz) in $d_6$ dimethyl sulfoxide gave the following resonances δ: 6.20 (m, 2H); 3.80 (s, 2H); 3.62 (s, 2H); 3.50 (t, 2H); 2.90 (s, 3H); 2.70 (t, 2H); 2.28 (s, 3H); it also showed the presence of approximately 0.2 mole of methanol.

Anal. Calcd for $C_{12}H_{19}N_5O_3S_2\cdot 0.2CH_3OH$: C, 41.65; H, 5.65; N, 19.96; S, 18.28. Found (corr. for 1.42% $H_2O$): C, 41.98; H, 5.69; N, 19.54; S, 18.54.

B. 3,4-Bis-{2-[(5-methylaminomethyl-2-furyl)methylthio]ethylamino}-1,2,5-thiadiazole 1,1-dioxide The fractions containing the slower eluting component from the chromatography in Step A with Rf=0.07 [TLC-silica/$CH_3CN:CH_3OH:CH_3COOH$ (50:50:1)] were combined, evaporated and the residue partitioned between 2.5 N NaOH and ethyl acetate. The aqueous phase was extracted with several portions of ethyl acetate and the combined organic layer was dried and evaporated under reduced pressure to give the title compound as an oil.

The NMR spectrum (100 MHz) in $d_6$ dimethyl sulfoxide gave the following resonances δ: 6.22 (m, 4H); 3.82 (s, 4H); 3.65 (s, 4H); 3.50 (t, 4H); 2.72 (t, 4H); 2.30 (s, 6H).

EXAMPLE 21

3-{4-(5-Dimethylaminomethyl-2-furyl)butylamino}-4-methylamino-1,2,5-thiadiazole 1,1-dioxide A solution of 4-(5-dimethylaminomethyl-2-furyl)butylamine (1.5 g; 7.64 mmoles) [prepared according to the procedure described in U.S. Pat. No. 4,128,658] in 40 ml of dry methanol was added dropwise over a period of 45 minutes to a stirred solution of 3,4-dimethoxy-1,2,5-thiadiazole 1,1-dioxide (1.36 g; 7.64 mmoles) in 200 ml of dry methanol that had been cooled to 3° in an ice-water bath. After 15 minutes at 3°, anhydrous methylamine was bubbled into the cooled solution for 10 minutes. The reaction mixture was evaporated under reduced pressure and the residue placed on 60 g of silica gel and chromatographed using a gradient elution of acetonitrile-methanol. The appropriate fractions were combined to give 2.16 g of product. Recrystallization from acetonitrile yielded the title compound, mp 152°–153°.

Anal. Calcd for $C_{14}H_{23}N_5O_3S$: C, 49.25; H, 6.79; N, 20.51; S, 9.39. Found: C, 49.41; H, 6.87; N, 20.61; S, 9.28

EXAMPLE 22

3-{2-[(5-Dimethylaminomethyl-2-furyl)methoxy]ethylamino}-4-methylamino-1,2,5-thiadiazole 1,1-dioxide When a methanolic suspension of 3,4-dimethoxy-1,2,5-thiadiazole 1,1-dioxide is reacted with one equivalent of 2-[(5-dimethylaminomethyl-2-furyl)methoxy]ethylamine [prepared according to U.S. Pat. No. 4,128,658] and then with excess methylamine, the title compound is thereby produced.

EXAMPLE 23

3-{2-[(5-Dimethylaminomethyl-2-furyl)methylthio]ethylamino}-4-ethylamino-1,2,5-thiadiazole 1,1-dioxide Reaction of a methanolic suspension of 3,4-dimethoxy-1,2,5-thiadiazole 1,1-dioxide with one equivalent of ethylamine and treatment of the resultant 3-methoxy-4-ethylamino-1,2,5-thiadiazole 1,1-dioxide with one equivalent of 2-[(5-dimethylaminomethyl-2-furyl)methylthio]ethylamine yields the title compound, which is identical to the product prepared in Example 12.

EXAMPLE 24

3-{2-[(5-Dimethylaminomethyl-2-furyl)methylthio]ethylamino}-4-methylamino-1,2,5-thiadiazole 1-oxide Reaction of a methanolic solution of 3,4-dimethoxy-1,2,5-thiadiazole 1-oxide [prepared in Example 4, Step A] with one equivalent of methylamine and treatment of the resultant 3-methoxy-4-methylamino-1,2,5-thiadiazole 1-oxide with one equivalent of 2-[(5-dimethylaminomethyl-2-furyl)methylthio]ethylamine yields the title compound, which is identical to the product prepared in Example 18.

EXAMPLE 25

3-{2-[(5-Dimethylaminomethyl-2-furyl)methylthio]ethylamino}-4-methylamino-1,2,5-thiadiazole 1,1-dioxide A. 3-Methylamino-4-(2-mercaptoethyl)-1,2,5-thiadiazole 1,1-dioxide A solution of 2-aminoethanethiol (from the hydrochloride 1.91 g; 16.8 mmoles) in 20 ml of methanol was added dropwise over a period of 15 minutes to a well stirred suspension of 3,4-dimethoxy-1,2,5-thiadiazole 1,1-dioxide (3.0 g; 16.8 mmoles) in 250 ml of methanol that had been cooled to 1° in an ice-water bath. After 10 minutes at 2°–4°, methylamine was bubbled into the cooled solution for 6 minutes and stirring was continued for an additional 30 minutes at ambient temperature. The reaction mixture was evaporated under reduced pressure and the residue placed on 45 g of silica gel and chromatographed using a gradient elution of methylene chloride-methanol. The appropriate fractions were combined and evaporated, and the product (2.43 g) was crystallized from absolute ethanol. Recrystallization from absolute ethanol yielded the title compound, mp. 259°–260° (dec).

Anal. Calcd for $C_5H_{10}N_4O_2S_2$: C, 27.03; H, 4.54; N, 25.20. Found: C, 27.13; H, 4.55; N, 24.86.

B. 3-{2-[(5-Dimethylaminomethyl-2-furyl)methylthio]ethylamino}-4-methylamino-1,2,5-thiadiazole 1,1-dioxide A mixture containing 3-methylamino-4-(2-mercaptoethyl-1,2,5-thiadiazole 1,1-dioxide (1.0 g; 4.5 mmoles) [prepared in Step A] and 5-dimethylaminomethyl-2-furanmethanol (0.82 g; 4.5 mmoles) [prepared according to the procedure in *J. Chem. Soc.*, 4728 (1958)] in 20 ml of concentrated hydrochloric acid was stirred in an ice-water bath for 2 hours and then allowed to stand at 0° for 64 hours. The reaction mixture was stirred at ambient temperature for 23 hours, evaporated without heating under reduced pressure and the residue partitioned between water and methylene chloride. The aqueous phase was made basic with sodium bicarbonate and extracted with methylene chloride. The combined organic phase was washed with saturated brine solution, dried and evaporated under reduced pressure. The residue was placed on 25 g of silica gel and chromatographed using a gradient elution of methylene chloride-methanol. The appropriate fraction was evaporated and the product crystallized from methanol. Recrystallization from methanol yielded the title compound, mp 92°–96°.

EXAMPLE 26

3-{2-[(5-Dimethylaminomethyl-2-furyl)methylthio]ethylamino}-4-methylamino-1,2,5-thiadiazole 1-oxide A. 3-Methylamino-4-(2-mercaptoethyl)-1,2,5-thiadiazole 1-oxide A solution of 2-aminoethanethiol (from the hydrochloride, 2.04 g; 18.0 mmoles) in 25 ml of methanol was added dropwise over a period of 30 minutes to a well stirred suspension of 3,4-dimethoxy-1,2,5-thiadiazole 1-dioxide (2.92 g; 18.0 mmoles) [prepared in Example 4, Step A] in 150 ml of methanol that had been cooled to 3° in an ice-water bath. After 10 minutes, anhydrous methylamine was bubbled into the solution for 6 minutes and stirring was continued at ambient temperature for an additional 20 minutes. The reaction mixture was evaporated under reduced pressure and the residue placed on 45 g of silica gel and chromatographed using a gradient elution of methylene chloride-methanol. The appropriate fractions were combined and evaporated to give 2.74 g of product. Recrystallization from methanol and then 95% ethanol yielded the title compound, mp 191°–193°.

B. 3-{2-[(5-Dimethylaminomethyl-2-furyl)methylthio]ethylamino}-4-methylamino-1,2,5-thiadiazole 1-oxide When 3-methylamino-4-(2-mercaptoethyl)-1,2,5-thiadiazole 1-oxide [prepared in Step A] is treated with about one equivalent of 5-dimethylaminomethyl-2-furanmethanol in concentrated hydrochloric acid according to the procedure described in Example 25, Step B, the title compound is thereby produced; identical to the product of Example 18.

EXAMPLE 27

3-{3-[(5-Dimethylaminomethyl-2-furyl)methylthio]propylamino}-4-ethylamino-1,2,5-thiadiazole 1,1-dioxide When 1-phthalimido-3-[(5-dimethylaminomethyl-2-furyl)methylthio]propane [prepared according to the procedure described in Belgian Pat. No. 857,388] is treated with hydrazine, and the resulting substituted propylamine is reacted according to the general procedure of Example 12, the title product is thereby produced.

EXAMPLE 28

3-{2-[(5-Dimethylaminomethyl-2-furyl)methylthio]ethylamino}-4-dimethylamino-1,2,5-thiadiazole 1,1-dioxide To a cooled (6°) partial suspension of 3,4-dimethoxy-1,2,5-thiadiazole 1,1-dioxide (2.08 g; 11.7 mmoles) in 200 ml of methanol was added dropwise over a period of 45 minutes a solution of 2-[(5-dimethylaminomethyl-2-furyl)methylthio]ethylamine (2.5 g; 11.7 mmoles) in 50 ml of methanol. When the addition was completed, anhydrous dimethylamine was bubbled into the solution for 10 minutes while maintaining the temperature at 6°. After stirring at ambient temperature for 18 hours, the reaction mixture was evaporated under reduced pressure and the residue placed on 200 g of silica and chromatographed using a gradient elution of methylene chloride-methanol. The appropriate fractions were combined and evaporated and the residue was rechromatographed on 75 g of aluminum oxide using a gradient elution of methylene chloride-methanol. The appropriate fractions were combined and evaporated under reduced pressure to give the title compound, mp 139°–142°.

Anal. Calcd for $C_{19}H_{24}N_5O_3S_2$: C, 44.90; H, 6.46; N, 18.70; S, 17.12. Found (Corr. for 0.51% $H_2O$): C, 44.77; H, 6.25; N, 18.89; S, 17.42.

EXAMPLE 29

The general procedure of Example 28 is repeated, except that the dimethylamine utilized therein is replaced by
thiomorpholine,
piperazine,
N-acetylpiperazine,
N-methylpiperazine,
hexamethyleneimine and
homopiperazine, respectively, and there is thereby produced
3-{2-[(5-dimethylaminomethyl-2-furyl)methylthio]ethylamino}-4-(4-thiomorpholinyl)-1,2,5-thiadiazole 1,1-dioxide,
3-{2-[(5-dimethylaminomethyl-2-furyl)methylthio]ethylamino}-4-(1-piperazinyl)-1,2,5-thiadiazole 1,1-dioxide,
3-{2-[(5-dimethylaminomethyl-2-furyl)methylthio]ethylamino}-4-(4-acetyl-1-piperazinyl)-1,2,5-thiadiazole 1,1-dioxide,
3-{2-[(5-dimethylaminomethyl-2-furyl)methylthio]ethylamino}-4-(4-methyl-1-piperazinyl)-1,2,5-thiadiazole 1,1-dioxide,
3-{2-[(5-dimethylaminomethyl-2-furyl)methylthio]ethylamino}-4-(1-hexamethyleneimino)-1,2,5-thiadiazole 1,1-dioxide and
3-{2-[(5-dimethylaminomethyl-2-furyl)methylthio]ethylamino}-4-(1-homopiperazinyl)-1,2,5-thiadiazole 1,1-dioxide, respectively.

EXAMPLE 30

The general procedure of Example 13 is repeated, except that the 2-propynylamine utilized therein is replaced by an equimolar amount of
cyclobutylamine,
aminomethylcyclobutane,
ethanolamine,
2-methylthioethylamine,
2,2,2-trifluoroethylamine,
2-fluoroethylamine,
ethylenediamine,
2-methylaminoethylamine,
2-dimethylaminoethylamine,
1,1-dimethylhydrazine,
cyanamide,
3-aminopropionitrile,
guanidine and
methylguanidine, respectively, and there is thereby produced
3-(cyclobutylamino)-4-{2-[(5-dimethylaminomethyl-2-furyl)methylthio]ethylamino}-1,2,5-thiadiazole 1,1-dioxide,
3-[(cyclobutyl)methylamino]-4-{2-[(5-dimethylaminomethyl-2-furyl)methylthio]ethylamino}-1,2,5-thiadiazole 1,1-dioxide,
3-{2-[(5-dimethylaminomethyl-2-furyl)methylthio]ethylamino}-4-(2-hydroxyethylamino)-1,2,5-thiadiazole 1,1-dioxide,
3-{2-[(5-dimethylaminomethyl-2-furyl)methylthio]ethylamino}-4-(2-methylthioethylamino)-1,2,5-thiadiazole 1,1-dioxide,
3-{2-[(5-dimethylaminomethyl-2-furyl)methylthio]ethylamino}-4-(2,2,2-trifluoroethylamino)-1,2,5-thiadiazole 1,1-dioxide,
3-{2-[(5-dimethylaminomethyl-2-furyl)methylthio]ethylamino}-4-(2-fluoroethylamino)-1,2,5-thiadiazole 1,1-dioxide,
3-(2-aminoethylamino)-4-{2-[(5-dimethylaminomethyl-2-furyl)methylthio]ethylamino}-1,2,5-thiadiazole 1,1-dioxide,
3-{2-[(5-dimethylaminomethyl-2-furyl)methylthio]ethylamino}-4-(2-methylaminoethylamino)-1,2,5-thiadiazole 1,1-dioxide.
3-{2-[(5-dimethylaminomethyl-2-furyl)methylthio]ethylamino}-4-(2-dimethylaminoethylamino)-1,2,5-thiadiazole 1,1-dioxide,
3-{2-[(5-dimethylaminomethyl-2-furyl)methylthio]ethylamino}-4-(2,2-dimethylhydrazino)-1,2,5-thiadiazole 1,1-dioxide,
3-cyanoamino-4-{2-[(5-dimethylaminomethyl-2-furyl)methylthio]ethylamino}-1,2,5-thiadiazole 1,1-dioxide,
3-(3-cyanopropylamino)-4-{2-[(5-dimethylaminomethyl-2-furyl)methylthio]ethylamino}-1,2,5-thiadiazole 1,1-dioxide,
3-{2-[(5-dimethylaminomethyl-2-furyl)methylthio]ethylamino}-4-guanidino-1,2,5-thiadiazole 1,1-dioxide,
3-{2-[(5-dimethylaminomethyl-2-furyl)methylthio]ethylamino}-4-(N'-methyl)guanidino-1,2,5-thiadiazole 1,1-dioxide.

EXAMPLE 31

3-{2-[(2-Guanidinothiazol-4-yl)methylthio]ethylamino}-4-methylamino-1,2,5-thiadiazole 1,1-dioxide A solution of 2-[(2-guanidinothiazol-4-yl)methylthio]ethylamine (from the dihydrochloride, 4.27 g; 14.0 mmoles) in 30 ml of methanol was added to a well stirred suspension of 3,4-dimethoxy-1,2,5-thiadiazole 1,1-dioxide (2.50 g; 14.0 mmoles) in 250 ml of methanol at 10°. After 15 minutes at 10°, the solution was cooled to 1° in a cooling bath and anhydrous methylamine was bubbled into the solution for 10 minutes. The reaction mixture was evaporated under reduced pressure and the residue placed on 60 g of silica gel and chromatographed using a gradient elution of methylene chloride-methanol. The appropriate fraction containing 4.53 g of product was placed on 80 g of aluminum oxide and rechromatographed using a gradient elution of ethyl acetate-methanol. The appropriate fractions were combined and evaporated to give a foam which crystallized from methanol to yield (2.38 g) of the title compound, mp 196°–198° (dec).

Anal. Calcd for $C_{10}H_{16}N_8O_2S_3$: Cl, 31.90; H, 4.28; N, 29.77; S, 25.55. Found: C, 31.85; H, 4.24; N, 29.79; S, 25.45.

EXAMPLE 32

3-{2-[(2-Guanidinothiazol-4-yl)methylthio]ethylamino}-4-(2-propynyl)amino-1,2,5-thiadiazole 1,1-dioxide A solution of 2-[(2-guanidinothiazol-4-yl)methylthio]ethylamine (from the dihydrochloride, 3.42 g; 11.2 mmoles) in 25 ml of methanol was added to a well stirred cold (8°) suspension of 3,4-dimethoxy-1,2,5-thiadiazole 1,1-dioxide (2.0 g; 11.2 mmoles) in 200 ml of methanol. After 15 minutes at 8°–10°, the solution was cooled to 1° in an ice-bath and a solution of 6.0 ml 2-propynylamine in 15 ml of methanol was added. The ice-bath was removed and stirring was continued for 15 minutes. The reaction mixture was evaporated under reduced pressure and the residue placed on 50 g of silica gel and chromatographed using a gradient elution of methylene chloride-methanol. Two of the fractions yielded crystalline product (1.74 g) from methanol. The product was dissolved in hot methanol, filtered through Celite, cooled and filtered to yield the title compound, mp 176°–178°.

Anal. Calcd for $C_{12}H_{16}N_8O_2S_3$: C, 35.99; H, 4.03; N, 27.98; S, 24.02. Found: C, 35.82; H, 4.12; N, 28.41; S, 24.28.

EXAMPLE 33

3-{2-[(2-Dimethylaminomethyl-4-thiazolyl)methylthio]ethylamino}-4-methylamino-1,2,5-thiadiazole 1,1-dioxide A. N-Carbophenoxy-N-methylaminoacetonitrile To a suspension of methylaminoacetonitrile hydrochloride (100 g; 0.94 mole) in 1 liter of methylene chloride (cooled in an ice-water bath) was added triethylamine (260 ml, 1.88 moles) and a solution of phenyl chloroformate (155.0 g; 0.99 mole) in 500 ml of methylene chloride. The reaction mixture was heated at reflux temperature for 18 hours, then evaporated under reduced pressure to give a semi-solid which was triturated with 1 liter of diethyl ether and filtered. The filtrate was evaporated under reduced pressure and the residual oil was vacuum distilled to yield the title compound (123 g), bp 111°–113°/0.25 mm Hg; the NMR spectrum (60 MHz) in CDCl$_3$ gave the following resonances δ: 7.23 (m, 5H); 4.30 (s, 2H); 3.13 (s, 3H).

B. (N-Carbophenoxy-N-methylamino)thioacetamide

A solution of N-carbophenoxy-N-methylaminoacetonitrile (131.0 g; 0.69 mole) [prepared in Step A] and thioacetamide (57.1 g; 0.71 mole) in 917 ml of dry DMF was treated with HCl gas until an exothermic reaction took place, and then heated on a steam bath for 20 minutes. The reaction mixture was partially evaporated under reduced pressure to remove some of the solvent, then made basic with saturated aqueous NaHCO$_3$ solution and partitioned between ether and water. The aqueous phase was extracted with ether and the combined ether phase was washed with water, saturated aqueous NaCL solution and dried. Filtration and evaporation of the solvent gave an oil which was triturated with methylcyclohexane to give the product as a solid. Recrystallization from isopropyl alcohol yielded the title compound, mp 101°–103°.

Anal. Calcd $C_{10}H_{12}N_2O_2S$: C, 53.55; H, 5.40; N, 12.49; S, 14.30. Found: C, 53.65; H, 5.51; N, 12.69; S, 14.41.

C. 4-Chloromethyl-2-(N-carbophenoxy-N-methylamino)-methylthiazole

To a cooled solution of (N-carbophenoxy-N-methylamino)thioacetamide (1.0 g; 4.46 mmoles) and dry pyridine (0.36 ml, 4.46 mmoles) in 6 ml of absolute ethanol was added a solution of 1,3-dichloropropanone (0.57 g; 4.49 mmoles) in 3 ml of absolute ethanol. The mixture was heated at reflux temperature for 1.5 hours, then evaporated under reduced pressure and the oil residue partitioned between ether and water. The aqueous layer was extracted with ether and the combined ether phase was washed with water, saturated aqueous sodium chloride solution and dried. Filtration and evaporation yielded 1.02 g of the title compound as a viscous oil; TLC [silica/CH$_2$Cl$_2$:CH$_3$CN (85:15)] gave Rf=0.82. The NMR spectrum (60 MHz) in CDCl$_3$ gave the following resonances δ: 7.16 (m, 6H); 4.77 (broad s, 2H); 4.60 (s, 2H); 3.07 (broad s, 3H).

D. 2-{[2-(N-Carbophenoxy-N-methylamino)methyl-4-thiazolyl]methylthio}ethylamine

To a solution of sodium methoxide (26.1 g; 0.48 mole) in 290 ml of absolute ethanol at 0° under a nitrogen atmosphere was added crysteamine hydrochloride (27.6 g; 0.24 mole) and an additional 218 ml of absolute ethanol. After stirring at 0° for 1 hour a solution of 4-chloromethyl-2-(N-carbophenoxy-N-methylamino)methylthiazole (72.5 g; 0.24 mole) in 218 ml of absolute ethanol was added over a 15 minute period. The reaction mixture was stirred at ambient temperature for 18 hours, filtered and evaporated under reduced pressure to give an oil which was partitioned between methylene chloride and water. The aqueous phase was extracted with methylene chloride and the combined organic phase was washed with water, dried, filtered and evaporated under reduced pressure to give the product (68.5 g) as an oil which was treated with fumaric acid (23.6 g) in n-propanol to give the salt (47.0 g). Recrystallization from absolute ethanol yielded the title compound as the fumarate salt, mp 145°–146°.

Anal. Calcd for $C_{15}H_{19}N_3O_2S_2 \cdot C_4H_4O_4$: C, 50.31; H, 5.11; N, 9.27; S, 14.14. Found: C, 50.02; H, 5.16; N, 9.47; S, 14.22.

E. 2-[(2-Dimethylaminomethyl-4-thiazolyl)methylthio]ethylamine

To a solution of 2-{[2-(N-Carbophenoxy-N-methylamino)methyl-4-thiazolyl]methylthio}ethylamine (0.50 g; 1.48 mmoles) [prepared in Step D] in 10 ml of dry tetrahydrofuran under a nitrogen atmosphere was added lithium aluminum hydride (0.17 g; 4.48 mmoles) and the mixture was heated at reflux temperature for 0.5 hour. An additional 10 ml of tetrahydrofuran was added and heating was continued for 3 hours. The reaction mixture was treated with 0.17 ml of H$_2$O, 0.17 ml of 15% aqueous NaOH and 0.51 ml of H$_2$O, and filtered through Celite and dried. The filtrate was filtered and evaporated under reduced pressure to give an oil which was dissolved in absolute ethanol, diluted with diethyl ether and acidified with dry HCl. The hydroscopic hydrochloride salt of the title compound was collected and partitioned between aqueous 2.5 N NaOH and methylene chloride. The organic phase was washed with water, dried and filtered. The filtrate was evaporated under reduced pressure to give the free base of the title compound as an oil (0.22 g; 0.95 mmole) which was combined with anhydrous oxalic acid (0.24 g; 1.90 mmole) in 30 ml of hot acetonitrile. The mixture was evaporated from hot absolute ethanol to yield the title compound the bis-oxalate, mp 168°–171°.

Anal. Calcd for $C_9H_{17}N_3O_4S_2.2C_2H_2O_4$: C, 37.95; H, 5.15; N, 10.21; S, 15.59. Found: C, 37.95; H, 5.04; N, 9.81; S, 15.27.

F. 3-{2-[(2-Dimethylaminomethyl-4-thiazolyl)methylthio]ethylamino}-4-methylamino-1,2,5-thiadiazole 1,1-dioxide To a cooled (6°) suspension of 3,4-dimethoxy-1,2,5-thiadiazole 1,1-dioxide (0.74 g; 4.17 mmoles) in 80 ml of methanol was added dropwise over a period of 45 minutes a solution of 2-[(2-dimethylaminomethyl-4-thiazolyl)methylthio]ethylamine (0.96 g; 4.17 mmoles) [prepared in Step E] to give 3-{2-[(2-dimethylaminomethyl-4-thiazolyl)methylthio]ethylamino}-4-methoxy-1,2,5-thiadiazole 1,1-dioxide, Rf=0.64 [Silica/$CH_2Cl_2$:$CH_3OH$ (9:1)]. The temperature was maintained at 6° and anhydrous methylamine was bubbled into the solution for 8 minutes. The reaction mixture was evaporated under reduced pressure and the residue placed on 80 g of silica gel and chromatographed using a gradient elution of methylene chloride-methanol. The appropriate fractions were combined and the residue was rechromatographed on 25 g of aluminum oxide using a gradient elution of methylene chloride-methanol to give 0.52 g of product. Recrystallization from isopropyl alcohol/ether yielded the title compound, mp 144°–148° (foaming).

Anal. Calcd for $C_{12}H_{20}N_6O_2S_3$: C, 38.28; H, 5.35; N, 22.32; S, 25.55. Found: C, 37.89; H, 5.43; N, 22.19; S, 25.40.

EXAMPLE 34

3-{2-[(2-Dimethylaminomethyl-4-thiazolyl)methylthio]ethylamino}-4-methylamino-1,2,5-thiadiazole 1-oxide A. N-Carbethoxy-N-methylaminoacetonitrile Triethylamine (5.2 ml; 37.6 mmoles) was added to a suspension of methylaminoacetonitrile hydrochloride (2.0 g; 18.8 mmoles) in 20 ml of methylene chloride. The resulting suspension was cooled in an ice-bath and a solution of ethyl chloroformate (2.14 g; 19.8 mmoles) in 10 ml of methylene chloride was added over a 0.5 hour period, and the mixture was then heated at reflux temperature for 18 hours. The reaction mixture was evaporated under reduced pressure to give a semi-solid residue which was triturated with diethyl ether and filtered, and the filtrate was evaporated under reduced pressure to yield the title compound as an oil (2.2 g), bp 96°–98°/5.2 mm Hg.

B. (N-Carbethoxy-N-methylamino)thioacetamide

A solution of N-carbethoxy-N-methylaminoacetonitrile (9.8 g; 6.9 mmoles) [prepared in Step A], and thioacetamide (10.35 g; 13.8 mmoles) in 175 ml of dry DMF was treated with hydrogen chloride gas until a vigorous exothermic reaction took place, and then was heated on a steam bath for 15 minutes. The reaction mixture was made basic with saturated $NaHCO_3$ solution, and then extracted with ether, washed with water and dried. The etheral phase was evaporated under reduced pressure to give a solid residue which was dissolved in methylene chloride and washed with water. The organic phase was dried, filtered and evaporated under reduced pressure to give product (2.5 g). Recrystallization from ethyl acetate-hexane yielded the title compound, mp 91°–93°.

Anal Calcd for $C_6H_{12}N_2O_2S$: C, 40.89; H, 6.87; N, 15.96; S, 18.92. Found: C, 40.73; H, 6.85; N, 16.13; S, 18.86.

C. 2-(N-Carbethoxy-N-methylamino)methyl-4-carbethoxythiazole

To a solution of (N-carbethoxy-N-methylamino)thioacetamide (30.7 g; 0.17 mole) [prepared in Step B] in 180 ml of absolute ethanol was added a solution of ethyl bromopyruvate (25.0 ml; 0.20 mole) in 130 ml of absolute ethanol. The reaction mixture was heated at reflux temperature for 17 hours and then evaporated under reduced pressure, and the residue was partitioned between ether and water. The organic layer was washed with water and saturated sodium chloride solution, dried, filtered and evaporated under reduced pressure to give an oil which was placed on silica gel and chromatographed using diethyl ether as the eluting solvent. The appropriate fractions yielded the title compound as an oil; TLC [Silica/$CH_2Cl_2$:$CH_3CN$ (85.15)] gave Rf=0.50. The NMR spectrum (60 MHz) in $d_6$ dimethyl sulfoxide gave the following resonances δ: 8.49 (s, 1H); 4.79 (s, 2H); 4.23 (m, 4H); 3.00 (s, 3H); 1.30 (q, 6H).

D. 2-Dimethylaminomethyl-4-hydroxymethylthiazole

To a cooled suspension of lithium aluminum hydride (8.4 g; 0.22 mole) in 80 ml of dry tetrahydrofuran was added a solution of 2-(N-carbethoxy-N-methylamino)methyl-4-carbethoxythiazole (20.0 g; 0.07 mole) [prepared in Step C] in 160 ml of dry tetrahydrofuran over a 1 hour period. The reaction mixture was heated at reflux temperature for 8 hours, then cooled and decomposed with $Na_2SO_4$ and 40% aqueous potassium hydroxide. The mixture was filtered, dried and evaporated under reduced pressure to give 4.2 g of the title compound as an oil; TLC (aluminum oxide/$CH_3CN$) gave RF=0.45. The NMR spectrum (60 MHz) in $CDCl_3$ gave the following resonances δ: 7.17 (s, 1H); 4.73 (d, 2H); 3.43 (s, 2H); 3.35 (s, 6H).

E. 2-[(2-Dimethylaminomethyl-4-thiazolyl)methylthio]ethylamine

When 2-dimethylaminomethyl-4-hydroxymethylthiazole [prepared in Step D] is reacted with thionyl chloride and the resultant 2-dimethylaminomethyl-4-chloromethylthiazole is reacted with an equimolar amount of cysteamine hydrochloride and two equivalents of base according to the general procedure of Example 33, Step D, the title compound is thereby produced.

F. 3-{2-[(2-Dimethylaminomethyl-4-thiazolyl)methylthio]ethylamino}-4-methylamino-1,2,5-thiadiazole 1-oxide When a methanol suspension of 3,4-dimethoxy-1,2,5-thiaziazole 1-oxide [prepared in Example 4, Step A] is reacted with an equimolar amount of 2-[(2-dimethylaminomethyl-4-thiazolyl)methylthio]ethylamine [prepared in Example 33, Step E] and the resulting 3-{2-[(2-dimethylaminomethyl-4-thiazolyl)methylthio]ethylamino}-4-methoxy-1,2,5-thiadiazole 1-oxide is treated with methylamine, the title compound is thereby produced.

EXAMPLE 35

3-Amino-4-{2-[(2-guanidinothiazol-4-yl)methylthio]ethylamino}-1,2,5-thiadiazole 1,1-dioxide A solution of 2-[(2-guanidinothiazol-4-yl)methylthio]ethylamine (2.75 g; 11.9 mmoles) [obtained by neutralization of 2-[(2-guanidinothiazol-4-yl)methylthio]ethylamine dihydrochloride (4.0 g; 13.0 mmoles) with 2.5 N aqueous sodium hydroxide and extraction with ethyl acetate]in 30 ml of methanol was added over a 1 hour period to a well stirred, cold (0°) suspension of 3,4-dimethoxy-1,2,5-thiadiazole 1,1-dioxide (2.12 g; 11.9 mmoles) in 220 ml of methanol. While maintaining the temperature at 0°, anhydrous ammonia was bubbled into the solution for 6 minutes and stirring was continued at ambient temperature for 0.5 hour. The reaction mixture was evaporated under reduced pressure and the residue placed on 120 g of silica gel and chromatographed using a gradient elution of methylene chloride-methanol. The appropriate fractions were combined and evaporated, and the residue was rechromatographed on 40 g of silica gel using a gradient elution of methylene chloride-methanol. The appropriate fractions were combined, concentrated under vacuum, filtered and dried under high vacuum to yield the title compound, mp 134°-149° (foaming); the NMR spectrum (100 MHz) in $d_6$ dimethyl sulfoxide/$D_2O$/DCl gave the following resonances δ: 7.16 (s, 1H); 3.84 (s, 2H); 3.52 (t, 2H); 2.75 (t, 2H); and showed the presence of approximately 1.2 moles of methanol.

Anal. Calcd for $C_9H_{14}N_8O_2S_3 \cdot 1.2CH_3OH$: C, 30.56; H, 4.72; N, 27.95; S, 23.99. Found (corr. for 1.31% $H_2$): C, 30.19; H, 4.32; N, 27.91; S, 24.71.

EXAMPLE 36

3-{2-[(2-Guanidinothiazol-4-yl)methylthio]ethylamino}-4-(2-hydroxyethylamino)-1,2,5-thiadiazole 1,1-dioxide To a well stirred suspension of 3,4-dimethoxy-1,2,5-thiadiazole 1,1-dioxide (2.05 g; 11.5 mmoles) in 200 ml of dry methanol at 3° was added, dropwise over 30 minutes, a solution of 2-[(2-guanidinothiazol-4-yl)methylthio]ethylamine (from the dihydrochloride; 3.5 g; 11.5 mmoles) in 40 ml of dry methanol. After 15 minutes at 3°, a solution of ethanolamine (1.03 ml, 17.3 mmoles) in 10 ml of methanol was rapidly added dropwise and stirred for 15 minutes. The reaction mixture was evaporated under reduced pressure to give the product as a friable foam that crystallized from methanol. Two recrystallizations from methanol yielded the title compound, mp=slowly resinified starting at 115°, decomposed starting at 175°.

Anal. Calcd for $C_{11}H_{18}N_8O_3S_3$: C, 32.50; H, 4.46; N, 27.57; S, 23.66. Found (corr. for 3.85% $H_2O$): C, 32.77; H, 4.21; N, 27.90; S, 24.39.

EXAMPLE 37

3-(2,3-Dihydroxypropylamino)-4-{2-[(2-guanidinothiazol-4-yl)methylthio]ethylamino}-1,2,5-thiadiazole 1,1-dioxide When a methanolic solution of 2-[(2-guanidinothiazol-4-yl)methylthio]ethylamine is reacted with 3,4-dimethoxy-1,2,5-thiadiazole 1,1-dioxide by the procedure of Example 31 and the resultant 3-methoxy-4-{2-[(2-guanidinothiazol-4-yl)methylthio]ethylamino}-1,2,5-thiadiazole 1,1-dioxide is treated with 3-amino-1,2-propanediol, the title compound is thereby produced.

EXAMPLE 38

3-Methylamino-4-{2-[(thiazol-2-yl)methylthio]ethylamino}-1,2,5-thiadiazole 1,1-dioxide When a methanolic solution of 2-[(thiazol-2-yl)methylthio]ethylamine [prepared according to the procedure described in U.S. Pat. No. 3,950,333] is reacted with 3,4-dimethoxy-1,2,5-thiadiazole 1,1-dioxide and the resultant 3-methoxy-4-{2-[(thiazol-2-yl)methylthio]ethylamino}-1,2,5-thiadiazole 1,1-dioxide treated with methylamine according to the general procedure described in Example 31, the title compound is thereby produced.

EXAMPLE 39

When 2-chloromethyl-4-methylthiazole [prepared by the reaction of thionyl chloride and 2-hydroxymethyl-4-methylthiazole, which itself is prepared according to the procedure of *J. Chem. Soc.*, (Suppl. Issue No. 1), S106-111 (1966) or *Acta Chem.Scand.*, 20, 2649 (1966)] is reacted with cysteamine hydrochloride and about two equivalents of a strong base such as sodium methoxide, and the resultant amine is treated with 3,4-dimethoxy-1,2,5-thiadiazole 1,1-dioxide, there is produced 3-methoxy-4-{2-[(4-methylthiazol-2-yl)methylthio]ethylamino}-1,2,5-thiadiazole 1,1-dioxide. When the latter compound is reacted with methylamine according to the general procedure of Example 31, there is produced 3-methylamino-4-{2-[(4-methylthiazol-2-yl)methylthio]ethylamino}-1,2,5-thiadiazole 1,1-dioxide.

When the above procedure is repeated, except that the 2-chloromethyl-4-methylthiazole utilized therein is replaced by an equimolar amount of the chloromethylthiazoles prepared by reacting thionyl chloride with
2-amino-4-hydroxymethylthiazole[1],
2-hydroxymethyl-4,5-dimethylthiazole[2],
4-hydroxymethyl-2-methylthiazole[3],
4-hydroxymethyl-2-chlorothiazole[4],
5-hydroxymethyl-2-methylthiazole[5],
5-hydroxymethyl-4-methylthiazole[6],
4-hydroxymethylthiazole[7] and
4-dimethylaminomethyl-2-hydroxymethylthiazole[8], respectively, there is thereby produced
3-{2-[(2-aminothiazol-4-yl)methylthio]ethylamino}-4-methylamino-1,2,5-thiadiazole 1,1-dioxide,
3-{2-[(4,5-dimethylthiazol-2-yl)methylthio]ethylamino}-4-methylamino-1,2,5-thiadiazole 1,1-dioxide,
3-{2-[(2-methylthiazol-4-yl)methylthio]ethylamino}-4-methylamino-1,2,5-thiadiazole 1,1-dioxide,
3-{2-[(2-chlorothiazol-4-yl)methylthio]ethylamino}-4-methylamino-1,2,5-thiadiazole 1,1-dioxide,
3-{2-[(2-methylthiazol-5-yl)methylthio]ethylamino}-4-methylamino-1,2,5-thiadiazole 1,1-dioxide,
3-{2-[(4-methylthiazol-5-yl)methylthio]ethylamino}-4-methylamino-1,2,5-thiadiazole 1,1-dioxide,
3-{2-[(thiazol-4-yl)methylthio]ethylamino}-4-methylamino-1,2,5-thiadiazole 1,1-dioxide and
3-{2-[(4-dimethylaminomethylthiazol-2-yl)methylthio]ethylamino}-4-methylamino-1,2,5-thiadiazole 1,1-dioxide, respectively.

The above starting materials are prepared according to the procedures described in the following publications:

(1) *J. Am. Chem. Soc.*, 68, 2155 (1946);

(2) *Helv. Chim. Acta*, 31, 652 (1948);
(3) and (5) *Zh. Obshch. Khim.*, 32, 570 (1962) [C. A., 58, 2525b (1963)];
(4) *Rev. Roumaine Chim.*, 10, 897 (1965) [C. A., 64, 8164b (1966)];
(6) *J. Am. Chem. Soc.*, 67, 400 (1945);
(7) *Zh. Obshch. Khim.*, 27, 726 (1957) [C. A., 51, 16436h (1957)];
(8) An ethanol solution of dimethylamine is reacted with 2-bromo-4-chloromethylthiazole, prepared according to reference (4) above, and the resultant 2-bromo-4-dimethylaminomethylthiazole is treated with a strong base and formaldehyde according to the general procedure described in *Acta. Chem. Scand.*, 20, 2649 (1966), to give the desired 4-dimethylaminomethyl-2-hydroxymethylthiazole.

EXAMPLE 40

3-{3-[(2-Dimethylaminomethyl-4-thiazolyl)methylthio]propylamino}-4-methylamino-1,2,5-thiadiazole 1,1-dioxide When 2-dimethylaminomethyl-4-hydroxymethylthiazole [prepared in Example 34, Step D] is reacted with 3-mercaptopropylamine hydrochloride [prepared according to the procedure described in *J. Org. Chem.*, 27, 2846 (1962)] in aqueous hydrobromic acid (48%), and the resultant amine is successively treated with 3,4-dimethoxy-1,2,5-thiadiazole 1,1-dioxide and excess methylamine as in the general procedure of Example 31, the title compound is produced.

EXAMPLE 41

3-{2-[(2-Guanidinothiazol-4-yl)methylthio]propylamino}-4-amino-1,2,5-thiadiazole 1-oxide When a methanolic solution of 2-[(guanidinothiazol-4-yl)methylthio]propylamine is reacted with 3,4-dimethoxy-1,2,5-thiadiazole 1-oxide [prepared in Example 4, Step A], and the resultant 3-{2-[(2-guanidinothiazol-4-yl)methylthio]propylamino}-4-methoxy-1,2,5-thiadiazole 1-oxide is treated with excess ammonia by the procedure in Example 35, the title compound is thereby produced.

EXAMPLE 42

3-{2-[(2-Guanidinothiazol-4-yl)methylthio]ethylamino}-4-methylamino-1,2,5-thiadiazole 1,1-dioxide Reaction of a methanolic suspension of 3,4-dimethoxy-1,2,5-thiadiazole 1,1-dioxide with one equivalent of methylamine and treatment of the resultant 3-methoxy-4-methylamino-1,2,5-thiadiazole 1,1-dioxide with one equivalent of 2-[(2-guanidinothiazol-4-yl)methylthio]ethylamine yields the title compound, which is identical to the product obtained in Example 31.

EXAMPLE 43

3-{2-[(2-Guanidinothiazol-4-yl)methylthio]ethylamino}-4-methylamino-1,2,5-thiadiazole 1,1-dioxide When a solution of 3-methylamino-4-(2-mercaptoethyl)-1,2,5-thiadiazole 1,1-dioxide [prepared in Example 25, Step A] is reacted with 4-chloromethyl-2-guanidinothiazole hydrochloride and a strong base, the title compound is thereby produced, which is identical to the product obtained in Example 31.

EXAMPLE 44

3-{2-[(2-Guanidinothiazol-4-yl)methylthio]ethylamino}-4-hydroxy-1,2,5-thiadiazole 1,1-dioxide When 3,4-dimethoxy-1,2,5-thiadiazole 1,1-dioxide is reacted with one equivalent of 2-[(2-guanidinothiazol-4-yl)methylthio]ethylamine and the resultant 3-{2-[(2-guanidinothiazol-4-yl)methylthio]ethylamino}-4-methoxy-1,2,5-thiadiazole 1,1-dioxide is reacted with sodium hydroxide according to the procedure described in Example 17, Step B, the title compound is produced.

EXAMPLE 45

3-{2-[(2-Dimethylaminomethyl-4-thiazolyl)methylthio]ethylamino}-4-methylamino-1,2,5-thiadiazole 1,1-dioxide Reaction of a methanolic suspension of 3,4-dimethoxy-1,2,5-thiadiazole 1,1-dioxide with one equivalent of methylamine and treatment of the resultant 3-methoxy-4-methylamino-1,2,5-thiadiazole 1,1-dioxide with one equivalent of 2-[(2-dimethylaminomethyl-4-thiazolyl)methylthio]ethylamine [prepared in Example 33, Step E], produces the title compound which is identical to the product prepared in Example 33.

EXAMPLE 46

3-{2-[(2-Dimethylaminomethyl-4-thiazolyl)methylthio]ethylamino}-4-methylamino-1,2,5-thiadiazole 1,1-dioxide Reaction of 3-methylamino-4-(2-mercaptoethyl)-1,2,5-thiadiazole 1,1-dioxide [prepared in Example 25, Step A] with about one equivalent of 2-dimethylaminomethyl-4-hydroxymethylthiazole [prepared in Example 34, Step D] in concentrated hydrochloric acid, and then made basic and worked up, produces the title compound which is identical to the product prepared in Example 33.

EXAMPLE 47

3-{2-[(2-Dimethylaminomethyl-4-thiazolyl)methylthio]ethylamino}-4-hydroxy-1,2,5-thiadiazole 1,1-dioxide When a solution of 3-{2-[(2-dimethylaminomethyl-4-thiazolyl)methylthio]ethylamino}-4-methoxy-1,2,5-thiadiazole 1,1-dioxide [prepared according to the procedure described in Example 33, Step F] is reacted with sodium hydroxide according to the procedure described in Example 17, Step B, the title compound is produced.

EXAMPLE 48

3-Amino-4-{2-[(2-dimethylaminomethyl-4-thiazolyl)methylthio]ethylamino}-1,2,5-thiadiazole 1-oxide When a methanolic solution of 3-{2-[(2-dimethylaminomethyl-4-thiazolyl)methylthio]ethylamino}-4-methoxy-1,2,5-thiadiazole 1-oxide [prepared from 3,4-dimethoxy-1,2,5-thiadiazole 1-oxide by the general procedure described in Example 34, Step F] is reacted with anhydrous ammonia according to the general procedure described in Example 35, the title compound is thereby produced.

EXAMPLE 49

3-{2-[(2-Dimethylaminomethyl-4-thiazolyl)methylthio]ethylamino}-4-methylamino-1,2,5-thiadiazole 1-oxide Reaction of 3-methylamino-4-(2-mercaptoethyl)-1,2,5-thiadiazole 1-oxide [prepared by reacting 3,4-dimethoxy-1,2,5-thiadiazole 1-oxide with 2-aminoethanethiol and methylamine according to the procedure described in Example 25, Step A] with about one equivalent of 2-dimethylaminomethyl-4-hydroxymethylthiazole [prepared in Example 34, Step D], produces the title compound.

EXAMPLE 50

3-Amino-4-[4-(2-guanidinothiazol-4-yl)butylamino]-1,2,5-thiadiazole 1-oxide

When a methanolic solution of 3,4-dimethoxy-1,2,5-thiadiazole 1-oxide is successively treated with 4-(2-guanidinothiazol-4-yl)butylamine [prepared according to the procedure described in U.S. Pat. No. 4,165,377] and excess anhydrous ammonia according to the general procedure described in Example 35, the title compound is thereby produced.

EXAMPLE 51

3-{2-[(5-Dimethylaminomethyl-2-furyl)methylthio[ethylamino}-4-hydrazino-1,2,5-thiadiazole 1,1-dioxide A solution of 2-[(5-dimethylaminomethyl-2-furyl)methylthio]ethylamine (2.41 g; 11.2 mmoles) in 30 ml of dry methanol was added dropwise over a period of 45 minutes to a well stirred cold (ice-water bath) suspension of 3,4-dimethoxy-1,2,5-thiadiazole 1,1-dioxide (2.0 g; 11.2 mmoles) in 250 ml of methanol. After stirring at 0° for 15 minutes, a solution of anhydrous hydrazine (1.8 g; 56.13 mmoles) in 30 ml of dry methanol was added all at once, and stirring was continued for 30 minutes. The reaction mixture was evaporated under reduced pressure and the solid residue was treated with chloroform and filtered to give 3.28 g of the title compound, mp 170° (dec.).

EXAMPLE 52

3-Methylamino-4-{2-[(2-pyridyl)methylthio]ethylamino}-1,2,5-thiadiazole 1,1-dioxide A solution of 2-[(2-pyridyl)methylthio]ethylamine (from the dihydrobromide, 3.5 g; 10.6 mmoles) [prepared according to the procedure described in Belgian Pat. No. 779,775] in 25 ml of dry methanol was added dropwise over 30 minutes to a well stirred suspension of 3,4-dimethoxy-1,2,5-thiadiazole 1,1-dioxide in 200 ml of dry methanol that was cooled to 0°–5° in an ice-water bath. After stirring the cold solution for 15 minutes, anhydrous methylamine was bubbled into the solution for 15 minutes. The reaction mixture was stirred at ambient temperature for 45 minutes, evaporated under reduced pressure and the residue crystallized with methanol. Two recrystallizations from methanol yielded the title compound, mp 168°–171°.

Anal. Calcd for $C_{11}H_{15}N_5O_2S_2$: C, 42.15; H, 4.82; N, 22.35; S, 20.46. Found: C, 42.07; H, 4.75; N, 22.28; S, 20.73.

EXAMPLE 53

3-{2-[(3-Chloro-2pyridyl)methylthio]ethylamino}-4-methylamino-1,2,5-thiadiazole 1,1-dioxide When a methanolic solution of 3,4-dimethoxy-1,2,5-thiadiazole 1,1-dioxide is successively treated with 2-[(3-chloro-2-pyridyl)methylthio]ethylamine [prepared according to the procedure described in U.S. Pat. No. 4,024,260] and methylamine according to the general procedure of Example 52, the title compound is thereby produced.

EXAMPLE 54

3-{2-[(6-Dimethylaminomethyl-2-pyridyl)methylthio]ethylamino}-4-methylamino-1,2,5-thiadiazole 1,1-dioxide When a methanolic solution of 3,4-dimethoxy-1,2,5-thiadiazole 1,1-dioxide is successively treated with an equimolar amount of 2-[(6-dimethylaminomethyl-2-pyridyl)methylthio]ethylamine [prepared in Example 136, Step C] and excess methylamine, the title compound is thereby produced.

EXAMPLE 55

The general procedure of Example 52 is repeated except that the 2-[(2-pyridyl)methylthio]ethylamine utilized therein is replaced by an equimolar amount of
2-[(3-bromo-2-pyridyl)methylthio]ethylamine,
2-[(3-cyano-2-pyridyl)methylthio]ethylamine,
2-[(3-hydroxy-2-pyridyl)methylthio]ethylamine,
2-[(3-methoxy-2-pyridyl)methylthio]ethylamine,
2-[(3-ethoxy-2-pyridyl)methylthio]ethylamine,
2-[(3-methyl-2-pyridyl)methylthio]ethylamine and
2-[(3-amino-2-pyridyl)methylthio]ethylamine, respectively,
[prepared according to the general procedures described in Belgian Pat. Nos. 779,775, 804,144 and 844,504] and there is thereby produced
3-{2-[(3-bromo-2-pyridyl)methylthio]ethylamino}-4-methylamino-1,2,5-thiadiazole 1,1-dioxide,
3-{2-[(3-cyano-2-pyridyl)methylthio]ethylamino}-4-methylamino-1,2,5-thiadiazole 1,1-dioxide,
3-{2-[(3-hydroxy-2-pyridyl)methylthio]ethylamino}-4-methylamino-1,2,5-thiadiazole 1,1-dioxide,
3-{2-[(3-methoxy-2-pyridyl)methylthio]ethylamino}-4-methylamino-1,2,5-thiadiazole 1,1-dioxide,
3-{2-[(3-ethoxy-2-pyridyl)methylthio]ethylamino}-4-methylamino-1,2,5-thiadiazole 1,1-dioxide,
3-{2-[(3-methyl-2-pyridyl)methylthio]ethylamino}-4-methylamino-1,2,5-thiadiazole 1,1-dioxide and
3-{2-[(3-amino-2-pyridyl)methylthio]ethylamino}-4-methylamino-1,2,5-thiadiazole 1,1-dioxide, respectively.

EXAMPLE 56

3-{2-[(3-Chloro-2-pyridyl)methylthio]ethylamino}-4-{2-[(5-dimethylaminomethyl-2-furyl)methylthio]ethylamino}-1,2,5-thiadiazole 1,1-dioxide When a methanolic solution of 3,4-dimethoxy-1,2,5-thiadiazole 1,1-dioxide is successively treated with 2-[(5-dimethylaminomethyl-2furyl)methylthio]ethylamine and 2-[(3-chloro-2-pyridyl)methylthio]ethylamine, the title compound is thereby produced.

EXAMPLE 57

3-{2-[(6-Dimethylaminomethyl-2-pyridyl)methylthio]-ethylamino}-4-methylamino-1,2,5-thiadiazole 1-oxide When a methanolic solution of 3,4-dimethoxy-1,2,5-thiadiazole 1-oxide [obtained from Example 4, Step A] is successively treated with an equimolar amount of 2-[(6-dimethylaminomethyl-2-pyridyl)methylthio]-ethylamine [prepared in Example 136, Step C] and an excess of methylamine, the title compound is thereby produced.

EXAMPLE 58

3-{2-[(4-Methyl-1,2,5-oxadiazol-3-yl)methylthio]-ethylamino}-4-methylamino-1,2,5-thiadiazole 1,1-dioxide A. 3-Hydroxymethyl-4-methylfurazan To a stirred solution of 3-methyl-4-furazancarboxylic acid (27.0 g; 0.21 mole) in 180 ml of tetrahydrofuran (that was cooled in an ice-water bath) under a nitrogen atmosphere was added dropwise a 1.02 M solution of borane in tetrahydrofuran (825 ml; 0.84 mole). When the addition was completed, the mixture was stirred at ambient temperature overnight. After 20 hours, 6 N HCl was added dropwise until the evolution of hydrogen ceased and the reaction mixture was evaporated under reduced pressure. The residue was partitioned between methylene chloride and water, made basic with potassium carbonate and the combined methylene chloride extract was dried and evaporated under reduced pressure to give 21.0 g of product. Vacuum distillation yielded the title compound, bp 99°/1 mm Hg.

B. 2-[(4-Methyl-1,2,5-oxadiazol-3-yl)methylthio]-ethylamine

A solution of 3-hydroxymethyl-4-methylfurazan (2.49 g; 21.8 mmoles) [prepared in Step A] and 2-aminoethanethiol hydrochloride (2.48 g; 21.8 mmoles) in 60 ml of 48% aqueous hydrobromic acid was stirred and heated at reflux temperature for 23 hours and then at ambient temperature for 40 hours. The excess hydrobromic acid was removed under reduced pressure, and the oil residue was dissolved in isopropyl alcohol, filtered though Celite and the product was crystallized from the filtrate. Recrystallization from isopropyl alcohol yielded the title compound as the hydrobromide salt, mp 142°–143°.

C. 3-{2-[(4-Methyl-1,2,5-oxadiazol-3-yl)methylthio]-ethylamino}-4-methylamino-1,2,5-thiadiazole 1,1-dioxide When a methanolic suspension of 3,4-dimethoxy-1,2,5-thiadiazole 1,1-dioxide is successively treated with an equimolar amount of 2-[(4-methyl-1,2,5-oxadiazol-3-yl)methylthio]ethylamine [prepared in Step B] and excess methylamine by the general procedure of Example 2, the title compound is thereby produced.

EXAMPLE 59

3-{2-[(5-Dimethylaminomethyl-2-furyl)methylthio]-ethylamino}-4-{2-[(4-methyl-1,2,5-oxadiazol-3-yl)methylthio]ethylamino}-1,2,5-thiadiazole 1,1-dioxide When a methanolic solution of 3,4-dimethoxy-1,2,5-thiadiazole 1,1-dioxide is treated with 2-[(4-methyl-1,2,5-oxadiazol-3-yl)methylthio]ethylamine [prepared in Example 58, Step B] and 2-[(5-dimethylaminomethyl-2-furyl)methylthio]ethylamine, the title compound is thereby produced.

EXAMPLE 60

3-{2-[(5-Methyl-1,2,4-oxadiazol-3-yl)methylthio]-ethylamino}-4-methylamino-1,2,5-thiadiazole 1,1-dioxide A. 2-[(5-Methyl-1,2,4-oxadiazol-3-yl)methylthio]-ethylamine Cysteamine hydrochloride (3.03 g; 26.7 mmoles) was added in several portions over a period of 10 minutes to a stirred solution of sodium methylate (2.89 g; 53.4 mmoles) in 50 ml of methanol at 0°. After stirring for 70 minutes at 0°, a solution of 3-chloromethyl-5-methyl-1,2,4-oxadiazole (3.54 g; 26.7 mmoles) in 15 ml of methanol was added dropwise over a period of 15 minutes, and the reaction mixture was allowed to stir at ambient temperature for 16 hours. The mixture was filtered, evaporated and redissolved in isopropyl alcohol, then filtered and evaporated under reduced pressure to give the title compound (5.64 g) as a yellow oil. The NMR spectrum (60 MHz) in CDCl$_3$ gave the following resonances δ: 3.77 (s, 2H); 2.77 (m, 4H); 2.63 (s, 3H).

B. 3-{2-[(5-Methyl-1,2,4-oxadiazol-3yl)methylthio]-ethylamino}-4-methylamino-1,2,5-thiadiazole 1,1-dioxide When a methanolic suspension of 3,4-dimethoxy-1,2,5-thiadiazole 1,1-dioxide is treated successively with 2-[(5-methyl-1,2,4-oxadiazol-3-yl)methylthio]ethylamine [prepared in Step A] and methylamine, by the general procedure of Example 2, the title compound is thereby produced.

EXAMPLE 61

3-{2-[(2-Methyl-1,3,4-oxadiazol-5-yl)methylthio]-ethylamino}-4-methylamino-1,2,5-thiadiazole 1,1-dioxide A. 2-[(2-Methyl-1,3,4-oxadiazol-5-yl)methylthio]-ethylamine Cysteamine hydrochloride (1.13 g; 0.01 mole) was added to a stirred solution of sodium methylate (1.08 g; 0.02 mole) in 20 ml of methanol at 0° under an argon atmosphere. The mixture was stirred for 1 hour at 0° and the resultant suspension was added dropwise over a period of 25 minutes to a stirred solution of 2-methyl-5-chloromethyl-1,3,4-oxadiazole (1.32 g; 0.01 mole) [prepared by the procedure described in *Hel. Chim. Acta*, 55, 1979 (1972)] in 15 ml of methanol at 0°. The reaction mixture was stirred at ambient temperature for 45 minutes, concentrated to near dryness, and then diluted with methylene chloride, filtered and evaporated under reduced pressure to give the title compound (1.92 g) as a yellow oil. The NMR spectrum (60 MHz) in CDCl$_3$ gave the following resonances δ: 3.87 (s, 2H); 2.8 (m, 4H); 2.53 (s, 3H).

B. 3-{2-[(2-Methyl-1,3,4-oxadiazol-5-yl)methylthio]-ethylamino}-4-methylamino-1,2,5-thiadiazole 1,1-dioxide When a suspension of 3,4-dimethoxy-1,2,5-thiadiazole 1,1-dioxide is treated with an equimolar amount of 2-[(2-methyl-1,3,4-oxadiazol-5-yl)methylthio]ethylamine [prepared in Step A] and an excess of methylamine by the general procedure described in Example 2, the title compound is thereby produced.

EXAMPLE 62

3-{2-[(2-Dimethylamino-1,3,4-oxadiazol-5-yl)methylthio]ethylamino}-4-methylamino-1,2,5-thiadiazole 1,1-dioxide When 2-dimethylamino-5-ethoxycarbonyl-1,3,4-oxadiazole [prepared according to the procedure described in Org. Magn. Resonance, 6, 144 (1974)] is hydrolyzed and reduced with borane as described in Example 58, Step A, and then is reacted with cysteamine according to the procedure described in Example 60, Step A, there is produced 2-[(2-dimethylamino-1,3,4-oxadiazol-5-yl)methylthio]ethylamine.

When the above amine is reacted with an equimolar amount of 3,4-dimethoxy-1,2,5-thiadiazole 1,1-dioxide, and the resultant 3-{2-[(2-dimethylamino-1,3,4-oxadiazol-5-yl)methylthio]ethylamino}-4-methoxy-1,2,5-thiadiazole 1,1-dioxide is treated with an excess of methylamine, the title compound is thereby produced.

EXAMPLE 63

3-{2-[(3-{Dimethylaminomethyl}phenyl)methylthio]ethylamino}-4-amino-1,2,5-thiadiazole 1,1-dioxide When a methanolic suspension of 3,4-dimethoxy-1,2,5-thiadiazole 1,1-dioxide is successively treated with an equimolar amount of 2-[(3-{dimethylaminomethyl}phenyl)methylthio]ethylamine [prepared according to the procedure described in Belgian Pat. No. 867,106] and excess ammonia by the general procedure described in Example 35, the title compound is thereby produced.

EXAMPLE 64

3-{3-[3-(Dimethylaminomethyl)phenoxy]propylamino}-4-amino-1,2,5-thiadiazole 1,1-dioxide When a methanolic suspension of 3,4-dimethoxy-1,2,5-thiadiazole 1,1-dioxide is successively treated with an equimolar amount of 3-[3-(dimethylaminomethyl)phenoxy]propylamine [prepared according to the procedure described in Belgian Pat. No. 867,106] and excess ammonia by the general procedure described in Example 35, the title compound is thereby produced.

EXAMPLE 65

3-{2-[(5-Dimethylaminomethyl-2-thienyl)methylthio]ethylamino}-4-methylamino-1,2,5-thiadiazole 1,1-dioxide A solution of 2-[(5-dimethylaminomethyl-2-thienyl)methylthio]ethylamine (1.0 g; 4.34 mmoles) [prepared according to the procedure described in Belgian Pat. No. 867,105] in 25 ml of dry methanol was added dropwise over a period of 35 minutes to a stirred solution of 3,4-dimethoxy-1,2,5-thiadiazole 1,1-dioxide (0.77 g; 4.34 mmoles) in 150 ml of dry methanol that had been cooled to 0°–3° in an ice-water bath. After the addition was completed, anhydrous methylamine was bubbled into the solution for 10 minutes and stirring was continued for 15 minutes. The reaction mixture was evaporated under reduced pressure and the residue placed on 50 g of silica gel and chromatographed using a gradient elution of acetonitrile-methanol. The appropriate fractions were combined to give 1.0 g of product. Recrystallization from methanol yielded the title compound, mp 60.5°–66°.

EXAMPLE 66

3-{2-[(5-Dimethylaminomethyl-2-thienyl)methylthio]ethylamino}-4-ethylamino-1,2,5-thiadiazole 1-oxide When a solution of 3,4-dimethoxy-1,2,5-thiadiazole 1-oxide [prepared in Example 4, Step A] is successively reacted with an equimolar amount of 2-[(5-dimethylaminomethyl-2-thienyl)methylthio]ethylamine and excess ethylamine according to the procedure described in Example 18, the title compound is thereby produced.

EXAMPLE 67

3-{2-[(5-Dimethylaminomethyl-2-thienyl)methylthio]ethylamino}-4-{2-[(4-methyl-1,2,5-oxadiazol-3-yl)methylthio]ethylamino}-1,2,5-thiadiazole 1,1-dioxide When a suspension of 3,4-dimethoxy-1,2,5-thiadiazole 1,1-dioxide is reacted with an equimolar amount of 2-[(5-dimethylaminomethyl-2-thienyl)methylthio]ethylamine and the resultant 3-{2-[(5-dimethylaminomethyl-2-thienyl)methylthio]ethylamino}-4-methoxy-1,2,5-thiadiazole 1,1-dioxide is treated with 2-[(4-methyl-1,2,5-oxadiazol-3-yl)methylthio]ethylamine [prepared in Example 58, Step B], the title compound is thereby produced.

EXAMPLE 68

3-{4-[(2-Guanidino-4-oxazolyl]butylamino}-4-methylamino-1,2,5-thiadiazole 1,1-dioxide When a suspension of 3,4-dimethoxy-1,2,5-thiadiazole 1,1-dioxide is reacted with an equimolar amount of 4-[(2-guanidino-4-oxazolyl]butylamine [prepared according to the procedure described in Belgian Pat. No. 866,155] and the resultant 3-{4-[(2-guanidino-4-oxazolyl]butylamino}-4-methoxy-1,2,5-thiadiazole 1,1-dioxide is treated with excess methylamine, the title compound is thereby produced.

EXAMPLE 69

3-{2-[(2-(2-Amino-5-oxazolyl)ethylthio]ethylamino}-4-methylamino-1,2,5-thiadiazole 1,1-dioxide Reacting an equimolar amount of 3,4-dimethoxy-1,2,5-thiadiazole 1,1-dioxide and 2-[2-(2-amino-5-oxazolyl)ethylthio]ethylamine [prepared according to U.S. Pat. No. 3,950,353] and treatment of the resultant 3-{2-[2-(2-amino-5-oxazolyl)ethylthio]ethylamino}-4-methoxy-1,2,5-thiadiazole 1,1-dioxide with excess methylamine gives the title compound.

EXAMPLE 70

3-{2-[3-Isoxazolylmethylthio]ethylamino}-4-methylamino-1,2,5-thiadiazole 1,1-dioxide Reaction of a methanolic suspension of 3,4-dimethoxy-1,2,5-thiadiazole 1,1-dioxide with one equivalent of 2-[3-isoxazolylmethylthio]ethylamine [prepared according to the procedure described in U.S. Pat. No. 3,950,353] and treatment of the resultant 3-{2-[3-isoxazolylmethylthio]ethylamino}-4-methoxy-1,2,5-thiadiazole 1,1-dioxide with an excess of methylamine, produced the title compound.

EXAMPLE 71

The general procedure of Example 70 is repeated except that the 2-[3-isoxazolylmethylthio]ethylamine utilized therein is replaced by an equimolar amount of 2-[(5-methyl-3-isoxazolyl)methylthio]ethylamine, 2-[(3,5-dimethyl-4-isoxazolyl)methylthio]ethylamine and 2-[(2-(5-methyl-4-isoxazolyl)ethylthio]ethylamine, respectively, [each prepared by the general procedure described in U.S. Pat. No. 3,950,353] and there is thereby produced 3-{2-[(5-methyl-3-isoxazolyl)methylthio]ethylamino}-4-methylamino-1,2,5-thiadiazole 1,1-dioxide, 3-{2-[(3,5-dimethyl-4-isoxazolyl)methylthio}-4-methylamino-1,2,5-thiadiazole 1,1-dioxide and 3-{2-[2-(5-methyl-4-isoxazolyl)ethylthio]ethylamino}-4-methylamino-1,2,5-thiadiazole 1,1-dioxide, respectively.

EXAMPLE 72

3-{2-[(5-Dimethylaminomethyl-2-furyl)methylthio]ethylamino}-4-{2-[3-isoxazolylmethylthio]ethylamino}-1,2,5-thiadiazole 1,1-dioxide When a methanolic suspension of 3,4-dimethoxy-1,2,5-thiadiazole 1,1-dioxide is reacted with one equivalent of 2-[(5-dimethylaminomethyl-2-furyl)methylthio]ethylamine according to the procedure described in Example 17, Step A, and the resultant product is treated with one equivalent of 2-[(3-isoxazolylmethylthio]ethylamine, the title compound is thereby produced.

EXAMPLE 73

3-{2-[3-Isothiazolylmethylthio]ethylamino}-4-methylamino-1,2,5-thiadiazole 1,1-dioxide Reaction of a methanol suspension of 3,4-dimethoxy-1,2,5-thiadiazole 1,1-dioxide with one equivalent of 2-[3-isothiazolylmethylthio]ethylamine [prepared according to the procedure described in U.S. Pat. No. 3,950,353] and treatment of the resultant 3-{2-[3-isothiazolylmethylthio]ethylamino}-4-methoxy-1,2,5-thiadiazole 1,1-dioxide with an excess of methylamine, produces the title compound.

EXAMPLE 74

The general procedure of Example 73 is repeated except that the 2-[3-isothiazolylmethylthio]ethylamine utilized therein is replaced by an equimolar amount of 2-[(3-methyl-4-isothiazolyl)methylthio]ethylamine, 2-[(4-bromo-3-methyl-5-isothiazolyl)methylthio]ethylamine and 2-[(3-methyl-5-isothiazolyl)methylthio]ethylamine, respectively, [prepared by the general procedures described in U.S. Pat. No. 3,450,353 and *J. Chem. Soc.*, 2032 (1963)] and there is thereby produced 3-{2-[(3-methyl-4-isothiazolyl)methylthio]ethylamino}-4-methylamino-1,2,5-thiadiazole 1,1-dioxide, 3-{2-[(4-bromo-3-methyl-5-isothiazolyl)methylthio]ethylamino}-4-methylamino-1,2,5-thiadiazole 1,1-dioxide and 3-{2-[(3-methyl-5-isothiazolyl)methylthio]ethylamino}-4-methylamino-1,2,5-thiadiazole 1,1-dioxide, respectively.

EXAMPLE 75

3-{2-[(5-Dimethylaminomethyl-2-furyl)methylthio]ethylamino}-4-{2-[3-isothiazolylmethylthio]ethylamino}-1,2,5-thiadiazole 1,1-dioxide When a methanol suspension of 3,4-dimethoxy-1,2,5-thiadiazole 1,1-dioxide is reacted with one equivalent of 2-[(5-dimethylaminomethyl-2-furyl)methylthio]ethylamine according to the procedure described in Example 17, Step A, and the resultant 3-{2-[(5-dimethylaminomethyl-2-furyl)methylthio]ethylamino}-4-methoxy-1,2,5-thiadiazole 1,1-dioxide is treated with one equivalent of 2-[3-isothiazolylmethylthio]ethylamine, the title compound is produced.

EXAMPLE 76

3-{2-[(2-Amino-1,3,4-thiadiazol-5-yl)methylthio]ethylamino}-4-methylamino-1,2,5-thiadiazole 1,1-dioxide Reaction of 3,4-dimethoxy-1,2,5-thiadiazole 1,1-dioxide with one equivalent of 2-[(2-amino-1,3,4-thiadiazol-5-yl)methylthio]ethylamine [prepared according to the procedure described in U.S. Pat. No. 3,950,353] and treatment of the resultant 3-{2-[(2-amino-1,3,4-thiadiazol-5-yl)methylthio]ethylamino}-4-methoxy-1,2,5-thiadiazole 1,1-dioxide with methylamine, produced the title compound.

EXAMPLE 77

The general procedure of Example 76 is repeated except that the 2-[(2-amino-1,3,4-thiadiazol-5-yl)methylthio]ethylamine utilized therein is replaced by an equimolar amount of 3-[1,2,4-thiadiazol-3-ylthio]propylamine, 2-[(1,2,3-thiadiazol-4-yl)methylthio]ethylamine, 2-[(3-hydroxy-1,2,5-thiadiazol-4-yl)methylthio]ethylamine and 2-[(3-amino-1,2,5-thiadiazol-4-yl)methylthio]ethylamine, respectively, [prepared by the general procedures described in U.S. Pat. No. 3,950,353, *J. Am. Chem. Soc.*, 86, 2861 (1964) and *J. Org. Chem.*, 28, 1491 (1963)] and there is thereby produced 3-{3-[1,2,4-thiadiazol-3-ylthio]propylamino}-4-methylamino-1,2,5-thiadiazole 1,1-dioxide, 3-{2-[(1,2,3-thiadiazol-4-yl)methylthio]ethylamino}-4-methylamino-1,2,5-thiadiazole 1,1-dioxide, 3-{2-[(3-hydroxy-1,2,5-thiadiazol-4-yl)methylthio]ethylamino}-4-methylamino-1,2,5-thiadiazole 1,1-dioxide and 3-{2-[(3-amino-1,2,5-thiadiazol-4-yl)methylthio]ethylamino}-4-methylamino-1,2,5-thiadiazole 1,1-dioxide, respectively.

EXAMPLE 78

3-{2-[(5-Dimethylaminomethyl-2-furyl)methylthio]ethylamino}-4-{2-[(3-hydroxy-1,2,5-thiadiazol-4-yl)methylthio]ethylamino}-1,2,5-thiadiazole 1,1-dioxide When a methanol suspension of 3,4-dimethoxy-1,2,5-thiadiazole 1,1-dioxide is reacted with an equimolar amount of 2-[(5-dimethylaminomethyl-2-furyl)methylthio]ethylamine according to the procedure described in Example 17, Step A, and an equimolar amount of 2-[(3-hydroxy-1,2,5-thiadiazol-4-yl)methylthio]ethylamine, the title compound is thereby produced.

EXAMPLE 79

3-{2-[(2-Amino-1,2,4-thiazol-4-yl)methylthio]ethylamino}-4-methylamino-1,2,5-thiadiazole 1,1-dioxide Reaction of 3,4-dimethoxy-1,2,5-thiadiazole 1,1-dioxide with one equivalent of 2-[(2-amino-1,2,4-triazol-5-yl)methylthio]ethylamine [prepared according to general procedures described in U.S. Pat. No. 3,950,353] and an excess of methylamine by the general procedure described in Example 2, produces the title compound.

EXAMPLE 80

The general procedure of Example 79 is repeated except that the 2-[(2-amino-1,2,4-triazol-5-yl)methylthio]ethylamine utilized therein is replaced by an equimolar amount of
2-[(4-methyl-1,2,4-triazol-3-yl)methylthio]ethylamine,
2-[(5-methyl-1,2,3-triazol-4-yl)methylthio]ethylamine and
2-[1,2,4-triazol-3-yl)methylthio]ethylamine, respectively, [each prepared by the general procedures described in U.S. Pat. No. 3,950,353] and there is thereby produced
3-{2-[(4-methyl-1,2,4-triazol-3-yl)methylthio]ethylamino}-4-methylamino-1,2,5-thiadiazole 1,1-dioxide,
3-{2-[(5-methyl-1,2,3-triazol-4-yl)methylthio]ethylamino}-4-methylamino-1,2,5-thiadiazole 1,1-dioxide and
3-methylamino-4-{2-[1,2,4-triazol-3-ylmethylthio]ethylamino}-1,2,5-thiadiazole 1,1-dioxide, respectively.

EXAMPLE 81

3-{2-[(5-Dimethylaminomethyl-2-furyl)methylthio]ethylamino}-4-{2-[(5-methyl-1,2,3-triazol-4-yl)methylthio]ethylamino}-1,2,5-thiadiazole 1,1-dioxide When a methanolic suspension of 3,4-dimethoxy-1,2,5-thiadiazole 1,1-dioxide is reacted with an equimolar amount of 2-[(5-dimethylaminomethyl-2-furyl)methylthio]ethylamine according to the procedure described in Example 17, Step A, and an equimolar amount of 2-[(5-methyl-1,2,3-triazol-4-yl)methylthio]ethylamine, the title compound is produced.

EXAMPLE 82

3-{2-[(2-Dimethylaminomethyl-4-thiazolyl)methylthio]ethylamino}-4-dimethylamino-1,2,5-thiadiazole 1-oxide When a solution of 3,4-dimethoxy-1,2,5-thiadiazole 1-oxide [prepared in Example 4, Step A] is reacted with one equivalent of 2-[(2-dimethylaminomethyl-4-thiazolyl)methylthio]ethylamine [prepared in Example 33, Step E] and the resultant 3-{2-[(2-dimethylaminomethyl-4-thiazolyl)methylthio]ethylamino}-4-methoxy-1,2,5-thiadiazole 1-oxide is treated with an excess of dimethylamine according to the procedure described in Example 28, the title compound is thereby produced.

EXAMPLE 83

The general procedure of Example 82 is repeated, except that the dimethylamine utilized therein is replaced by
pyrrolidine,
piperidine,
morpholine,
thiomorpholine,
piperazine,
N-acetylpiperazine,
N-methylpiperazine,
hexamethyleneimine and
homopiperazine, respectively, and there is thereby produced
3-{2[(2-dimethylaminomethyl-4-thiazolyl)methylthio]ethylamino}-4-(1-pyrrolidinyl)-1,2,5-thiadiazole 1-oxide,
3-{2-[(2-dimethylaminomethyl-4-thiazolyl)methylthio]ethylamino}-4-(1-piperidinyl)-1,2,5-thiadiazole 1-oxide,
3-{2-[(2-dimethylaminomethyl-4-thiazolyl)methylthio]ethylamino}-4-(morpholinyl)-1,2,5-thiadiazole 1-oxide,
3-{2-[(2-dimethylaminomethyl-4-thiazolyl)methylthio]ethylamino}-4-(4-thiomorpholinyl)-1,2,5-thiadiazole 1-oxide,
3-{2-[(2-dimethylaminomethyl-4-thiazolyl)methylthio]ethylamino}-4-(1-piperazinyl)-1,2,5-thiadiazole 1-oxide,
3-{2-[(2-dimethylaminomethyl-4-thiazolyl)methylthio]ethylamino}-4-(4-acetyl-1-piperazinyl)-1,2,5-thiadiazole 1-oxide,
3-{2-[(2-dimethylaminomethyl-4-thiazolyl)methylthio]ethylamino}-4-(4-methyl-1-piperazinyl)-1,2,5-thiadiazole 1-oxide,
3-{2-[(2-dimethylaminomethyl-4-thiazolyl)methylthio]ethylamino}-4-(1-hexamethyleneimino)-1,2,5-thiadiazole 1-oxide and
3-{2-[(2-dimethylaminomethyl-4-thiazolyl)methylthio]ethylamino}-4-(1-homopiperazinyl)-1,2,5-thiadiazole 1-oxide, respectively.

EXAMPLE 84

3-{2-[(5-Dimethylaminomethyl-2-furyl)methythio]ethylamino}-4-ethylamino-1,2,5-thiadiazole 1-oxide A solution of 2-[(5-dimethylaminomethyl-2-furyl)methylthio]ethylamine (2.64 g; 12.3 mmoles) in 25 ml of dry methanol was added dropwise over a period of 30 minutes to a well stirred solution of 3,4-dimethoxy-1,2,5-thiadiazole 1-oxide (2.0 g; 12.3 mmoles) in 75 ml of dry methanol that had been cooled to 8° in an ice-water bath. After 15 minutes, 4.0 ml of ethylamine was added and the mixture stirred at ambient temperature for 1 hour. The reaction mixture was evaporated under reduced pressure and the residue placed on 55 g of silica gel and chromatographed using a gradient elution of methylene chloride-methanol. The appropriate fractions were combined, evaporated under reduced pressure and the residue treated with ether and decanted. The residue was treated with fresh ether to give 1.5 g of the title compound, mp 68°–74°.

Anal. Calcd. for $C_{14}H_{23}N_5O_2S_2$: C, 47.04; H, 6.48; N, 19.59; S, 17.94. Found (corr. for 1.24% $H_2O$): C, 46.54; H, 6.33; N, 19.37; S, 17.96.

EXAMPLE 85

3-{2-[(5-Dimethylaminomethyl-2-furyl)methylthio]ethylamino}-4-propylamino-1,2,5-thiadiazole 1,1-dioxide A solution of 2-[(5-dimethylaminomethyl-2-furyl)methylthio]ethylamine (2.41 g; 11.2 mmoles) in 25 ml of dry methanol was added dropwise over a period of 30 minutes to a well stirred suspension of 3,4-dimethoxy-1,2,5-thiadiazole 1,1-dioxide (2.0 g; 11.2 mmoles) in 200 ml of dry methanol that had been cooled to 2° in an ice-water bath. After 15 minutes, 4.0 ml of n-propylamine was added all at once and the mixture stirred at ambient temperature for 30 minutes. The reaction mixture was evaporated under reduced pressure and the residue placed on 55 g of silica gel and chromatographed using a gradient elution of methylene chloride-methanol. The appropriate fractions were combined, evaporated under reduced pressure and the syrup crystallized with ether to give 3.7 g of the title compound, mp 164°–166°; the NMR spectrum (100 MHz) in $d_6$ dimethyl sulfoxide showed the presence of approximately 0.9 moles of methanol.

Anal. Calcd for $C_{15}H_{25}N_5O_3S_2 \cdot 0.9CH_4O$: C, 45.86; H, 6.92; N, 16.82; S, 15.40. Found: C, 45.60; H, 6.93; N, 17.03; S, 15.47.

EXAMPLE 86

3-Amino-4-{2-[(5-dimethylaminomethyl-2-furyl)methylthio]ethylamino}-1,2,5-thiadiazole 1-oxide A solution of 2-[(5-dimethylaminomethyl-2-furyl)methylthio]ethylamine (3.3 g; 15.4 mmoles) in 25 ml. of methanol was added dropwise over a period of 30 minutes to a well stirred solution of 3,4-dimethoxy-1,2,5-thiadiazole 1-oxide (2.5 g; 15.4 mmoles) in 75 ml of methanol that had been cooled to 8° in an ice-water bath. After 1.5 hours, anhydrous ammonia was bubbled into the solution for 8 minutes and the mixture stirred at ambient temperature for 30 minutes. The reaction mixture was evaporated under reduced pressure and the residue placed on 60 g of silica gel and chromatographed using a gradient elution of methylene chloride-methanol. The appropriate fractions were combined and evaporated, and the product was crystallized from acetonitrile. Recrystallization from isopropyl alcohol yielded 2.59 g of the title compound, mp 139°–142°.

Anal. Calcd for $C_{12}H_{19}N_5O_2S_2$: C, 43.75; H, 5.81; N, 21.26; S, 19.46. Found: C, 43.71; H, 6.05; N, 21.32; S, 19.51.

EXAMPLE 87

3-Amino-4-{2-[(5-dimethylaminomethyl-2-furyl)methylthio]ethylamino}-1,2,5-thiadiazole 1,1-dioxide A solution of 2-[(5-dimethylaminomethyl-2-furyl)methylthio]ethylamine (2.5 g; 11.7 mmoles) in 50 ml. of dry methanol was added dropwise over 45 minutes to a well stirred suspension of 3,4-dimethoxy-1,2,5-thiadiazole 1,1-dioxide (2.08 g; 11.8 mmoles) in 200 ml. of dry methanol that had been cooled to 5° in an ice-water bath. After 30 minutes, anhydrous ammonia was bubbled into the solution for 10 minutes and the mixture stirred at ambient temperature for 8 hours. The reaction mixture was evaporated under reduced pressure and the residue placed on 200 g of silica gel and chromatographed using a gradient elution of methylene chloride-methanol. The appropriate fractions were combined and evaporated to give 3.6 g of product. Recrystallization from methanol-ether yielded the title compound, mp 156°–158°.

Anal. Calcd for $C_{12}H_{19}N_5O_3S_2$: C, 41.72; H, 5.54; N, 20.28; S, 18.56. Found: C, 41.50; H, 5.52; N, 20.33; S, 18.74.

EXAMPLE 88

3-Amino-4-{2-[(2-guanidinothiazol-4-yl)methylthio]ethylamino}-1,2,5-thiadiazole 1-oxide A solution of 2-[(guanidinothiazol-4-yl)methylthio]ethylamine (from the dihydrochloride, 6.08 g; 20.0 mmoles) in 50 ml of methanol was added dropwise, over 45 minutes, to a cold (5°) well stirred solution of 3,4-dimethoxy-1,2,5-thiadiazole 1-oxide (3.24 g; 20.0 mmoles) in 150 ml of methanol. After stirring at 5°–10° for 1.5 hours, anhydrous ammonia was bubbled into the solution for 10 minutes and stirring was continued at ambient temperature for 18 hours. The reaction mixture was evaporated under reduced pressure and the residue placed on 65 g of silica gel and chromatographed using a gradient elution of methylene chloride-methanol. The appropriate fractions were combined and evaporated to give 4.16 g of product from methanol. Recrystallization from methanol yielded the title compound, mp 167°–170° (dec).

Anal. Calcd for $C_9H_{14}N_8OS_3$: C, 31.20; H, 4.07; N, 32.35; S, 27.76. Found (corr. for 0.48% $H_2O$): C, 30.39; H, 3.97; N, 32.25; S, 27.91.

Recrystallization of the crude product from 95% ethanol yielded the title compound as a monohydrate, mp 136°–138° (dec).

Anal. Calcd for $C_9H_{14}N_8OS_3 \cdot H_2O$: C, 29.66; H, 4.42; N, 30.75; S, 26.39. Found: C, 29.92; H, 4.42; N, 30.84; S, 26.58.

A sample of the product as the free base was suspended in 95% ethanol, treated with one equivalent of aqueous 6.0 N hydrochloric acid and filtered to yield the hydrochloride salt, mp 200°–201° C. (dec.)

Anal. Calcd for $C_9H_{15}ClN_8OS_3$: S, 28.23; H, 3.95; N, 29.26; Cl, 9.26 Found (corr. for 1.02% $H_2O$): C, 28.26; H, 3.83; N, 29.41; Cl, 9.53

EXAMPLE 89

3-Benzylamino-4-{2-[(5-dimethylaminomethyl-2-furyl)methylthio]ethylamino}-1,2,5-thiadiazole 1,1-dioxide A solution of 2-[(5-dimethylaminomethyl-2-furyl)methylthio]ethylamine (2.4 g; 11.2 mmoles) in 30 ml of dry methanol was added dropwise over a period of 35 minutes to a stirred solution of 3,4-dimethoxy-1,2,5-thiadiazole 1,1-dioxide (2.0 g; 11.2 mmoles) in 200 ml of dry methanol that had been cooled to 1°–3° in an ice water bath. After 15 minutes at 1°–3°, benzylamine (1.8 g, 1.83 ml; 16.8 mmoles) was added and the solution stirred at ambient temperature for 1 hour. The reaction mixture was evaporated under reduced pressure and the residue placed on 50 g of silica gel and chromatographed using a gradient elution of methylene chloride-methanol. The appropriate fractions were combined to give 4.1 g of product. Recrystallization from aqueous methanol and then methanol yielded the title compound, mp 152° (dec); the NMR spectrum (100 MHz) in $d_6$ dimethyl sulfoxide showed the presence of approximately 1.0 mole of methanol.

Anal. Calcd for $C_{19}H_{25}N_5O_3S_2 \cdot CH_4O$: C, 51.37; H, 6.25; N, 14.98. Found: C, 51.51; H, 6.05; N, 14.78.

EXAMPLE 90

3-{2-[(3-{Dimethylaminomethyl}phenyl)methylthio]ethylamino}-4-methylamino-1,2,5-thiadiazole, 1,1-dioxide A solution of 2-[(3-{dimethylaminomethyl}phenyl)methylthio]ethylamine (2.51 g; 11.2 mmoles) [prepared according to the procedure described in Belgian Pat. No. 867,106] in 25 ml of dry methanol was added dropwise over 30 minutes to a well stirred suspension of 3,4-dimethoxy-1,2,5-thiadiazole 1,1-dioxide (2.0 g; 11.2 mmoles) in 200 ml of dry methanol that had been cooled to 2° in an ice-water bath. After 15 minutes at 2°–5°, anhydrous methylamine was bubbled into the solution for 10 minutes and the solution was then stirred at ambient temperature for 30 minutes. The reaction mixture was evaporated under reduced pressure and the residue placed on 60 g of silica gel and chromatographed using a gradient elution of methylene chloride-methanol. The appropriate fractions were combined to give 2.96 g of product. Recrystallization from acetonitrile and then from methanol yielded and title compound, mp 152°–158°; the NMR spectrum (100 mHz) in $d_6$ dimethyl sulfoxide showed the presence of approximately 0.6 mole of methanol.

Anal. Calcd for $C_{15}H_{23}N_5O_2S_2 \cdot 0.6CH_4O$: C, 48.20; H, 6.59; N, 18.02; S, 16.49. Found: C, 47.99; H, 6.78; N, 17.81; S, 16.09.

EXAMPLE 91

3-Amino-4-{2-[(3-{dimethylaminomethyl}phenyl)methylthio]ethylamino}-1,2,5-thiadiazole 1-oxide A solution of 2-[(3-{dimethylaminomethyl}phenyl)methylthio]ethylamine (2.77 g; 12.3 mmoles) in 25 ml of dry methanol was added dropwise over 45 minutes to a well stirred solution of 3,4-dimethoxy-1,2,5-thiadiazole 1-oxide (2.0 g; 12.3 mmoles) in 100 ml of dry methanol that had been cooled to 5° in an ice-water bath. When the addition was completed, the solution was stirred at ambient temperature for 1.5 hours and then cooled to 5° and anhydrous ammonia was bubbled into the solution for 8 minutes. After stirring 16 hours at ambient temperature, the reaction mixture was evaporated under reduced pressure and the residue placed on 55 g of silica gel and chromatographed using a gradient elution of methylene chloride-methanol. The appropriate fractions were combined to give 3.0 g of product from acetonitrile. Recrystallization from acetone yielded the title compound, mp 122°–125°.

Anal. Calcd for $C_{14}H_{21}N_5OS_2$: C, 49.53; H, 6.23; N, 20.63; S, 18.89. Found: C, 49.18; H, 6.08; N, 20.93; S, 19.25.

EXAMPLE 92

3-{2-[(5-Dimethylaminomethyl-2-thienyl)methylthio]ethylamino}-4-methylamino-1,2,5-thiadiazole 1-oxide A solution of 2-[(5-dimethylaminomethyl-2-thienyl)methylthio]ethylamine (1.5 g; 6.5 mmoles) in 25 ml of dry methanol was added dropwise over a period of 45 minutes to a stirred solution of 3,4-dimethoxy-1,2,5-thiadiazole 1-oxide (1.06 g; 6.5 mmoles) in 150 ml of dry methanol that had been cooled to 3° in an ice-water bath. After 15 minutes at 3°, anhydrous methylamine was bubbled into the solution for 5 minutes and the solution was stirred for 15 minutes. The reaction mixture, after standing overnight at ambient temperature, was evaporated under reduced pressure and the residue placed on 75 g of silica gel and chromatographed using a gradient elution of acetonitrile-methanol. The appropriate fractions were combined to give crystalline product from acetonitrile. Recrystallization from acetonitrile yielded the title compound, mp 98.5°–102°.

Anal. Calcd for $C_{13}H_{21}N_5OS_3$: C, 43.42; H, 5.89; N, 19.48; S, 26.76. Found: C, 43.70; H, 5.58; N, 19.71; S, 26.79.

EXAMPLE 93

3-Amino-4-{4-(5-dimethylaminomethyl-2-furyl)-butylamino}-1,2,5-thiadiazole 1,1-dioxide A solution of 4-(5-dimethylaminomethyl-2-furyl)-butylamine (1.61 g; 8.2 mmoles) in 25 ml of dry methanol was added dropwise over a period of 35 minutes to a well stirred suspension of 3,4-dimethoxy-1,2,5-thiadiazole 1,1-dioxide (1.46 g; 8.2 mmoles) in 150 ml of dry methanol that had been cooled to 0°–3° in an ice-water bath. After 15 minutes, anhydrous ammonia was bubbled into the solution for 5 minutes and the solution was stirred for 30 minutes. The reaction mixture was evaporated under reduced pressure and the residue placed on 60 g of silica gel and chromatographed using a gradient elution of acetonitrile-methanol. The appropriate fractions were combined and evaporated to give 1.68 g of product. Crystallization from acetonitrile yielded the title compound, mp 154°–156° (dec).

Anal. Calcd for $C_{13}H_{21}N_5O_3S$: C, 47.69; H, 6.47; N, 21.39; S, 9.80. Found: C, 47.73; H, 6.28; N, 21.43; S, 9.84.

EXAMPLE 94

3-Amino-4-{2-[(2-dimethylaminomethyl-4-thiazolyl)-methylthio]ethylamino}-1,2,5-thiadiazole 1,1-dioxide A solution of 2-[(2-dimethylaminomethyl-4-thiazolyl)methylthio]ethylamine (0.9 g; 3.89 mmoles) in 20 ml of dry methanol was added dropwise over 40 minutes to a well stirred suspension of 3,4-dimethoxy-1,2,5-thiadiazole 1,1-dioxide (0.69 g; 3.89 mmoles) in 70 ml of methanol that had been cooled to 8°, anhydrous ammonia was bubbled into the solution for 8 minutes and then the solution was allowed to stir at ambient temperature for 18 hours. The reaction mixture was evaporated under reduced pressure and the residue placed on 150 g of silica gel and chromatographed using a gradient elution of acetonitrile-methanol. The appropriate fractions were combined and evaporated to give 0.66 g of the product. The foam was dissolved in 2-propanol and evaporated to dryness to give the title compound, mp 60°–65°; the NMR spectrum (100 MHz) in $d_6$ dimethyl sulfoxide showed the presence of approximately 0.15 mole of 2-propanol.

Anal. Calcd for $C_{11}H_{18}N_6S_3O_2 \cdot 0.15C_3H_8O$: C, 37.02; H, 5.21; N, 22.62; S, 25.89. Found (corr. for 2.79% $H_2O$): C, 36.75; H, 5.13; N, 21.75; S, 25.03.

EXAMPLE 95

3-{2-[(2-Guanidinothiazol-5-yl)methylthio]ethylamino}-4-methylamino-1,2,5-thiadiazole 1,1-dioxide (A) Ethyl 2-Guanidino-5-thiazolecarboxylate Hydrochloride A solution of amidinothiourea (117 g; 0.99 mole) and ethyl chloro-α-formylacetate (150 g; 1.0 mole) in 3.5 liters of absolute ethanol was stirred at ambient temperature for 18 hours and then heated at reflux temperature for 1 hour. At this time additional ethyl chloro-α-formylacetate (20.0 g; 0.13 mole) was added and 1 hour later another 20.0 g of ethyl chloro-α-formylacetate was added. After 2 hours of additional heating at reflux temperature, the reaction mixture was evaporated under reduced pressure and the residue triturated with 1.5 liters of acetone and filtered to give 103 g of product. Recrystallization from 2-propanol yielded the title compound, mp 204°–206°.

Anal. Calcd for $C_7H_{11}ClN_4O_2S$: C, 33.53; H, 4.43; N, 22.35; Cl, 14.14; S, 12.79. Found: C, 33.38; H, 4.40; N, 22.54; Cl, 13.97; S, 12.92.

(B) 2-Guanidino-5-hydroxymethylthiazole

Ethyl 2-guanidino-5-thiazolecarboxylate hydrochloride (1.0 g; 3.99 mmoles) [prepared in Step A] was added to a cooled (ice-water bath) suspension of lithium aluminum hydride (0.46 g; 12.1 mmoles) in 25 ml of tetrahydrofuran. The reaction mixture was then heated at reflux temperature for 2 hours, cooled, decomposed with 0.46 ml $H_2O$, 0.46 ml of 15% NaOH and 1.38 ml $H_2O$ and filtered. The filtrate was dried and evaporated under reduced pressure to give 0.61 g of product. Recrystallization from acetonitrile yielded the title compound, mp 168°–170°.

Anal. Calcd for $C_5H_8N_4OS$: C, 34.87; H, 4.68; N, 32.54; S, 18.62. Found: C, 34.55; H, 4.52; N, 32.63; S, 18.54.

(C) 2-[(2-Guanidinothiazol-5-yl)methylthio]ethylamine

Cysteamine hydrochloride (10.6 g; 9.3 mmoles) and 2-guanidino-5-hydroxymethylthiazole (16.0 g; 9.3 mmoles) [prepared in Step B] were dissolved in 80 ml of concentrated hydrochloric acid and the solution stirred at ambient temperature for 1 hour and then heated at reflux temperature for 3 hours. The reaction mixture was cooled, made basic (pH 11) with 40% aqueous NaOH and filtered to give 15 g of product. Recrystallization from acetonitrile yielded the title compound, mp 150°–153°.

Anal. Calcd for $C_7H_{13}N_5S_2$: C, 36.34; H, 5.66; N, 30.27; S, 27.72. Found: C, 36.29; H, 5.70; N, 30.40; S, 27.64.

(D) 3-{2-[(2-Guanidinothiazol-5-yl)methylthio]ethylamino}-4-methylamino-1,2,5-thiadiazole 1,1-dioxide A solution of 2-[(2-guanidinothiazol-5-yl)methylthio]ethylamine (2.0 g; 8.64 mmoles) [prepared in Step C] in 60 ml of methanol was added dropwise over 40 minutes to a well stirred suspension of 3,4-dimethoxy-1,2,5-thiadiazole 1,1-dioxide (1.54 g; 8.64 mmoles) in 160 ml of methanol that had been cooled to 8° in an ice-water bath. While maintaining the temperature at 8°, anhydrous methylamine was bubbled into the solution for 8 minutes. After stirring at ambient temperature for 18 hours, the reaction mixture was evaporated under reduced pressure and the residue placed on 175 g of silica gel and chromatographed using a gradient elution of acetonitrile-methanol. The appropriate fractions were combined to give 1.3 g of product. Recrystallization from methanol yielded the title compound, mp 225°–226° (dec.).

Anal. Calcd for $C_{10}H_{16}N_8O_2S_3$: C, 31.90; H, 4.28; N, 29.76; S, 25.55. Found: C, 32.07; H, 4.14; N, 29.91; S, 25.60.

EXAMPLE 96

3-Amino-4-{2-[(2-guanidinothiazol-5-yl)methylthio]ethylamino}-1,2,5-thiadiazole 1-oxide A solution of 2-[(2-guanidinothiazol-5-yl)methylthio]ethylamine (3.0 g; 13.0 mmoles) [prepared in Example 95, Step C] in 70 ml of methanol was added dropwise over 40 minutes to a well stirred solution of 3,4-dimethoxy-1,2,5-thiadiazole 1-oxide (2.1 g; 13.0 mmoles) in 200 ml of methanol that had been cooled to 8°, and anhydrous ammonia was then bubbled into the solution for 8 minutes. After stirring at ambient temperature for 18 hours, the reaction mixture was evaporated under reduced pressure and the residue placed on 225 g of silica gel and chromatographed using a gradient elution of acetonitrile-methanol. The appropriate fractions were combined to give 3.6 g of the title compound, mp 85°–132°; the NMR spectrum (100 MHz) in $d_6$ dimethyl sulfoxide showed the presence of approximately 0.3 mole of acetonitrile.

Anal. Calcd for $C_9H_{14}N_8OS_3.0.3C_2H_3N$: C, 32.24; H, 4.22; N, 32.41; S, 26.71. Found (corr. for 1.84% $H_2O$): C, 32.63; H, 4.33; N, 32.55; S, 26.62.

EXAMPLE 97

3-Cyclopropylamino-4-{2-[(5-dimethylaminomethyl-2-furyl)methylthio]ethylamino}-1,2,5-thiadiazole 1,1-dioxide The general procedure of Example 13 was repeated, except that the 2-propynylamine utilized therein was replaced by an equimolar amount of cyclopropylamine, and the product was crystallized from methanol. Recrystallization from isopropyl alcohol yielded 3.5 g of the title compound, mp 194°–195° (dec.); the NMR spectrum (100 MHz) in $d_6$ dimethyl sulfoxide and showed the presence of approximately 1.0 mole of isopropyl alcohol.

Anal. Calcd for $C_{15}H_{23}N_5O_3S_2.C_3H_8O$: C, 48.52; H, 7.01; N, 15.72. Found: C, 48.36; H, 6.95; N, 14.87.

EXAMPLE 98

3-Cyclopropylmethylamino-4-{2-[(5-dimethylaminomethyl-2-furyl)methylthio]ethylamino}-1,2,5-thiadiazole 1,1-dioxide The general procedure of Example 13 was repeated, except that the 2-propynylamine utilized therein was replaced by an equimolar amount of cyclopropylmethyamine, and the product was crystallized from methanol. Recrystallization from methanol yielded 1.6 g of the title compound, mp 86°–89° (dec.); the NMR spectrum (100 MHz) in $d_6$ dimethyl sulfoxide showed the presence of approximately 1.25 moles of methanol.

Anal. Calcd for $C_{16}H_{25}N_5O_3S_2.1.25 CH_4O$: C, 47.13, H, 6.88; N, 15.93. Found (corr. for 0.68% $H_2O$): C, 47.40; H, 6.49; N, 15.77.

EXAMPLE 99

3-{2-[(5-Dimethylaminomethyl-2-furyl)methylthio]ethylamino}-4-morpholino-1,2,5-thiadiazole 1,1-dioxide The general procedure of Example 28 was repeated, except that the dimethylamine utilized therein was replaced by an equimolar amount of morpholine. After column chromatography, the product was crystallized from isopropyl alcohol. The mixture was diluted with Skellysolve B and filtered to yield the title compound, mp 122°–127°.

Anal. Calcd for $C_{16}H_{25}N_5O_4S_2$: C, 46.24; H, 6.06; N, 16.86. Found (corr. for 0.61% $H_2O$): C, 45.82; H, 6.06; N, 16.62.

EXAMPLE 100

3-{2-[(5-Dimethylaminomethyl-2-furyl)methylthio]ethylamino}-4-(2-methylethylamino)-1,2,5-thiadiazole 1,1-dioxide The general procedure of Example 13 was repeated, except that the 2-propynylamine utilized therein was replaced by an equimolar amount of 2-methoxyethylamine. After column chromatography, the residue was treated with isopropyl alcohol, evaporated to near dryness and cooled to give 3.79 g of product. Recrystallization from isopropyl alcohol yielded the title compound, mp 56°–58°; the NMR spectrum (100 MHz) in $d_6$ dimethyl sulfoxide showed the presence of approximately 0.6 moles of isopropyl alcohol.

Anal. Calcd for $C_{15}H_{25}N_5O_4S_2.0.6 C_3H_8O$: C, 45.90; H, 6.83; N, 15.93. Found (corr. for 0.74% $H_2O$): C, 45.50; H, 6.72; N, 15.63.

EXAMPLE 101

3-{2-[(5-Dimethylaminomethyl-2-furyl)methylthio]-ethylamino}-4-pyrrolidino-1,2,5-thiadiazole 1,1-dioxide The general procedure of Example 28 was repeated, except that the dimethylamine utilized therein was replaced by an equimolar amount of pyrrolidone. The crude reaction mixture was evaporated under reduced pressure, treated with isopropyl alcohol and filtered to yield 3.9 g of the title compound, mp 151°–152°.

Anal. Calcd for $C_{16}H_{25}N_5O_3S_2$: C, 48.09; H, 6.31; N, 17.53. Found: C, 48.00; H, 6.10; N, 17.71.

EXAMPLE 102

3-{2-[(5-Dimethylaminomethyl-2-furyl)methylthio]-ethylamino}-4-piperidino-1,2,5-thiadiazole 1,1-dioxide The general procedure of Example 28 was repeated, except that the dimethylamine utilized therein was replaced by an equimolar amount of piperidine. Chromatography yielded 3.8 g of product. Recrystallization from hot aqueous ethanol yielded the title compound, mp 160°–108°.

Anal. Calcd. for $C_{18}H_{27}N_5O_3S_2$: C, 49.37; H, 6.58; N, 16.94. Found (corr. for 0.2% $H_2O$): C, 49.17; H, 6.52; N, 17.14.

EXAMPLE 103

3-Butylamino-4-{2-[(5-dimethylaminomethyl-2-furyl)-methylthio]-ethylamino}-1,2,5-thiadiazole 1,1-dioxide The general procedure of Example 13 was repeated, except that the 2-propynylamine utilized therein was replaced by an equimolar amount of butylamine. The crude product was chromatographed three times and dried with heating under high vacuum for 3.5 hours to yield 1.81 g of the title compound as a somewhat gummy foam.

Anal. Calcd for $C_{16}H_{27}N_5O_3S_2$: C, 47.86; H, 6.78; N, 17.44. Found (corr. for 1.34% $H_2O$): C, 47.60; H, 6.81; N, 17.81.

EXAMPLE 104

3-{2-[(5-Dimethylaminomethyl-2-furyl)methylthio]-ethylamino}-4-[(2-pyridyl)methylamino]-1,2,5-thiadiazole 1,1-dioxide The general procedure of Example 13 was repeated, except that the 2-propynylamine utilized therein was replaced by an equimolar amount of 2-aminomethylpyridine. The appropriate fractions from column chromatography were combined to give 3.9 g of product. Two recrystallizations from isopropyl alcohol yielded the title compound, mp 43°–45°. A sample was recrystallized from absolute ethanol and the solid was heated under vacuum at 60° for 6 hours to give a melt. The melt was dissolved in hot isopropyl alcohol, collected by filtration at ambient temperature and dried under high vacuum to yield the title compound, mp 45°–47°; the NMR spectrum (100 MHz) in $d_6$ dimethyl sulfoxide showed the presence of approximately 1.25 moles of isopropyl alcohol.

Anal. Calcd for $C_{18}H_{24}N_6O_3S_2 \cdot 1.25\ C_3H_8O$: C, 51.05; H, 6.70; N, 16.42. Found (corr. for 0.58% $H_2O$): C, 51.08; H, 6.32; N, 16.03.

EXAMPLE 105

3-{2-[(5-Dimethylaminomethyl-2-furyl)methylthio]-ethylamino}-4-hydroxylamino-1,2,5-thiadiazole 1,1-dioxide The general procedure of Example 13 was repeated, except that the 2-propynylamine utilized therein was replaced by an equimolar amount of hydroxylamine. The crude reaction mixture which had deposited the product as an oil was heated to reflux temperature until all the product crystallized, then filtered and dried to give 2.59 g of the title compound, mp 203°–205°.

Anal. Calcd for $C_{12}H_{19}N_5O_4S_2$: C, 39.87; H, 5.30; N, 19.38; S, 17.74. Found (corr. for 1.18% $H_2O$): C, 39.53; H, 5.04; N, 19.61; S, 17.62.

EXAMPLE 106

3-{2-[(5-Dimethylaminomethyl-2-furyl)methylthio]-ethylamino}-4-dodecylamino-1,2,5-thiadiazole 1,1-dioxide A solution of 2-[(5-dimethylaminomethyl-2-furyl)methylthio]ethylamine (2.41 g; 11.2 mmoles) in 25 ml of methanol was added dropwise to a well stirred cold suspension of 3,4-dimethoxy-1,2,5-thiadiazole 1,1-dioxide (2.0 g; 11.2 mmoles) in 200 ml of methanol. After stirring at 2°–5° for 15 minutes, a solution of dodecylamine (4.15 g; 22.4 mmoles) in 25 ml of methanol was added all at once, and stirring was continued at ambient temperature for 18 hours. The reaction mixture was filtered and evaporated under reduced pressure, and the residue placed on 60 g of silica gel and chromatographed using a gradient elution of methylene chloride-methanol. The appropriate fractions were combined, evaporated and the residue was rechromatographed on 60 g of silica gel using a gradient elution of acetonitrile-methanol. The appropriate fractions from the second chromatography were combined, concentrated under reduced pressure and the crystallized product was collected by filtration and dried to give 2.13 g of the title compound, mp 136°–139°.

Anal. Calcd for $C_{24}H_{45}N_5O_3S_2$: C, 55.89; H, 8.79; N, 13.58; S, 12.43. Found: C, 56.16; H, 8.57; N, 13.38; S, 12.61.

EXAMPLE 107

3-{2-[(5-Dimethylaminomethyl-2-furyl)methylthio]-ethylamino}-4-methoxyamino-1,2,5-thiadiazole 1,1-dioxide The general procedure of Example 13 was repeated, except that the 2-propynylamine utilized therein was replaced by an equimolar amount of methoxyamine. The reaction mixture was stirred at ambient temperature overnight, during which a crystalline precipitate formed. The solution was cooled and filtered, and the recovered solid was dried to yield 3.8 g of the title compound, mp 224°–226° (dec.).

Anal. Calcd for $C_{13}H_{21}N_5O_4S_2$: C, 41.59; H, 5.64; N, 18.65; S, 17.08. Found (corr. for 0.79% $H_2O$): C, 41.25; H, 5.54; N, 18.50; S, 17.16.

EXAMPLE 108

3-{2-[(5-Dimethylaminomethyl-2-thienyl)methylthio]-ethylamino}-4-propylamino-1,2,5-thiadiazole 1,1-dioxide The general procedure of Example 65 was repeated, except that the methylamine utilized therein was replaced by an equimolar amount of propylamine. Chromatography gave 3.5 g of crystalline product. Recrystallization from acetonitrile yielded the title compound, mp 194°–196° (dec.).

Anal. Calcd for $C_{15}H_{25}N_5O_2S_3$: C, 44.64; H, 6.24; N, 17.35; S, 23.84. Found: C, 44.66; H, 6.02; N, 17.88; S, 23.87.

EXAMPLE 109

3-Amino-4-{2-[(5-dimethylaminomethyl-2-thienyl)methylthio]-ethylamino}-1,2,5-thiadiazole 1-oxide A solution of 2-[(5-dimethylaminomethyl-2-thienyl)methylthio]ethylamine (2.84 g; 12.3 mmoles) in 25 ml of methanol was added dropwise over a period of 35 minutes to a stirred solution of 3,4-dimethoxy-1,2,5-thiadiazole 1-oxide (2.0 g; 12.3 mmoles) in 200 ml of methanol that had been cooled to 3° in an ice-water bath. After stirring for 15 minutes, anhydrous ammonia was bubbled into the solution for 5 minutes. The reaction mixture was evaporated under reduced pressure, and the residue placed on 60 g of silica gel and chromatographed using a gradient elution of methylene chloride-methanol. The appropriate fractions were combined to give 1.73 g of product. Recrystallization from acetonitrile yielded the title compound, mp 149°–152° (dec.).

EXAMPLE 110

3-{2-[(5-Dimethylaminomethyl-2-thienyl)methylthio]ethylamino}-4-[(3-pyridyl)methylamino]-1,2,5-thiadiazole 1,1-dioxide The general procedure of Example 65 was repeated, except that the methylamine utilized therein was replaced by an equimolar amount of 3-aminomethylpyridine. The appropriate fractions from column chromatography gave 3.10 g of the title compound as an oil. The product was dissolved in excess 5% HCl, evaporated and then triturated with isopropyl alcohol to give a solid product. Recrystallization from 95% aqueous ethanol yielded the title compound as a dihydrochloride salt, mp 143°–146.5°.

Anal. Calcd for $C_{18}H_{26}Cl_2N_6O_2S_3$: C, 41.13; H, 4.99; N, 15.99; S, 18.30. Found (corr. for 2.04% $H_2O$): C, 41.25; H, 4.90, N, 16.18; S, 18.52.

EXAMPLE 111

3-Amino-4-{2-[(5-dimethylaminomethyl-2-thienyl)methylthio]ethylamino}-1,2,5-thiadiazole 1,1-dioxide A solution of 2-[(5-dimethylaminomethyl-2-thienyl)methylthio]ethylamine (2.0 g; 8.68 mmoles) in 25 ml of methanol was added dropwise over a period of 35 minutes to a stirred solution of 3,4-dimethoxy-1,2,5-thiadiazole 1,1-dioxide (1.55 g; 8.68 mmoles) in 200 ml of methanol that had been cooled to 3° in an ice-water bath. After stirring for 15 minutes, anhydrous ammonia was bubbled through the solution for 10 minutes. The reaction mixture was evaporated under reduced pressure to give 3.3 g of the title compound.

The NMR spectrum (100 MHz) in $d_6$ dimethyl sulfoxide gave the following resonances δ: 6.88 (d, 1H); 6.78 (d, 1H); 4.03 (s, 2H); 3.61 (s, 2H); 3.54 (t, 2H); 2.74 (t, 2H); 2.22 (s, 6H); it also showed the presence of approximately 2/3 mole of methanol.

EXAMPLE 112

3-Benzylamino-4-{2-[(5-dimethylaminomethyl-2-thienyl)methylthio]ethylamino}-1,2,5-thiadiazole 1,1-dioxide The general procedure of Example 65 was repeated, except that the methylamine utilized therein was replaced by an equimolar amount of benzylamine. The reaction mixture was evaporated under reduced pressure to give product. Recrystallization from methanol with charcoal treatment yielded 2.63 g of the title compound, mp 203°–205.5° (dec.).

Anal. Calcd for $C_{19}H_{25}N_5O_2S_3$: C, 50.53; H, 5.58; N, 15.51; S, 21.30. Found: C, 50.79; H, 5.34; N, 15.78; S, 20.94.

EXAMPLE 113

3-[3-(3-Dimethylaminomethylphenoxy)propylamino]-4-methylamino-1,2,5-thiadiazole 1,1-dioxide A solution of 3-[3-(dimethylaminomethyl)phenoxy]propylamine (2.73 g; 14.0 mmoles) [prepared according to the procedure described in Belgian Patent 867,106] in 50 ml of methanol was added dropwise over a period of 60 minutes to a stirred suspension of 3,4-dimethoxy-1,2,5-thiadiazole 1,1-dioxide (2.5 g; 14.0 mmoles) in 250 ml of methanol that had been cooled to 4° in an ice-water bath. After stirring for 20 minutes, anhydrous methylamine was bubbled into the solution for 10 minutes. The reaction mixture was evaporated under reduced pressure and the residue placed on 75 g of silica gel and chromatographed using a gradient elution of methylene chloride-methanol. The appropriate fractions were combined and evaporated, and then dissolved in n-propanol and treated with one equivalent of HCl to give the product as a hydrochloride salt. Recrystallization from aqueous ethanol yielded the title compound as a hydrochloride salt, mp 140°–145°.

Anal. Calcd for $C_{15}H_{24}ClN_5O_3S$: C, 46.20; H, 6.20; N, 17.96; S, 8.22; Cl, 9.09. Found (corr. for 3.79% $H_2O$): C, 46.21; H, 6.06, N, 18.24; S, 8.38; Cl, 9.05.

EXAMPLE 114

3-{2-[(2-Dimethylaminomethylthiazol-5-yl)methylthio]ethylamino}-4-methylamino-1,2,5-thiadiazole 1,1-dioxide A. 5-Carbethoxy-2-(N-carbophenoxy-N-methylamino)methylthiazole (N-Carbophenoxy-N-methylamino)thioacetamide (46.7 g; 0.21 moles) was combined with ethyl α-formylchloroacetate (30.0 g; 0.20 moles) in 270 ml of 1,2-dichloroethane and heated to reflux temperature for 2 hours. An additional amount of ethyl α-formylchloroacetate (3.0 g; 0.02 moles) was added and heating was continued for 1.5 hours. The reaction mixture was extracted with two 300 ml portions of cold 5% aqueous sodium carbonate, then washed with two 300 ml portions of water and dried over $Na_2SO_4$. Evaporation gave the product as an oil which slowly crystallized. Recrystallization from 2-propanol yielded 26 g of the title compound, mp 81°–83°.

Anal. Calcd for $C_{15}H_{16}N_2O_4S$: C, 56.24; H, 5.03; N, 8.74; S, 10.01. Found: C, 56.48; H, 4.97; N, 8.54; S, 10.17.

B. 2-Hydroxymethyl-5-dimethylaminomethylthiazole

5-Carbethoxy-2-(N-carbophenoxy-N-methylamino)-methylthiazole (19.8 g; 0.62 moles) [prepared in Step A] was added to a cold (5°) stirred suspension of lithium aluminum hydride (6.12 g; 0.16 moles) in 544 ml of dry tetrahydrofuran. The reaction mixture was heated to reflux temperature for 0.5 hour and then cooled to ambient temperature and decomposed, filtered through celite and evaporated under reduced pressure. The residue was dissolved in 80 ml of 3 N HCl and extracted with ether. The aqueous phase was adjusted to pH 8 and extracted with methylene chloride. The organic phase was dried, filtered and evaporated under vacuum to give 6.0 g of the title compound as an oil. The NMR spectrum (60 MHz) in CDCl$_3$ gave the following resonances δ: 7.50 (s, 1H); 4.85 (s, 2H); 4.15 (s, 1H); 3.75 (s, 2H); 2.35 (s, 6H).

C. 2-Chloromethyl-5-dimethylaminomethylthiazole hydrochloride

Thionyl chloride (27.4 g; 0.16 moles) was added dropwise to a cooled (ice-water bath) solution of 5-hydroxymethyl-2-dimethylaminomethylthiazole (8.9 g; 52.0 mmoles) [prepared in Step B] in 300 ml of methylene chloride. The mixture was heated at reflux temperature for 2 hours and then cooled and evaporated under reduced pressure to give 12.3 g of product. Crystallization from acetonitrile yielded the title compound, mp 143°–144°.

Anal. Calcd for C$_7$H$_{12}$Cl$_2$N$_2$S: C, 37.01; H, 5.32; N, 12.33; Cl, 31.63. Found (corr. for 0.91% H$_2$O): C, 36.88; H, 5.11; N, 12.14; Cl, 31.65.

D. 2-[(2-Dimethylaminomethylthiazol-5-yl)methylthio]ethylamine

Cysteamine hydrochloride (0.2 g; 1.76 mmoles) and 5-chloromethyl-2-dimethylaminomethylthiazole hydrochloride (0.4 g; 1.76 mmoles) [prepared in Step C] were dissolved in 2.5 ml of concentrated hydrochloric acid and the solution was heated at an oil bath temperature of 100°. After 2 hours, the mixture was evaporated under reduced pressure and the residue made basic with 40% aqueous sodium hydroxide solution. The aqueous phase was extracted with methyl acetate and the organic phase was dried, filtered and evaporated to give 0.3 g of the title compound as an oil. The NMR spectrum (60 MHz) in CDCl$_3$ gave the following resonances δ: 7.50 (s, 1H), 3.95 (s, 2H); 3.76 (s, 2H); 2.85 (m, 4H); 2.40 (s, 6H), 1.85 (s, 2H).

E. 3-{2-[(2-Dimethylaminomethylthiazol-5-yl)methylthio]ethylamino}-4-methylamino-1,2,5-thiadiazole 1,1-dioxide A solution of 2-[(2-dimethylaminomethylthiazol-5-yl)methylthio]ethylamine (1.55 g; 6.7 mmoles) [prepared in Step D] in 60 ml of methanol was added dropwise over 40 minutes to a partial suspension of 3,4-dimethoxy-1,2,5-thiadiazole 1,1-dioxide (1.19 g; 6.7 mmoles) in 130 ml of methanol that had been cooled to 8°. Upon completion of the addition, anhydrous methylamine was bubbled into the solution for 8 minutes, then stirred at ambient temperature overnight. The reaction mixture was evaporated under reduced pressure and the residue chromatographed on 150 g of silica gel using a gradient elution of acetonitrilemethanol. The appropriate fractions were combined to give 1.05 g of product. Recrystallization from 2-propanol yielded the title compound, mp 170°–172°.

Anal. Calcd for C$_{12}$H$_{20}$N$_6$O$_2$S$_3$: C, 38.28; H, 5.36; N, 22.33; S, 25.56. Found: C, 38.31; H, 5.32; N, 22.13; S, 25.96.

EXAMPLE 115

3-{2-[(2-Guanidinothiazol-4-yl)methylthio]ethylamino}-4-methylamino-1,2,5-thiadiazole 1-oxide The general procedure of Example 31 is repeated except that the 3,4-dimethoxy-1,2,5-thiadiazole 1,1-dioxide utilized therein was replaced by an equimolar amount of the corresponding 1-oxide. The appropriate fractions from column chromatography were combined to give 4.5 g of product. Crystallization from absolute ethanol yielded 3.05 g of the title compound, mp 175°–177°.

Anal. Calcd for C$_{10}$H$_{16}$N$_8$OS$_3$: C, 33.32; H, 4.47; N, 31.09; S, 26.68. Found: C, 33.10; H, 4.42; N, 31.00; S, 26.51.

EXAMPLE 116

3-{2-[(2-Guanidinothiazol-4-yl)methylthio]ethylamino}-4-hydroxy-1,2,5-thiadiazole 1-oxide A solution of 2-[(2-guanidinothiazol-4-yl)methylthio]ethylamine (4.15 g; 17.9 mmoles) in 50 ml of methanol was added dropwise over a 30 minute period to a solution of 3,4-dimethoxy-1,2,5-thiadiazole 1-oxide (2.91 g; 17.9 mmoles) in 350 ml of methanol that had been cooled in an ice-water bath. The reaction mixture was treated with a solution of sodium hydroxide pellets (3.58 g; 89.5 mmoles) in methanol. After stirring overnight at ambient temperature, the mixture was neutralized with 14.9 ml (89.5 mmoles) of aqueous 6.0 N HCl and after 10 minutes was evaporated under reduced pressure. The solid residue was triturated for 2 hours with 70 ml of water at ambient temperature and filtered to give product. Recrystallization from water yielded the title compound, mp 148°–151°.

Anal. Calcd for C$_9$H$_{13}$N$_7$O$_2$S$_3$: C, 31.11; H, 3.77; N, 28.22; S, 27.69. Found (corr. for 5.52% H$_2$O): C, 30.95; H, 3.76; N, 28.27; S, 28.11.

EXAMPLE 117

3-Amino-4-{2-[(2-{2-methylguanidino}thiazol-4-yl)methylthio]ethylamino}-1,2,5-thiadiazole 1-oxide A. 2-{[2-(2-Methylguanidino)thiazol-4-yl]methylthio}ethylamine Cysteamine hydrochloride (1.89 g; 16.6 mmoles) and 2-(2-methylguanidino)-4-chloromethylthiazole hydrochloride (4.0 g; 16.6 mmoles) [prepared from (N-methylamidino)thiourea and 1,3-dichloro-2-propanone] were combined in 20 ml of concentrated hydrochloric acid and the solution was heated at an oil bath temperature of 100°. After 2 hours the mixture was evaporated under reduced pressure and the residue made basic with 40% aqueous NaOH solution. The aqueous phase was extracted several times with methyl acetate and the organic phase was dried, filtered and evaporated to give 3.35 g of the title compound. The NMR spectrum (60 MHz) in D$_2$O gave the following characteristic resonances δ: 6.52 (s, 1H), 3.60 (s, 2H), 2.70 (m, 7H).

B. 3-Amino-4-{2-[(2-{2-methylguanidino}thiazol-4-yl)methylthio]ethylamino}-1,2,5-thiadiazole 1-oxide A solution of 2-[(2-{2-methylguanidino}thiazol-4-yl)methylthio]ethylamine (2.1 g; 8.56 mmoles) [prepared in Step A] in 50 ml of methanol was added dropwise over 30 minutes to a solution of 3,4-dimethoxy-1,2,5-thiadiazole 1-oxide (1.39 g; 8.56 mmoles) in 170 ml of methanol that had been cooled to 7°. Anhydrous ammonia was bubbled into the solution for 7 minutes, then stirred at ambient temperature overnight. The reaction mixture was evaporated under reduced pressure and the residue chromatographed on 100 g of silica gel (230–400 mesh) by flash chromatography using a gradient elution of acetonitrile-methanol. The appropriate fractions were combined, evaporated and the residue chromatographed on a Preparative HPLC system using μ-porasil silica gel. The appropriate fractions were combined, concentrated to a small volume and filtered to yield the title compound, mp 86°–91°; the NMR spectrum (100 MHz) in $d_6$ dimethyl sulfoxide showed the presence of approximately 0.8 moles of ethanol.

Anal. Calcd for $C_{10}H_{16}N_8OS_3 \cdot 0.8\ C_2H_6O$: C, 35.06; H, 5.28; N, 28.20; S, 24.21. Found (corr. for 1.64% $H_2O$): C, 35.66; H, 5.05; N, 28.33; S, 23.96.

EXAMPLE 118

3-Amino-4-[3-(3-dimethylaminomethylphenoxy)-propylamino]-1,2,5-thiadiazole 1-oxide A solution of 3-[3-(dimethylaminomethyl)phenoxy]-propylamine (2.5 g; 12.9 mmoles) in 35 ml of methanol was added dropwise over a period of 30 minutes to a stirred solution of 3,4-dimethoxy-1,2,5-thiadiazole 1-oxide in 200 ml of methanol that had been cooled to 2° in an ice-water bath. After stirring for 15 minutes, anhydrous ammonia was bubbled into the solution for 5 minutes. The reaction mixture was evaporated under reduced pressure to give crystalline product. Two recrystallizations from methanol yielded the title compound, mp 165.5°–166.5° (dec.).

Anal. Calcd for $C_{14}H_{21}N_5O_2S$: C, 51.99; H, 6.55; N, 21.66; S, 9.92. Found: C, 51.58; H, 6.49; N, 22.03; S, 10.19.

EXAMPLE 119

3-Amino-4-{2-[(2-methylaminothiazol-4-yl)methylthio]ethylamino}-1,2,5-thiadiazole 1-oxide A. 2-[(2-Methylaminothiazol-4-yl)methylthio]ethylamine Cysteamine hydrochloride (2.8 g; 24.6 mmoles) and 2-methylamino-4-chloromethylthiazole (4.0 g; 24.6 mmoles) [prepared from N-methylthiourea and 1,3-dichloro-2-propane] were dissolved in 20 ml of concentrated hydrochloric acid and the solution was heated at an oil bath temperature of 100°. After 30 hours of heating, the reaction mixture was evaporated under reduced pressure and the residue made basic with 40% aqueous NaOH solution. The aqueous phase was extracted with methyl acetate, dried, filtered and evaporated to give 1.75 g of the title compound as an oil which was used without further purification in Step B.

B.

3-Amino-4-{2-[(2-methylaminothiazol-4-yl)methylthio]ethylamino}-1,2,5-thiadiazole 1-oxide The product of Step A, above, was reacted sequentially with 3,4-dimethoxy-1,2,5-thiadiazole 1-oxide and anhydrous ammonia according to the general procedure of Example 117, Step B, and chromatographed as described therein. The appropriate fractions from flash chromatography were combined and evaporated to give 0.5 g of product as a foam. Crystallization from acetone yielded the title compound, mp 180°–183° (dec.).

Anal. Calcd for $C_9H_{14}N_6OS_3$: C, 33.94; H, 4.43; N, 26.39; S, 30.21. Found (corr. for 1.41% $H_2O$): C, 33.96; H, 4.11; N, 26.27; S, 30.44.

EXAMPLE 120

3-Amino-4-{2-[(2-{2,3-dimethylguanidino}thiazol-4-yl)methylthio]ethylamino}-1,2,5-thiadiazole 1-oxide A. 2-[(2-{2,3-Dimethylguanidino}thiazol-4-yl)methylthio]ethylamine dihydrochloride Cysteamine hydrochloride (2.25 g; 19.6 mmoles) and 4-chloromethyl-2-(2,3-dimethylguanidino)thiazole (5 g; 19.6 mmoles) [prepared from 1,3-dichloro-2-propanone and (N,N'-dimethylamidino)thiourea which is itself prepared from dimethyl cyanodithioiminocarbonate and methylamine] were dissolved in 17.5 ml of concentrated hydrochloric acid and heated at an oil bath temperature of 100°. After 24 hours the reaction mixture was evaporated under reduced pressure and the residue crystallized from absolute ethanol to yield the title compound, mp 243°–245°.

B.

3-Amino-4-{2-[(2-{2,3-dimethylguanidino}thiazol-4-yl)methylthio]ethylamino}-1,2,5-thiadiazole 1-oxide The product of Step A, above, was sequentially reacted with 3,4-dimethoxy-1,2,5-thiadiazole 1-oxide and anhydrous ammonia by the general procedure of Example 117, Step B. The crude reaction mixture was evaporated under reduced pressure and the residue crystallized from methanol to give the title compound, mp 201°–203° (dec.).

Anal. Calcd for $C_{11}H_{18}N_8OS_3$: C, 35.28; H, 4.84; N, 29.92; S, 25.69. Found (corr. for 0.88% $H_2O$): C, 34.93; H, 4.56; N, 30.27; S, 25.92.

EXAMPLE 121

3,4-Bis-{2-[(2guanidinothiazol-4-yl)methylthio]ethylamino}-1,2,5-thiadiazole 1-oxide To a solution of sodium methoxide (2.16 g; 40.0 mmoles) in 100 ml of $CH_3OH$ that was cooled to 0° in an ice-water bath was added 2-[(2-guanidinothiazol-4-yl)methylthio]ethylamine dihydrochloride (6.09 g; 20.0 mmoles) and, after 20 minutes of stirring, the solution was treated with 3,4-dimethoxy-1,2,5-thiadiazole 1-oxide (1.62 g; 10 mmoles). The reaction mixture was stirred at ambient temperature for 65 hours and evaporated under reduced pressure. The residue was chromatographed on 100 g of silica gel (230–400 mesh) by flash chromatography using a gradient elution of acetonitrile-methanol. The appropriate fractions were combined, evaporated and the residue chromatographed on a Preparative HPLC system using μ-porasil silica gel. The appropriate fractions were combined, and evaporated under reduced pressure to give the title compound as an amorphous solid; the NMR spectrum (100 MHz) in $d_6$ dimethyl sulfoxide showed the presence of approximately 0.11 mole of ethanol.

Anal. Calcd for $C_{16}H_{24}N_{12}OS_5 \cdot 0.11 C_2H_6O$: C, 34.42; H, 4.39; N, 29.71; S, 28.33. Found (corr. for 1.86% $H_2O$): C, 34.95; H, 4.41; N, 29.04; S, 27.71.

EXAMPLE 122

3-{2-[(2-Aminothiazol-4-yl)methylthio]ethylamino}-4-methylamino-1,2,5-thiadiazole 1,1-dioxide A. 2-[(2-Aminothiazol-4-yl)methylthio]ethylamine dihydrochloride Cysteamine hydrochloride (5.65 g; 50.0 mmoles) and 2-amino-4-chloromethylthiazole hydrochloride (9.25 g; 50.0 mmoles) were dissolved in 70 ml of concentrated hydrochloric acid and heated at an oil bath temperature of 105°. After 64 hours of heating the mixture was evaporated under reduced pressure and the residue triturated with acetone. The collected product was retriturated with ethanol, filtered and dried to yield the title compound, mp 170°–200°.

Anal. Calcd for $C_6H_{13}Cl_2N_3S_2$: C, 27.48; H, 4.90; N, 16.02; S, 24.46; Cl, 27.04. Found: C, 27.29; H, 5.07; N, 15.91; S, 24.15; Cl, 27.24.

B.  3-{2-[(2-Aminothiazol-4-yl)methylthio]ethylamino}-4-methylamino-1,2,5-thiadiazole 1,1-dioxide A solution of 2-[(2-aminothiazol-4-yl)methylthio]ethylamine (from the dihydrochloride, 3.0 g; 11.4 mmoles) [prepared in Step A] in 25 ml of methanol as added dropwise over 1.5 hours to a cold (5°), stirred, partial suspension of 3,4-dimethoxy-1,2,5-thiadiazole 1,1-dioxide (2.03 g; 11.4 mmoles) in 55 ml of methanol. After 1.5 hours, anhydrous methylamine was bubbled into the solution for 30 minutes and stirred at 5° for 19 hours. The reaction mixture was evaporated under reduced pressure and the residue placed on 400 g of silica gel and chromatographed using acetone-methylene chloride (7:3). The appropriate fractions were combined and evaporated to give product. Recrystallization from 95% ethanol yielded the title compound, mp 200°–201°.

Anal. Calcd for $C_9H_{14}N_6O_2S_3$: C, 32.32; H, 4.32; N, 25.13; S, 28.76. Found: C, 32.25; H, 4.20; N, 25.06; S, 29.14.

EXAMPLE 123

3-Amino-4-{2-[(2-dimethylaminomethylthiazol-5-yl)methylthio]ethylamino}-1,2,5-thiadiazole 1-oxide A solution of 2-[(2-dimethylaminomethylthiazol-5-yl)methylthio]ethylamine (2.05 g; 8.86 mmoles) [prepared in Example 114, Step D] in 70 ml of methanol was added dropwise to a cold (8°), stirred, solution of 3,4-dimethoxy-1,2,5-thiadiazole 1-oxide (1.44 g; 8.88 mmoles) in 170 ml of methanol. Anhydrous ammonia was bubbled into the solution for 8 minutes and then stirred at ambient temperature for 0.5 hours. The reaction mixture was evaporated under reduced pressure and the residue triturated with acetonitrile to give 1.76 g of product. The product was purified by flash chromatography on 100 g of silica gel (230–400 mesh) using acetonitrile-methanol. The appropriate fractions were combined, evaporated and the residue crystallized from acetone to yield the title compound, mp 131°–133°.

Anal. Calcd for $C_{11}H_{17}N_6OS_3$: C, 38.13; H, 5.24; N, 24.26; S, 27.76. Found (corr. for 0.49% $H_2O$): C, 37.86; H, 5.06; N, 24.34; S, 27.68.

EXAMPLE 124

3-Amino-4-{2-[(2-aminothiazol-4-yl)methylthio]ethylamino}-1,2,5-thiadiazole 1-oxide A solution of 2-[(2-aminothiazol-4-yl)methylthio]ethylamine (from the dihydrochloride, 2.62 g; 10.0 mmoles) [prepared in Example 122, Step A] in 20 ml of methanol was added dropwise over 30 minutes to a cold (5°) solution of 3,4-dimethoxy-1,2,5-thiadiazole 1-oxide (1.62 g; 10.0 mmoles) in 50 ml of methanol. After stirring for 1.5 hours, anhydrous ammonia was bubbled into the solution for 30 minutes and the solution kept at 5° for 17 hours. The reaction mixture was evaporated under reduced pressure and the residue was chromatographed on a Preparative HPLC system using μ-porasil silica gel. The appropriate fractions were combined and evaporated under reduced pressure to give the title compound as an amorphous solid; the NMR spectrum (100 MHz) in $d_6$ dimethyl sulfoxide showed the presence of approximately 0.4 moles of ethanol.

Anal. Calcd for $C_8H_{12}N_6OS_3 \cdot 0.4C_2H_6O$: C, 32.74; H, 4.50; N, 26.03; S, 29.80. Found (corr. for 1.39% $H_2O$): C, 32.39; H, 4.28; N, 28.39; S, 30.02.

EXAMPLE 125

3-Methylamino-4-{2-[(2-{2,3-dimethylguanidino}-thiazol-4-yl)methylthio]ethylamino}-1,2,5-thiadiazole 1,1-dioxide A solution of 2-[(2-{2,3-dimethylguanidino}thiazol-4-yl)methylthio]ethylamine (2.5 g; 9.64 mmoles) [prepared in Example 120, Step A] in methanol was added dropwise over a period of 40 minutes to a cold (8°), stirred suspension of 3,4-dimethoxy-1,2,5-thiadiazole 1,1-dioxide (1.72 g; 9.64 mmoles) in 270 ml of methanol. Anhydrous methylamine was bubbled into the solution for 7 minutes and the solution then was evaporated under reduced pressure. The residue was chromatographed on 100 g of silica gel (230–400 mesh) by flash chromatography and the appropriate fractions were combined and evaporated to give 2.5 g of product as a foam. Crystallization from aqueous ethanol yielded the title compound, mp 132°–137°.

Anal. Calcd for $C_{12}H_{20}N_8O_2S_3$: C, 35.63; H, 4.98; N, 27.70; S, 23.78. Found (corr. for 4.78% $H_2O$): C, 35.74; H, 5.04; N, 27.87; S, 23.56.

EXAMPLE 126

3-{2-[(2-Dimethylaminothiazol-4-yl)methylthio]ethylamino}-4-amino-1,2,5-thiadiazole 1-oxide A. 2-[(2-Dimethylaminothiazol-4-yl)methylthio]ethylamine Cysteamine hydrochloride (5.24 g; 45.9 mmoles) and 2-dimethylamino-4-chloromethylthiazole hydrochloride (9.8 g; 45.9 mmoles) [prepared from N,N-dimethylthiourea and 1,3-dichloro-2-propanone] were dissolved in 45 ml of concentrated hydrochloric acid and heated at an oil bath temperature of 100° for 96 hours. The mixture was evaporated under reduced pressure and the residue made basic with 40% aqueous NaOH. The aqueous phase was extracted with methyl acetate, dried and evaporated to give the title compound as an oil which was used without further purification in Step B.

The NMR spectrum (60 MHz) in $D_2O$ gave the following resonances δ: 6.97 (s, 1H); 3.94 (s, 2H); 3.67 (s, 3H); 3.15 (s, 3H); 3.05 (m, 4H).

B. 3-{2-[(2-Dimethylaminothiazol-4-yl)methylthio]ethylamino}-4-amino-1,2,5-thiadiazole 1-oxide A solution of 2-[(2-dimethylaminothiazol-4-yl)methylthio]ethylamine (3.5 g; 16.1 mmoles) [prepared in Step A] in 70 ml of methanol was added dropwise over a period of 30 minutes to a cold (7°), stirred solution of 3,4-dimethoxy-1,2,5-thiadiazole 1-oxide (2.61 g; 16.1 mmoles) in 200 ml of methanol. Anhydrous ammonia was bubbled into the solution for 8 minutes and after stirring for 30 minutes the mixture was evaporated under reduced pressure. The residue was triturated with isopropyl alcohol then dissolved in methanol, filtered and evaporated to give product. The product was purified by flash chromatography on 100 g of silica gel (230–400 mesh) using methylene chloride-methanol. The appropriate fractions were combined and rechromatographed by HPLC on a μ-porasil silica gel column. The appropriate fractions were combined and evaporated under reduced pressure to yield the title compound, mp 116°–122°; the NMR spectrum (100 MHz) in d₆ dimethyl sulfoxide showed the presence of approximately ⅓ mole of ethanol.

Anal. Calcd for $C_{10}H_{16}N_6OS_3 \cdot \frac{1}{3} C_2H_6O$: C, 36.83; H, 5.22; N, 24.16. Found (corr. for 11.92% $H_2O$): C, 36.61; H, 4.06; N, 24.22.

EXAMPLE 127

3-{2-[(2-Dimethylaminothiazol-4-yl)methylthio]ethylamino}-4-methylamino-1,2,5-thiadiazole 1,1-dioxide A solution of 2-[(2-dimethylaminothiazol-4-yl)methylthio]ethylamine (2.5 g; 11.5 mmoles) [prepared in Example 126, Step A] was added dropwise over a period of 30 minutes to a cold (7°), stirred suspension of 3,4-dimethoxy-1,2,5-thiadiazole 1,1-dioxide (2.05 g; 11.5 mmoles) in 200 ml of methanol. Anhydrous methylamine was bubbled into the solution for 7 minutes and after stirring for 30 minutes, the mixture was evaporated under reduced pressure. The residue was crystallized from methanol to give 1.6 g of product. Two recrystallizations from 2-methoxyethanol yielded the title compound, mp 227°–229°.

EXAMPLE 128

3-{2-[(2-{2-Imidazolidinyl}iminothiazol-4-yl)methylthio]ethylamino}-4-methylamino-1,2,5-thiadiazole 1,1-dioxide A. 2-[(2-{2-Imidazolidinyl}iminothiazol-4-yl)methylthio]ethylamine Cysteamine hydrochloride (2.22 g; 19.5 mmoles) and 2-[(2-imidazolidinyl)imino]-4-chloromethylthiazole hydrochloride (4.94 g; 19.51 mmoles) [prepared from 1,3-dichloro-2-propanone and N-(2-imidazolidin-2-yl)thiourea which is itself prepared from 2-(cyanimino)imidazolidine] were dissolved in 20 ml of concentrated hydrochloric acid and heated at an oil bath temperature of 100° for 5.5 hours. The reaction mixture was evaporated under reduced pressure and the residue made basic with 40% NaOH. The aqueous phase was extracted with methyl acetate, dried and evaporated to give 2.02 g of the title compound which was used in the next step without further purification.

B. 3-{2-[(2-{2-Imidazolidinyl}iminothiazol-4-yl)methylthio]ethylamino}-4-methylamino-1,2,5-thiadiazole 1,1-dioxide A solution of 2-[(2-{2-imidazolidinyl}iminothiazol-4-yl)methylthio]ethylamine (2.02 g; 7.85 mmoles) [prepared in Step A] in 85 ml of methanol was added dropwise over 40 minutes to a cold (8°), stirred suspension of 3,4-dimethoxy-1,2,5-thiadiazole 1,1-dioxide (1.4 g; 7.85 mmoles) in 190 ml of methanol. Anhydrous methylamine was bubbled into the solution for 7 minutes and, after 30 minutes at ambient temperature, the mixture was evaporated under reduced pressure to give 3.5 g of product. The product was chromatographed on a Preparative HPLC system using μ-porasil silica gel. The appropriate fractions were combined, evaporated and the residue crystallized from methanol to give the title compound, mp 229°–231°. Recrystallization from aqueous ethanol gave the title compound with mp 136°–140° which resolidified with remelting at mp 219°–224°.

Anal. Calcd for $C_{12}H_{18}N_8O_2S_3$: C, 35.81; H, 4.51; N, 27.84; S, 23.90. Found (corr. for 4.59% $H_2O$): C, 35.51; H, 4.43; N, 27.98; S, 23.56.

EXAMPLE 129

3-{2-[(5-Dimethylaminomethyl-2-thienyl)methylthio]ethylamino}-4-[(2-pyridyl)methylamino]-1,2,5-thiadiazole 1,1-dioxide The general procedure of Example 65 was repeated except that the methylamine utilized therein was replaced by an equimolar amount of 2-aminomethylpyridine. Column chromatography of the crude solid yielded 3.08 g of product. Recrystallization from isopropyl alcohol yielded the title compound, mp 162°–164° (dec.).

Anal. Calcd for $C_{18}H_{24}N_6O_2S_3$: C, 47.76; H, 5.34; N, 18.57. Found: C, 47.80; H, 5.32; N. 18.75.

EXAMPLE 130

3-{2-[(5-Dimethylaminomethyl-2-thienyl)methylthio]ethylamino}-4-[(4-pyridyl)methylamino]-1,2,5-thiadiazole 1,1-dioxide The general procedure of Example 65 was repeated except that the methylamine utilized therein was replaced by an equimolar amount of 4-aminomethylpyridine. After chromatography the crude product was dissolved in hot isopropyl alcohol, decanted from insoluble material and the solution treated with anhydrous HCl to give the title compound as the hydrochloride salt. This salt was dissolved in water and made alkaline with saturated aqueous sodium bicarbonate solution to give, after filtration, the title compound as a free base, mp 88°–90°.

Anal. Calcd. for $C_{18}H_{24}N_6O_2S_3$: C, 47.76; H, 5.34; N, 18.57. Found (corr. for 3.73% $H_2O$): C, 47.54; H, 5.32; N, 19.09.

EXAMPLE 131

3-{2-[(5-Dimethylaminomethyl-2-thienyl)methylthio]ethylamino}-4-ethylamino-1,2,5-thiadiazole 1,1-dioxide The general procedure of Example 65 was repeated except that the methylamine utilized therein was replaced by an equimolar amount of ethylamine. The appropriate fractions from column chromatography were dissolved in warm isopropyl alcohol and saturated with anhydrous HCl. The crystalline solid was collected by filtration, washed with acetone and dried to give 2.9 g of the title compound as its hydrochloride salt, mp 246°–247° (dec.).

Anal. Calcd for $C_{14}H_{24}ClN_5O_2S_3$: C, 39.47; H, 5.68; N, 16.44; Cl, 8.32. Found: C, 39.81; H, 5.74; N, 16.62; Cl, 8.20.

EXAMPLE 132

3-Methylamino-4-[3-(3-piperidinomethylphenoxy)propylamino]-1,2,5-thiadiazole 1,1-dioxide A solution of 3-(3-piperidinomethylphenoxy)propylamine (2.35 g; 9.45 mmoles) [prepared according to published U.K. patent application No. 2,023,133] in 30 ml of methanol was added dropwise over a period of 40 minutes to a stirred partial suspension of 3,4-dimethoxy-1,2,5-thiadiazole 1,1-dioxide (1.68 g; 9.45 mmoles) that had been cooled to 1° in an ice-water bath. After 15 minutes, anhydrous methylamine was bubbled into the solution for 5 minutes and the solution then was stirred at ambient temperature for 30 minutes. The reaction mixture was evaporated under reduced pressure and the residue chromatographed by flash chromatography on 100 g of silica gel (230–400 mesh) using methanol-acetonitrile. The appropriate fractions were combined and evaporated to give 2.2 g of product. Recrystallization from acetonitrile with charcoal treatment yielded the title compound, mp 182°–184°.

Anal. Calcd for $C_{18}H_{27}N_5O_3S$: C, 54.94; H, 6.92; N, 17.80; S, 8.15. Found: C, 54.90; H, 7.07; N, 18.14; S, 8.29.

EXAMPLE 133

3-Amino-4-[3-(3-piperidinomethylphenoxy)-propylamino]-1,2,5-thiadiazole 1-oxide

A solution of 3-(3-piperidinomethylphenoxy)propylamine (from the dihydrochloride, 4.0 g; 12.4 mmoles) in 40 ml of methanol was added dropwise over a period of 50 minutes to a solution of 3,4-dimethoxy-1,2,5-thiadiazole 1-oxide (2.01 g; 12.4 mmoles) in 200 ml of methanol that had been cooled to 0° in an ice-water bath. After 15 minutes, anhydrous ammonia was bubbled into the solution for 5 minutes and the solution then was stirred at ambient temperature for 17 hours. The reaction mixture was evaporated under reduced pressure and the residue chromatographed by flash chromatography on 100 g of silica gel (230–400 mesh) using methanol-acetonitrile. The appropriate fractions were combined and evaporated to give 4.18 g of product. Recrystallization from 95% aqueous ethanol yielded the title compound, mp 155°–157° (dec.).

Anal. Calcd for $C_{17}H_{25}N_5O_2S$: C, 56.17; H, 6.93; N, 19.27; S, 8.82. Found: C, 55.97; H, 7.04; N, 19.57; S, 8.63.

EXAMPLE 134

3-Amino-4-[3-(3-piperidinomethylphenoxy)-propylamino]-1,2,5-thiadiazole 1,1-dioxide A solution of 3-(3-piperidinomethylphenoxy)propylamine (from the dihydrochloride, 4.0 g; 12.4 mmoles) in 35 ml of methanol was added dropwise over a period of 65 minutes to a stirred partial suspension of 3,4-dimethoxy-1,2,5-thiadiazole 1-oxide (2.22 g; 12.4 mmoles) in 200 ml of methanol that had been cooled to 2° in an ice-water bath. After 15 minutes anhydrous ammonia was bubbled into the solution for 5 minutes and the solution then was stirred at ambient temperature for 30 minutes. The reaction mixture was evaporated under reduced pressure and the residue placed on 100 g of silica gel (230–400 mesh) and chromatographed by flash chromatography using methanol-acetonitrile. The appropriate fractions were combined and evaporated to give 3.2 g of product. The NMR spectrum (100 MHz) in $d_6$ dimethyl sulfoxide showed the following resonances δ: 7.2 (m, 1H); 6.9 (m, 3H); 4.1 (t, 2H); 3.5 (t, 2H); 3.4 (s, 2H); 2.3 (m, 4H); 2.0 (m, 2H); 1.4 (broad s, 6H).

EXAMPLE 135

3-{2-[(5-Dimethylaminomethyl-2-thienyl)methylthio]ethylamino}-4-(3,4-methylenedioxybenzylamino)-1,2,5-thiadiazole 1,1-dioxide A solution of 2-[(5-dimethylaminomethyl-2-thienyl)methylthio]ethylamine (2.02 g; 8.8 mmoles) in 30 ml of methanol was added dropwise over a period of 40 minutes to a stirred solution of 3,4-dimethoxy-1,2,5-thiadiazole 1,1-dioxide (1.56 g; 8.8 mmoles) in 200 ml of methanol that had been cooled to 0° in an ice-water bath. After 20 minutes, piperonylamine (1.46 g; 9.6 mmoles) was added and the mixture stirred at ambient temperature for 3 hours. The reaction mixture was evaporated to near dryness, ether was added, and the mixture was filtered to give 3.47 g of product. Recrystallization from methanol yielded the title compound, mp 180°–182°.

Anal. Calcd for $C_{20}H_{25}N_5O_4S_3$: C, 48.46; H, 5.08; N, 14.13. Found (corr. for 0.38% $H_2O$): C, 48.92; H, 4.88; N, 14.52.

EXAMPLE 136

3-Amino-4-{2-[(6-dimethylaminomethyl-2-pyridyl)methylthio]ethylamino}-1,2,5-thiadiazole 1-oxide A. 6-(N,N-dimethylcarbamyl)-2-carbomethoxypyridine A solution of 6-carbomethoxy-2-picolinic acid (22.8 g; 0.13 mole) in 80 ml of thionyl chloride was heated at an oil bath temperature of 100° for 3 hours. The solution was evaporated under reduced pressure and the residue dissolved in 200 ml of dioxane which then was added dropwise to a solution of dimethylamine (70 g) in dioxane. The reaction mixture was stirred for 2 hours and then allowed to stand at 4° overnight, filtered and evaporated under reduced pressure. The residue was dissolved in toluene, diluted with methylcyclohexane and filtered to give 20.7 g of the title compound, mp 90°–92°.

Anal. Calcd for $C_{10}H_{12}N_2O_3$: C, 57.68; H, 5.81; N, 13.46. Found: C, 57.64; H, 5.85; N, 13.77.

B. 6-Dimethylaminomethyl-2-hydroxymethylpyridine

A solution of 6-(N,N-dimethylcarbamyl-2-carbomethoxypyridine (20.3 g; 97.5 mmoles) [prepared in Step A] in 200 ml of tetrahydrofuran was added to a suspension of lithium aluminum hydride (9.6 g; 0.25 moles) in 500 ml of tetrahydrofuran. The mixture was stirred and heated at reflux temperature under a nitrogen atmosphere for 3 hours then left at ambient temperature overnight. The mixture was decomposed with a saturated aqueous solution of $Na_2SO_4$, filtered, dried and evaporated under reduced pressure. The residue was placed on 275 g of aluminum oxide and eluted with methylene chloride. The appropriate fractions were combined and evaporated to give 5.2 g of the title compound.

The NMR spectrum (60 MHz) in $CDCl_3$ gave the following resonances δ: 7.38 (m, 3H); 4.75 (s, 2H); 3.58 (s, 2H); 2.27 (s, 6H).

C. 2-[(6-Dimethylaminomethyl-2-pyridyl)methylthio]ethylamine

Cysteamine hydrochloride (3.58 g; 31.5 mmoles) and 6-dimethylaminomethyl-2-hydroxymethylpyridine (5.0 g; 30.1 mmole) [prepared in Step B] were dissolved in 50 ml of 48% hydrobromic acid and the solution heated at reflux temperature for 12 hours and then allowed to stand at ambient temperature for 8 hours. The reaction mixture was evaporated under reduced pressure to half volume, made basic with 40% aqueous NaOH and extracted with several portions of methylene chloride. The combined organic phase was washed with a small amount of water and saturated brine solution then dried and evaporated under reduced pressure to yield 3.14 g of the title compound.

The NMR spectrum (60 MHz) in $CDCl_3$ gave the following resonances δ: 7.5 (m, 3H); 3.83 (s, 2H); 3.56 (s, 2H); 2.7 (m, 4H); 2.28 (s, 6H).

D. 3-Amino-4-{2-[(6-dimethylaminomethyl-2-pyridyl)methylthio]ethylamino}-1,2,5-thiadiazole 1-oxide When a methanolic solution of 3,4-dimethoxy-1,2,5-thiadiazole 1-oxide is successively treated with an equimolar amount of 2-[(6-dimethylaminomethyl-2-pyridyl)methylthio]ethyalmine [prepared in Step C] and excess ammonia, the title compound is thereby produced.

EXAMPLE 137

3-Amino-4-{2-[(6-dimethylaminomethyl-2-pyridyl)methylthio]ethylamino}-1,2,5-thiadiazole 1,1-dioxide When a methanolic solution of 3,4-dimethoxy-1,2,5-thiadiazole 1,1-dioxide is successively treated with an equimolar amount of 2-[(6-dimethylaminomethyl-2-pyridyl)methylthio]ethylamine [prepared in Example 136, Step C] and excess ammonia, the title compound is thereby produced.

EXAMPLE 138

3-{2-[(5-Guanidino-1,2,4-thiadiazol-3-yl)methylthio]ethylamino}-4-methylamino-1,2,5-thiadiazole 1,1-dioxide When a methanolic solution of 3,4-dimethoxy-1,2,5-thiadiazole 1,1-dioxide is successively treated with an equimolar amount of 2-[(5-guanidino-1,2,4-thiadiazol-3-yl)methylthio]ethylamine [prepared according to the procedure described in published European Patent Application No. 6679] and excess methylamine, the title compound is thereby produced.

EXAMPLE 139

3-Amino-4-{2-[(5-guanidino-1,2,4-thiadiazol-3-yl)methylthio]ethylamino}-1,2,5-thiadiazole 1,1-dioxide When a methanolic solution of 3,4-dimethoxy-1,2,5-thiadiazole, 1,1-dioxide is successively treated with an equimolar amount of 2-[(5-guanidino-1,2,4-thiadiazol-3-yl)methylthio]ethylamine and excess ammonia, the title compound is thereby produced.

EXAMPLE 140

3-Amino-4-{2-[(5-guanidino-1,2,4-thiadiazol-3-yl)methylthio]ethylamino}-1,2,5-thiadiazole 1-oxide When a methanolic solution of 3,4-dimethoxy-1,2,5-thiadiazole 1-oxide is successively treated with an equimolar amount of 2-[(5-guanidino-1,2,4-thiadiazol-3-yl)methylthio]ethylamine and excess ammonia, the title compound is thereby produced.

EXAMPLE 141

3-{2-[(5-Guanidino-1,2,4-oxadiazol-3-yl)methylthio]ethylamino}-4-methylamino-1,2,5-thiadiazole 1,1-dioxide When a methanolic solution of 3,4-dimethoxy-1,2,5-thiadiazole 1,1-dioxide is successively treated with an equimolar amount of 2-[(5-guanidino-1,2,4-oxadiazol-3-yl)methylthio]ethylamine [prepared according to the procedure described in published European Patent Application No. 6286] and excess methylamine, the title compound is thereby produced.

EXAMPLE 142

3-Amino-4-{2-[(5-guanidino-1,2,4-oxadiazol-3-yl)methylthio]ethylamino}-1,2,5-thiadiazole 1,1-dioxide When a methanolic solution of 3,4-dimethoxy-1,2,5-thiadiazole 1,1-dioxide is successively treated with an equimolar amount of 2-[(5-guanidino-1,2,4-oxadiazol-3-yl)methylthio]ethylamine and excess ammonia, the title compound is thereby produced.

EXAMPLE 143

3-Amino-4-{2-[(5-guanidino-1,2,4-oxadiazol-3-yl)methylthio]ethylamino}-1,2,5-thiadiazole 1-oxide When a methanolic solution of 3,4-dimethoxy-1,2,5-thiadiazole 1-oxide is successively treated with an equimolar amount of 2-[(5-guanidino-1,2,4-oxadiazol-3-yl)methylthio]ethylamine and excess ammonia, the title compound is thereby produced.

EXAMPLE 144

The general procedure of Example 132 is repeated, except that the 3-(3-piperidinomethylphenoxy)propylamine utilized therein is replaced by an equimolar amount of (a) 3-(3-pyrrolidinomethylphenoxy)propylamine,
(b) 3-[3-(4-methylpiperidino)methylphenoxy]propylamine,
(c) 3-(3-homopiperidinomethylphenoxy)propylamine,
(d) 3-(3-morpholinomethylphenoxy)propylamine[1] and
(e) 3-[3-(N-methylpiperazino)methylphenoxy]propylamine[2], respectively, and there is thereby produced (a) 3-Methylamino-4-[3-(3-pyrrolidinomethylphenoxy)propylamino]-1,2,5-thiadiazole 1,1-dioxide, mp 156°–157° C.,
(b) 3-Methylamino-4-{3-[3-(4-methylpiperidino)methylphenoxy]propylamino}-1,2,5-thiadiazole 1,1-dioxide, mp 186°–189° C.,
(c) 3-Methylamino-4-[3-(3-homopiperidinomethylphenoxy)propylamino]-1,2,5-thiadiazole 1,1-dioxide, mp 174°–176° C. as the hydrochloride,
(d) 3-Methylamino-4-[3-(3-morpholinomethylphenoxy)propylamino]-1,2,5-thiadiazole 1,1-dioxide, mp 162°–163° C., and
(e) 3-Methylamino-4-{3-[3-(N-methylpiperazino)methylphenoxy]propylamino}-1,2,5-thiadiazole 1,1-dioxide, respectively.

The above starting materials (1) and (2) are prepared by hydrogenation of a mixture of N-[3-(3-formylphenoxy)propyl]phthalimide and the corresponding morpholine or N-methylpiperazine over 10% palladium/carbon catalyst and then removal of the phthalimido protecting group with hydrazine. The other starting materials are prepared according to the procedures described in published U.K. Patent Application No. 2,023,133.

EXAMPLE 145

The general procedure of Example 133 is repeated, except that the 3-(3-piperidinomethylphenoxy)propylamine utilized therein is replaced by an equimolar amount of (a) 3-(3-pyrrolidinomethylphenoxy)propylamine,
(b) 3-[3-(4-methylpiperidino)methylphenoxy]propylamine,
(c) 3-(3-homopiperidinomethylphenoxy)propylamine, (d) 3-[3-(heptamethyleneiminomethyl)phenoxy]-propylamine,
(e) 3-(3-morpholinomethylphenoxy)propylamine and
(f) 3-[3-(N-methylpiperazino)methylphenoxy]propylamine, respectively, and there is thereby produced
(a) 3-Amino-4-[3-(3-pyrrolidinomethylphenoxy)-propylamino]-1,2,5-thiadiazole 1-oxide, mp 168°–170° C. (dec.)
(b) 3-Amino-4-{3-[3-(4-methylpiperidino)methylphenoxy]propylamino}-1,2,5-thiadiazole 1-oxide, mp 157°–159° C.,
(c) 3-Amino-4-[3-(3-homopiperidinomethylphenoxy)-propylamino]-1,2,5-thiadiazole 1-oxide, mp 167°–169° C.,
(d) 3-Amino-4-{3-[3-(heptamethyleneiminomethyl)phenoxy]propylamino}-1,2,5-thiadiazole 1-oxide, mp 154°–157° C.,
(e) 3-Amino-4-[3-(3-morpholinomethylphenoxy)-propylamino]-1,2,5-thiadiazole 1-oxide and
(f) 3-Amino-4-{3-[3-(N-methylpiperazino)methylphenoxy]propylamino}-1,2,5-thiadiazole 1-oxide, respectively.

EXAMPLE 146

The general procedure of Example 134 is repeated, except that the 3-(3-(piperidinomethylphenoxy)-propylamine utilized therein is replaced by an equimolar amount of
(a) 3-(3-pyrrolidinomethylphenoxy)propylamine,
(b) 3-[3-(4-methylpiperidino)methylphenoxy]propylamine,
(c) 3-(3-homopiperidinomethylphenoxy)propylamine,
(d) 3-(3-morpholinomethylphenoxy)propylamine and
(e) 3-[3-(N-methylpiperazino)methylphenoxy]propylamine, respectively, and there is thereby produced
(a) 3-Amino-4-[3-(3-pyrrolidinomethylphenoxy)-propylamino]-1,2,5-thiadiazole 1,1-dioxide, mp 160°–163° C. (dec.)
(b) 3-Amino-4-{3-[3-(4-methylpiperidino)methylphenoxy]propylamino}-1,2,5-thiadiazole 1,1-dioxide,
(c) 3-Amino-4-[3-(3-homopiperidinomethylphenoxy)-propylamino]-1,2,5-thiadiazole 1,1-dioxide,
(d) 3-Amino-4-[3-(3-morpholinomethylphenoxy)-propylamino]-1,2,5-thiadiazole 1,1-dioxide, mp 172°–174° C. (dec.), and
(e) 3-Amino-4-{3-[3-(N-methylpiperazino)methylphenoxy]propylamino}-1,2,5-thiadiazole 1,1-dioxide, respectively.

EXAMPLE 147

The general procedure of Example 132 is repeated, except that the methylamine utilized therein is replaced by an equimolar amount of
ethylamine,
propylamine,
n-butylamine,
allylamine,
2-propynylamine,
cyclopropylamine,
aminomethylcyclopropane,
ethanolamine,
2-methoxyethylamine,
2,2,2-trifluoroethylamine,
2-fluoroethylamine,
hydroxyamine,
3-aminopropionitrile
benzylamine,
3-methoxybenzylamine,
4-methoxybenzylamine,
3,4-dimethoxybenzylamine,
piperonylamine,
4-chlorobenzylamine,
2-aminomethylpyridine,
3-aminomethylpyridine and
4-aminomethylpyridine, respectively, and there is thereby produced
3-Ethylamino-4-[3-(3-piperidinomethylphenoxy)-propylamino]-1,2,5-thiadiazole 1,1-dioxide,
3-Propylamino-4-[3-(3-piperidinomethylphenoxy)-propylamino]-1,2,5-thiadiazole 1,1-dioxide,
3-Butylamino-4-[3-(3-piperidinomethylphenoxy)-propylamino]-1,2,5-thiadiazole 1,1-dioxide,
3-Allylamino-4-[3-(3-piperidinomethylphenoxy)-propylamino]-1,2,5-thiadiazole 1,1-dioxide,
3-(2-Propynyl)amino-4-[3-(3-piperidinomethylphenoxy)propylamino]-1,2,5-thiadiazole 1,1-dioxide,
3-(Cyclopropylamino)-4-[3-(3-piperidinomethylphenoxy)propylamino]-1,2,5-thiadiazole 1,1-dioxide,
3-[(Cyclopropyl)methylamino]-4-[3-(3-piperidinomethylphenoxy)propylamino]-1,2,5-thiadiazole 1,1-dioxide,
3-(2-Hydroxyethylamino)-4-[3-(3-piperidinomethylphenoxy)propylamino]-1,2,5-thiadiazole 1,1-dioxide,
3-(2-Methoxyethylamino)-4-[3-(3-piperidinomethylphenoxy)propylamino]-1,2,5-thiadiazole 1,1-dioxide,
3-(2,2,2-trifluoroethylamino)-4-[3-(3-piperidinomethylphenoxy)propylamino]-1,2,5-thiadiazole 1,1-dioxide,
3-(2-Fluoroethylamino)-4-[3-(3-piperidinomethylphenoxy)propylamino]-1,2,5-thiadiazole 1,1-dioxide,
3-Hydroxyamino-4-[3-(3-piperidinomethylphenoxy)-propylamino]-1,2,5-thiadiazole 1,1-dioxide,
3-(3-Cyanopropylamino)-4-[3-(3-piperidinomethylphenoxy)propylamino]-1,2,5-thiadiazole 1,1-dioxide,
3-Benzylamino-4-[3-(3-piperidinomethylphenoxy)-propylamino]-1,2,5-thiadiazole 1,1-dioxide,
3-(3-Methoxybenzylamino)-4-[3-(3-piperidinomethylphenoxy)propylamino]-1,2,5-thiadiazole 1,1-dioxide,
3-(4-Methoxybenzylamino)-4-[3-(3-piperidinomethylphenoxy)propylamino]-1,2,5-thiadiazole 1,1-dioxide,
3-(3,4-Dimethoxybenzylamino)-4-[3-(3-piperidinomethylphenoxy)propylamino]-1,2,5-thiadiazole 1,1-dioxide,
3-(3,4-Methylenedioxybenzylamino)-4-[3-(3-piperidinomethylphenoxy)propylamino]-1,2,5-thiadiazole 1,1-dioxide,
3-(4-Chlorobenzylamino)-4-[3-(3-piperidinomethylphenoxy)propylamino]-1,2,5-thiadiazole 1,1-dioxide,
3-[(2-Pyridyl)methylamino]-4-[3-(3-piperidinomethylphenoxy)propylamino]-1,2,5-thiadiazole 1,1-dioxide,
3-[(3-Pyridyl)methylamino]-4-[3-(3-piperidinomethylphenoxy)propylamino]-1,2,5-thiadiazole 1,1-dioxide, and
3-[(4-Pyridyl)methylamino]-4-[3-(3-piperidinomethylphenoxy)propylamino]-1,2,5-thiadiazole 1,1-dioxide, respectively.

EXAMPLE 148

The general procedures of Example 147 are repeated except that the 3,4-dimethoxy-1,2,5-thiadiazole 1,1-dioxide utilized therein is replaced by an equimolar amount of 3,4-dimethoxy-1,2,5-thiadiazole 1-oxide, and there are thereby produced
3-Ethylamino-4-[3-(3-piperidinomethylphenoxy)-propylamino]-1,2,5-thiadiazole 1-oxide,
3-Propylamino-4-8 3-(3-piperidinomethylphenoxy)-propylamino]-1,2,5-thiadiazole 1-oxide, 3-Butylamino-4-[3-(3-piperidinomethylphenoxy)-propylamino]-1,2,5-thiadiazole 1-oxide,
3-Allylamino-4-[3-(3-piperidinomethylphenoxy)-propylamino]-1,2,5-thiadiazole 1-oxide,
3-(2-Propynyl)amino-4-[3-(3-piperidinomethylphenoxy)propylamino]-1,2,5-thiadiazole 1-oxide,
3-(Cyclopropylamino)-4-[3-(3-piperidinomethylphenoxy)propylamino]-1,2,5-thiadiazole 1-oxide,
3-[(Cyclopropyl)methylamino]-4-[3-(3-piperidinomethylphenoxy)propylamino]-1,2,5-thiadiazole 1-oxide,
3-(2-Hydroxyethylamino)-4-[3-(3-piperidinomethylphenoxy)propylamino]-1,2,5-thiadiazole 1-oxide,
3-(2-Methoxyethylamino)-4-[3-(3-piperidinomethylphenoxy)propylamino]-1,2,5-thiadiazole 1-oxide,
3-(2,2,2-Trifluoroethylamino)-4-[3-(3-piperidinomethylphenoxy)propylamino]-1,2,5-thiadiazole 1-oxide,
3-(2-Fluoroethylamino)-4-[3-(3-piperidinomethylphenoxy)propylamino]-1,2,5-thiadiazole 1-oxide,
3-Hydroxyamino-4-[3-(3-piperidinomethylphenoxy)-propylamino]-1,2,5-thiadiazole 1-oxide,
3-(3-Cyanopropylamino)-4-[3-(3-piperidinomethylphenoxy)propylamino]-1,2,5-thiadiazole 1-oxide,
3-Benzylamino-4-[3-(3-piperidinomethylphenoxy)-propylamino]-1,2,5-thiadiazole 1-oxide,
3-(3-Methoxybenzylamino)-4-[3-(3-piperidinomethylphenoxy)propylamino]-1,2,5-thiadiazole 1-oxide,
3-(4-Methoxybenzylamino)-4-[3-(3-piperidinomethylphenoxy)propylamino]-1,2,5-thiadiazole 1-oxide,
3-(3,4-Dimethoxybenzylamino)-4-[3-(3-piperidinomethylphenoxy)propylamino]-1,2,5-thiadiazole 1-oxide,
3-(3,4-Methylenedioxybenzylamino)-4-[3-(3-piperidinomethylphenoxy)propylamino]-1,2,5-thiadiazole 1-oxide,
3-(4-Chlorobenzylamino)-4-[3-(3-piperidinomethylphenoxy)propylamino]-1,2,5-thiadiazole 1-oxide,
3-[(2-Pyridyl)methylamino]-4-[3-(3-piperidinomethylphenoxy)propylamino]-1,2,5-thiadiazole 1-oxide
3-[(3-Pyridyl)methylamino]-4-[3-(3-piperidinomethylphenoxy)propylamino]-1,2,5-thiadiazole 1-oxide, mp 139.5°-143° C., and
3-[(4-Pyridyl)methylamino]-4-[3-(3-piperidinomethylphenoxy)propylamino]-1,2,5-thiadiazole 1-oxide, respectively.

EXAMPLE 149

3-[(3-Pyridyl)methylamino]-4-[3-(3-piperidinomethylphenoxy)propylamino]-1,2,5-thiadiazole 1-oxide A solution of 3-(3-piperidinomethylphenoxy)propylamine (from the dihydrochloride, 3.21 g; 10.0 mmoles) in 30 ml of methanol was added dropwise over a period of 60 minutes to a partial solution of 3,4-dimethoxy-1,2,5-thiadiazole 1-oxide (1.62 g; 10.0 mmoles) that had been cooled to 5°-7° in an ice-water bath. After 3 hours at ambient temperature, a solution of 3-aminomethylpyridine (1.14 g; 10.5 mmoles) in 10 ml of methanol was added and the solution was then stirred for 18 hours. The reaction mixture was evaporated under reduced pressure and the residue chromatographed by flash chromatography on 100 g of silica gel (230-400 mesh) using methylene chloride-methanol-ammonia. The appropriate fractions were combined, evaporated and triturated with acetonitrile to give 4.05 g of product. Recrystallization from isopropyl alcohol yielded the title compound, mp 139.5°-143°.

Anal. Calc'd. for $C_{23}H_{30}N_6O_2S$: C, 60.77; H, 6.65; N, 18.49; S, 7.04. Found: C, 60.66; H, 6.64; N, 18.22; S, 7.02.

EXAMPLE 150

3-Amino-4-[3-(3-guanidinophenoxy)propylamino]-1,2,5-thiadiazole 1-oxide

A. N-[3-(3-Nitrophenoxy)propyl]phthalimide

A partial suspension of m-nitrophenol (6.0 g; 43.0 mmoles), N-(3-bromopropyl)phthalimide (10.0 g; 37.0 mmoles) and potassium carbonate (8.0 g; 58.0 mmoles) in 50 ml of DMF was stirred at ambient temperature for 70 hours. The reaction mixture was diluted with 80 ml of water and filtered to give product. Recrystallization from 2-methoxyethanol yielded 9.15 g of the title compound, mp 149°-152°.

Anal. Calc'd. for $C_{17}H_{14}N_2O_5$: C, 62.57; H, 4.32; N, 8.59. Found: C, 62.49; H, 4.30; N, 8.71.

B. N-[3-(3-Aminophenoxy)propyl]phthalimide

A suspension of N-[3-(3-nitrophenoxy)propyl]phthalimide (1.0 g; 3.1 mmoles) [prepared in Step A] and 10% palladium on carbon (0.2 g) in 100 ml of 2-methoxyethanol was hydrogenated in a Parr Apparatus at ambient temperature for 45 minutes. The reaction mixture was filtered and the filtrate was evaporated to dryness to give 0.91 g of crude product.

An analytical sample was prepared by flash chromatography on silica gel using methylene chloride-methanol and recrystallization from absolute ethanol yielded the title compound, mp 157°-162°.

Anal. Calc'd. for $C_{17}H_{16}N_2O_3$: C, 68.91; H, 5.44; N, 9.45. Found: C, 69.00; H, 5.54; N, 9.52.

C. N-[3-(3-Guanidinophenoxy)propyl]phthalimide

A mixture of crude N-[3-(3-aminophenoxy)propyl]phthalimide (13.27 g; 45.0 mmoles) [prepared in Step B], 50% aqueous cyanamide (7.9 ml) and 12 N hydrochloric acid (3.78 ml; 45.0 mmoles) in 39.4 ml of absolute ethanol was heated at reflux for 2¼ hours. An additional 7.9 ml of 50% aqueous cyanamide was added and heating was continued for 15 hours. The reaction mixture was evaporated under reduced pressure and the residue chromatographed by flash chromatography on 120 g of silica gel (230-400 mesh) using methylene chloride-methanol. The appropriate fractions were combined, evaporated and triturated with cold acetonitrile to give 5.85 g of product. Recrystallization from absolute ethanol yielded the title compound as a hydrochloride salt, mp 185°-187°.

Anal. Calc'd. for $C_{18}H_{18}N_4O_3.HCl$: C, 57.68; H, 5.11; N. 14.95; Cl, 9.46. Found: C, 57.65; H, 5.55; N, 15.08; Cl, 9.16.

D. 3-(3-Guanidinophenoxy)propylamine

To a partial suspension of N-[3-(3-guanidinophenoxy)propyl]phthalimide hydrochloride (1.0 g; 2.95 mmoles) in 10 ml of 95% aqueous ethanol was added 0.27 ml of hydrazine hydrate. The mixture was stirred at ambient temperature for 17 hours and evaporated under reduced pressure to give the title compound. The product was used without further purification in Step E.

E. 3-Amino-4-[3-(3-guanidinophenoxy)-propylamino]-1,2,5-thiadiazole 1-oxide

To a solution of crude 3-(3-guanidinophenoxy)propylamine [prepared in Step D] in 10 ml of methanol was added 3-amino-4-methoxy-1,2,5-thiadiazole 1-oxide (0.59 g; 4.0 mmoles) and the mixture was stirred at ambient temperature for 17 hours and then heated at 50° for 2.5 hours. The reaction mixture was filtered, evaporated under reduced pressure and the residue was chromatographed by flash chromatography on 75 g of silica gel (230-400 mesh) using methanol-methylene chloride.

The appropriate fractions were combined and evaporated under reduced pressure to yield 0.25 g of the title compound as an oil; TLC [silica gel/CH$_2$Cl$_2$:CH$_3$OH (4:1)] gave Rf=0.21.

The NMR spectrum (60 MHz) in d$_6$ dimethyl sulfoxide gave the following resonances δ: 9.33 (s, 1H); 8.43 (s, 2H); 7.52 (m, 4H); 7.43 (m, 1H); 6.83 (m, 3H); 4.13 (broad t, 2H); 3.51 (broad t, 2H); 2.10 (broad t, 2H).

EXAMPLE 151

3-Amino-4-{2-[(5-piperidinomethyl-2-furyl)methylthio]ethylamino}-1,2,5-thiadiazole 1-oxide A. 3-Amino-4-methoxy-1,2,5-thiadiazole 1-oxide A 2.75 N solution of ammonia (56.0 ml; 0.154 mmole) in methanol was added dropwise over 1 hour to a well-stirred solution of 3,4-dimethoxy-1,2,5-thiadiazole 1-oxide (24.3 g; 0.15 mole) in 725 ml of methanol at 20°. The resultant solution was stirred at ambient temperature for 3 hours and then was concentrated to about 125 ml at reduced pressure. After 16 hours at 0°, the mixture was filtered and dried to give 19.9 g of product.

An analytical sample was prepared by recrystallization from methanol to yield the title compound, mp 182°–184° (dec.)

Anal. Calc'd. for C$_3$H$_5$N$_3$O$_2$S: C, 24.49; H, 3.43; N, 28.56; S, 21.79. Found: C, 24.22; H, 3.63; N, 28.60; S, 21.92.

B. 3-Amino-4-{2-[(5-piperidinomethyl-2-furyl)methylthio]ethylamino}-1,2,5-thiadiazole 1-oxide A solution of 2-[(5-piperidinomethyl-2-furyl)methylthio]ethylamine (4.0 g; 15.7 mmoles) [prepared according to the procedure described in Belgian Patent No. 857,388 (U.S. Pat. No. 4,128,658)] in 25 ml of methanol was added all at once to a stirred suspension of 3-amino-4-methoxy-1,2,5-thiadiazole 1-oxide (2.31 g; 15.7 mmoles) [prepared in Step A] in 25 ml of methanol at ambient temperature. After stirring for 16 hours, the solution was evaporated under reduced pressure and the residue chromatographed by flash chromatography on 100 g of silica gel (230–400 mesh) using methanol-acetonitrile. The appropriate fractions were combined and evaporated to give 3.71 g of product. Recrystallization from 95% aqueous ethanol with charcoal treatment yielded the title compound, mp 161°–163°.

Anal. Calc'd. for C$_{15}$H$_{23}$N$_5$O$_2$S$_2$: C, 48.76; H, 6.27; N, 18.96; S, 17.36. Found: c, 48.86; H, 6.16; N, 19.66; S, 17.63.

I claim:

1. A compound of the formula

wherein p is 1 or 2;

R$^7$ is a leaving group selected from halogen, (lower)alkoxy, (lower)alkylthio, phenoxy, phenylthio, substituted phenoxy and substituted phenylthio wherein the phenyl ring may contain 1 or 2 substituents selected from halogen, (lower)alkyl, (lower)alkoxy and nitro; and R$^{12}$ is A(CH$_2$)$_m$Z(CH$_2$)$_n$NH—, R$^2$R$^3$N— or HS(CH$_2$)$_n$NH—; in which R$^2$ and R$^3$ each are independently hydrogen, (lower)alkyl, (lower)alkenyl, (lower)alkynyl, cyclo(lower)alkyl(lower)alkyl, hydroxy(lower)alkyl, (lower)alkoxy(lower)alkyl, (lower)alkylthio(lower)alkyl, 2-fluoroethyl, 2,2,2-trifluoroethyl or cyano(lower)alkyl, or, when R$^2$ is hydrogen, R$^3$ may also be cyclo(lower)alkyl, amino(lower)alkyl, (lower)alkylamino(lower)alkyl, di(lower)alkylamino(lower)alkyl, pyrrolidino(lower)alkyl, piperidino(lower)alkyl, piperazino(lower)alkyl, substituted pyridyl(lower)alkyl wherein the pyridyl ring may contain one substituent selected from (lower)alkyl, (lower)alkoxy, hydroxy, amino and halogen, amino, (lower)alkylamino, di(lower)alkylamino, hydroxy, (lower)alkoxy, 2,3-dihydroxypropyl, cyano, amidino, (lower)alkylamidino, phenyl, phenyl(lower)alkyl, substituted phenyl or substituted phenyl(lower)alkyl, wherein the phenyl ring may contain one or two substituents independently selected from (lower)alkyl, hydroxy, (lower)alkoxy and halogen or one substituent selected from methylenedioxy, trifluoromethyl and di(lower)alkylamino; or R$^2$ and R$^3$, taken together, may be —CH$_2$CH$_2$X(CH$_2$)$_r$—;

r is an integer of from 1 to 3, inclusive;

X is methylene, sulfur, oxygen or N—R$^4$, provided that, when p is 2 and R$^7$ is methoxy, R$^2$ and R$^3$ taken together with the nitrogen to which they are attached, may not be morpholino, and that, when r is 1, X is methylene;

R$^4$ is hydrogen, (lower)alkyl, (lower)alkenyl, (lower)alkynyl, (lower)alkanoyl or benzoyl;

m is an integer of from zero to 2, inclusive;

n is an integer of from 2 to 4, inclusive;

Z is sulfur, oxygen or methylene;

A is phenyl, imidazolyl, thiazolyl, isothiazolyl, oxazolyl, isoxazolyl, triazolyl, thiadiazolyl, oxadiazolyl, furyl, thienyl or pyridyl; provided that A may contain one or two substituents, the first substituent being selected from (lower)alkyl, hydroxy, trifluoromethyl, halogen, amino, hydroxymethyl, (lower)alkoxy,

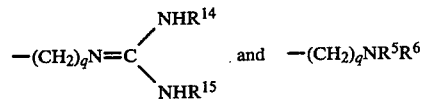

and the second substituent being selected from (lower)alkyl, hydroxy, trifluoromethyl, halogen, amino, hydroxymethyl and (lower)alkoxy;

q is an integer of from 0 to 6, inclusive;

R$^{14}$ and R$^{15}$ independently are hydrogen or (lower)alkyl, or if R$^{14}$ is hydrogen, R$^{15}$ also may be (lower)alkanoyl or benzoyl, or R$^{14}$ and R$^{15}$, taken together, may be ethylene; and R$^5$ and R$^6$ each are independently hydrogen, (lower)alkyl, (lower)alkenyl, (lower)alkynyl, (lower)alkoxy(lower)alkyl, cyclo(lower)alkyl or phenyl, provided that R$^5$ and R$^6$ may not both be cyclo(lower)alkyl or phenyl; or R$^5$ and R$^6$, taken together with the nitrogen atom to which they are attached, may be pyrrolidino, methylpyrrolidino, dimethylpyrrolidino, piperidino, methylpiperidino, dimethylpiperidino, hydroxypiperidino, homopiperidino, heptamethyleneimino or octamethyleneimino; or a salt, hydrate, solvate or N-oxide thereof.

2. A compound of claim 1 wherein R$^{12}$ is A(CH$_2$)$_m$Z(CH$_2$)$_n$NH— in which A is phenyl, imidazolyl, thiazolyl, furyl, thienyl or pyridyl, each of which may contain one or two substituents, the first substituent being selected from (lower)alkyl,

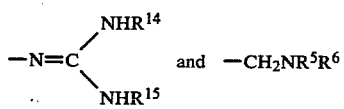

and the second substituent being selected from (lower)alkyl; Z is sulfur, oxygen or methylene; m is zero or one; n is two or three; $R^{14}$ and $R^{15}$ independently are hydrogen or (lower)alkyl, or $R^{14}$ and $R^{15}$, taken together, may be ethylene; $R^5$ and $R^6$ each are independently hydrogen or (lower)alkyl; or $R^5$ and $R^6$, taken together with the nitrogen atom to which they are attached, may be pyrrolidino, methylpyrrolidino, dimethylpyrrolidino, piperidino, methylpiperidino, dimethylpiperidino, hydroxypiperidino, homopiperidino, heptamethyleneimino or octamethyleneimino; and $R^7$ is (lower)alkoxy.

3. A compound of claim 1 wherein $R^{12}$ is

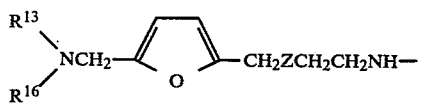

in which Z is sulfur or methylene, $R^{16}$ is methyl and $R^{13}$ is hydrogen or methyl, or $R^{16}$ and $R^{13}$, taken together with the nitrogen atom to which they are attached, may be piperidino; and $R^7$ is (lower)alkoxy.

4. A compound of claim 3 wherein $R^7$ is methoxy.
5. A compound of claim 1 wherein $R^{12}$ is

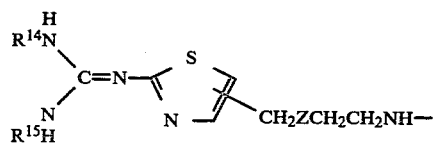

in which Z is sulfur or methylene; $R^{14}$ and $R^{15}$ independently are hydrogen or methyl, or $R^{14}$ and $R^{15}$, taken together, may be ethylene; and $R^7$ is (lower)alkoxy.

6. A compound of claim 5 wherein $R^7$ is methoxy.
7. A compound of claim 1 wherein $R^{12}$ is

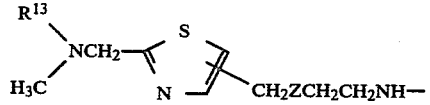

in which $R^{13}$ is hydrogen or methyl; Z is sulfur or methylene; and $R^7$ is (lower)alkoxy.

8. A compound of claim 7 wherein $R^7$ is methoxy.
9. A compound of claim 1 wherein $R^{12}$ is

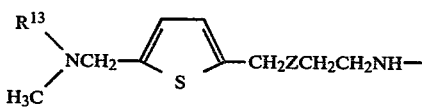

in which $R^{13}$ is hydrogen or methyl; Z is sulfur or methylene; and $R^7$ is (lower)alkoxy.

10. A compound of claim 9 wherein $R^7$ is methoxy.
11. A compound of claim 1 wherein $R^{12}$ is

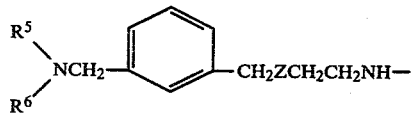

in which $R^5$ and $R^6$ each are independently hydrogen or (lower)alkyl, or, $R^5$ and $R^6$, taken together with the nitrogen atom to which they are attached, may be piperidino; Z is sulfur or methylene; and $R^7$ is (lower)alkoxy.

12. A compound of claim 11 wherein $R^7$ is methoxy.
13. A compound of claim 1 wherein $R^{12}$ is

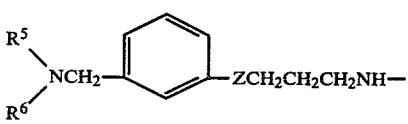

in which Z is oxygen or sulfur; $R^5$ and $R^6$ each are independently hydrogen or (lower)alkyl, or when $R^5$ is hydrogen, $R^6$ also may be (lower)alkenyl or (lower)alkynyl; or $R^5$ and $R^6$, taken together with the nitrogen to which they are attached, may be pyrrolidino, methylpyrrolidino, piperidino, methylpiperidino, dimethylpiperidino, homopiperidino or heptamethyleneimino; and $R^7$ is (lower)alkoxy.

14. A compound of claim 13 wherein $R^7$ is methoxy.
15. A compound of claim 14 wherein $R^5$ and $R^6$ each are independently hydrogen or (lower)alkyl.
16. A compound of claim 14 wherein $R^5$ and $R^6$, taken together with the nitrogen to which they are attached, represent piperidino.
17. A compound of claim 1 wherein $R^{12}$ is

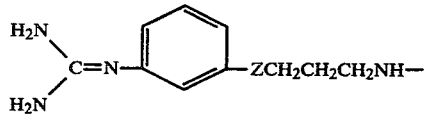

in which Z is oxygen or sulfur; and $R^7$ is (lower)alkoxy.

18. A compound of claim 17 wherein $R^7$ is methoxy.
19. A compound of claim 1 wherein $R^{12}$ is $R^2R^3N-$ in which $R^2$ and $R^3$ each are independently hydrogen, (lower)alkyl, (lower)alkenyl, (lower)alkynyl or cyclo(lower)alkyl(lower)alkyl, or, when $R^2$ is hydrogen, $R^3$ also may be substituted pyridyl(lower)alkyl wherein the pyridyl ring may contain one substituent selected from (lower)alkyl, (lower)alkoxy, hydroxy, amino and halogen, phenyl(lower)alkyl or 3,4-methylenedioxybenzyl; and $R^7$ is (lower)alkoxy.

20. A compound of claim 19 wherein $R^7$ is methoxy.
21. The compound of claim 20 which is 3-amino-4-methoxy-1,2,5-thiadiazole 1-oxide.
22. A compound of claim 1 wherein $R^{12}$ is $HS(CH_2)_nNH-$ in which n is an integer of from two to four; and $R^7$ is (lower)alkoxy.
23. A compound of claim 22 wherein $R^7$ is methoxy.

* * * * *

UNITED STATES PATENT AND TRADEMARK OFFICE
CERTIFICATE OF CORRECTION

PATENT NO. : 4,380,638

DATED : April 19, 1983

INVENTOR(S) : Ronnie Ray Crenshaw et al.

It is certified that error appears in the above—identified patent and that said Letters Patent is hereby corrected as shown below:

In Column 16, structure Ih should be

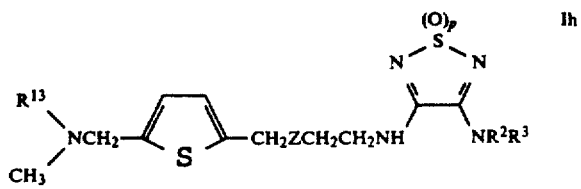

In Column 28 (Table 1), the $ED_{50}$ for the compound of Example 99 should be -- 32 (5.7-200) -- .

In Column 29 (Table 1), the $ED_{50}$ for the compound of Example 146d should be -- 0.28 (0.066-1.21) -- .

In Column 90 line 26, Claim 1, the phrase "may not be morpholino" should read -- may not be piperidino or morpholino --.

Signed and Sealed this

Twelfth Day of July 1983

[SEAL]

Attest:

Attesting Officer

GERALD J. MOSSINGHOFF

Commissioner of Patents and Trademarks